(12) United States Patent
Woolford

(10) Patent No.: US 9,889,246 B2
(45) Date of Patent: Feb. 13, 2018

(54) CASSETTE FOR A SURGICAL FLUID MANAGEMENT PUMP SYSTEM

(71) Applicant: Brady Woolford, Mapleton, UT (US)

(72) Inventor: Brady Woolford, Mapleton, UT (US)

(73) Assignee: STRYKER CORPORATION, Kalamazoo, MI (US)

(*) Notice: Subject to any disclaimer, the term of this patent is extended or adjusted under 35 U.S.C. 154(b) by 0 days.

(21) Appl. No.: 15/433,549

(22) Filed: Feb. 15, 2017

(65) Prior Publication Data

US 2017/0157312 A1  Jun. 8, 2017

Related U.S. Application Data

(63) Continuation of application No. 13/803,511, filed on Mar. 14, 2013, now Pat. No. 9,603,990, which is a (Continued)

(51) Int. Cl.
*F04B 43/12* (2006.01)
*A61M 3/02* (2006.01)
(Continued)

(52) U.S. Cl.
CPC ....... *A61M 3/0258* (2013.01); *A61B 17/1659* (2013.01); *A61B 17/320016* (2013.01); *A61B 18/14* (2013.01); *A61M 1/0031* (2013.01); *A61M 3/0216* (2014.02); *A61M 39/1011* (2013.01); *A61M 39/24* (2013.01); *A61M 39/28* (2013.01); *F04B 43/0072* (2013.01); *F04B 43/12* (2013.01); *F04B 51/00* (2013.01); *F04B 53/16* (2013.01); *A61B 2018/00565* (2013.01); *A61B 2018/00577* (2013.01); *A61B 2217/007* (2013.01); *A61B 2218/002* (2013.01); *A61M 2205/12* (2013.01); *A61M 2205/18* (2013.01); *A61M 2205/3331* (2013.01); *A61M 2205/3334* (2013.01); *A61M 2205/50* (2013.01); (Continued)

(58) Field of Classification Search
CPC ............ A61M 3/0258; A61M 2205/12; A61M 2205/128; A61M 2205/3344; F04B 43/12; F04B 43/1238; F04B 43/1246; F04B 43/1269; F04B 43/1284
USPC ................ 417/474, 476, 477.1, 477.2, 477.3
See application file for complete search history.

(56) References Cited

U.S. PATENT DOCUMENTS

| | | |
|---|---|---|
| 4,222,391 A | 9/1980 | Rawson et al. |
| 4,540,350 A | 9/1985 | Streicher |

(Continued)

OTHER PUBLICATIONS

"Flocontrol Arthroscopy Pump Manual", published in 2004, pp. 1-52 (60 pages).

(Continued)

*Primary Examiner* — Patrick Hamo
(74) *Attorney, Agent, or Firm* — Flynn, Thiel, Boutell & Tanis, P.C.

(57) ABSTRACT

A pump system including a pump, an inflow cassette and an outflow cassette. The inflow cassette has a damping flexible membrane covering a damping region configured to dampen pressure pulsations in washing fluid passing through the damping region. The pump has a plurality of individually actionable pressing members that can each be individually actuated to pinch one of a plurality of suction tubes of the outflow cassette to at least partially prevent fluid flow through the one of the plurality of the suction tubes.

24 Claims, 51 Drawing Sheets

Related U.S. Application Data continuation-in-part of application No. 13/782,660, filed on Mar. 1, 2013, now Pat. No. 9,289,110.

(60) Provisional application No. 61/620,814, filed on Apr. 5, 2012.

(51) Int. Cl.
| | |
|---|---|
| A61M 1/00 | (2006.01) |
| A61M 39/28 | (2006.01) |
| A61M 39/10 | (2006.01) |
| A61M 39/24 | (2006.01) |
| A61B 17/32 | (2006.01) |
| A61B 17/16 | (2006.01) |
| A61B 18/14 | (2006.01) |
| F04B 43/00 | (2006.01) |
| F04B 53/16 | (2006.01) |
| F04B 51/00 | (2006.01) |
| A61B 18/00 | (2006.01) |

(52) U.S. Cl.
CPC ... *A61M 2205/52* (2013.01); *A61M 2205/584* (2013.01); *A61M 2205/6054* (2013.01)

(56) References Cited

U.S. PATENT DOCUMENTS

| | | |
|---|---|---|
| 4,902,277 A | 2/1990 | Mathies et al. |
| 4,979,940 A | 12/1990 | Bobo, Jr. et al. |
| 5,000,733 A | 3/1991 | Mathies et al. |
| 5,399,160 A | 3/1995 | Dunberger et al. |
| 5,520,638 A | 5/1996 | O'Quinn et al. |
| 5,542,928 A | 8/1996 | Evans et al. |
| 5,630,799 A | 5/1997 | Beiser et al. |
| 5,662,611 A | 9/1997 | Beiser et al. |
| 5,882,339 A | 3/1999 | Beiser et al. |
| 5,892,160 A | 4/1999 | Hall |
| 5,927,956 A | 7/1999 | Lim et al. |
| 5,959,557 A | 9/1999 | Lim |
| 6,086,542 A | 7/2000 | Glowa et al. |
| 6,162,194 A | 12/2000 | Shipp |
| 6,295,877 B1 | 10/2001 | Aboul-Hosn et al. |
| 6,396,583 B1 | 5/2002 | Clare |
| 6,468,059 B2 | 10/2002 | Haser et al. |
| 6,626,355 B2 | 9/2003 | Sasse et al. |
| 6,699,244 B2 | 3/2004 | Carranza et al. |
| 6,896,664 B2 | 5/2005 | Novak |
| 7,150,713 B2 | 12/2006 | Shener et al. |
| 7,273,359 B2 | 9/2007 | Blight et al. |
| 7,287,968 B2 | 10/2007 | Haser et al. |
| 7,297,143 B2 | 11/2007 | Woloszko et al. |
| 7,371,224 B2 | 5/2008 | Haischmann et al. |
| 7,445,596 B2 | 11/2008 | Kucklick et al. |
| 7,503,893 B2 | 3/2009 | Kucklick |
| 7,510,542 B2 | 3/2009 | Blight |
| 7,526,960 B2 | 5/2009 | Francisco et al. |
| 7,604,610 B2 | 10/2009 | Shener et al. |
| 7,661,582 B2 | 2/2010 | Möllstam |
| 7,678,070 B2 | 3/2010 | Kumar et al. |
| 7,981,073 B2 | 7/2011 | Möllstam et al. |
| 8,123,676 B2 | 2/2012 | Kucklick |
| 8,206,342 B2 | 6/2012 | Hacker et al. |
| 8,262,603 B2 | 9/2012 | Shener et al. |
| 2007/0021713 A1 | 1/2007 | Kumar et al. |
| 2007/0060915 A1 | 3/2007 | Kucklick |
| 2007/0217933 A1 | 9/2007 | Haser et al. |
| 2007/0249993 A1 | 10/2007 | Mollstam et al. |
| 2008/0077128 A1 | 3/2008 | Woloszko et al. |
| 2008/0154095 A1 | 6/2008 | Stubkjaer et al. |
| 2010/0076372 A1 | 3/2010 | Hacker et al. |
| 2010/0155465 A1 | 6/2010 | Mollstam et al. |
| 2012/0035417 A1 | 2/2012 | Möllstam et al. |

OTHER PUBLICATIONS fms duo® + Fluid management system, Integrated shaver/pump system, published before Dec. 5, 2006 (4 pages).

"FMS Solo Manual" published before Jan. 2010, pp. 4-30 (28 pages).

"Flosteady Arthroscopy Pump", published Oct. 12, 2012, pp. 1-61 (68 sheets).

fms solo® Advanced Irrigation Pump, Irrigation System, published before Dec. 5, 2006 (2 pages).

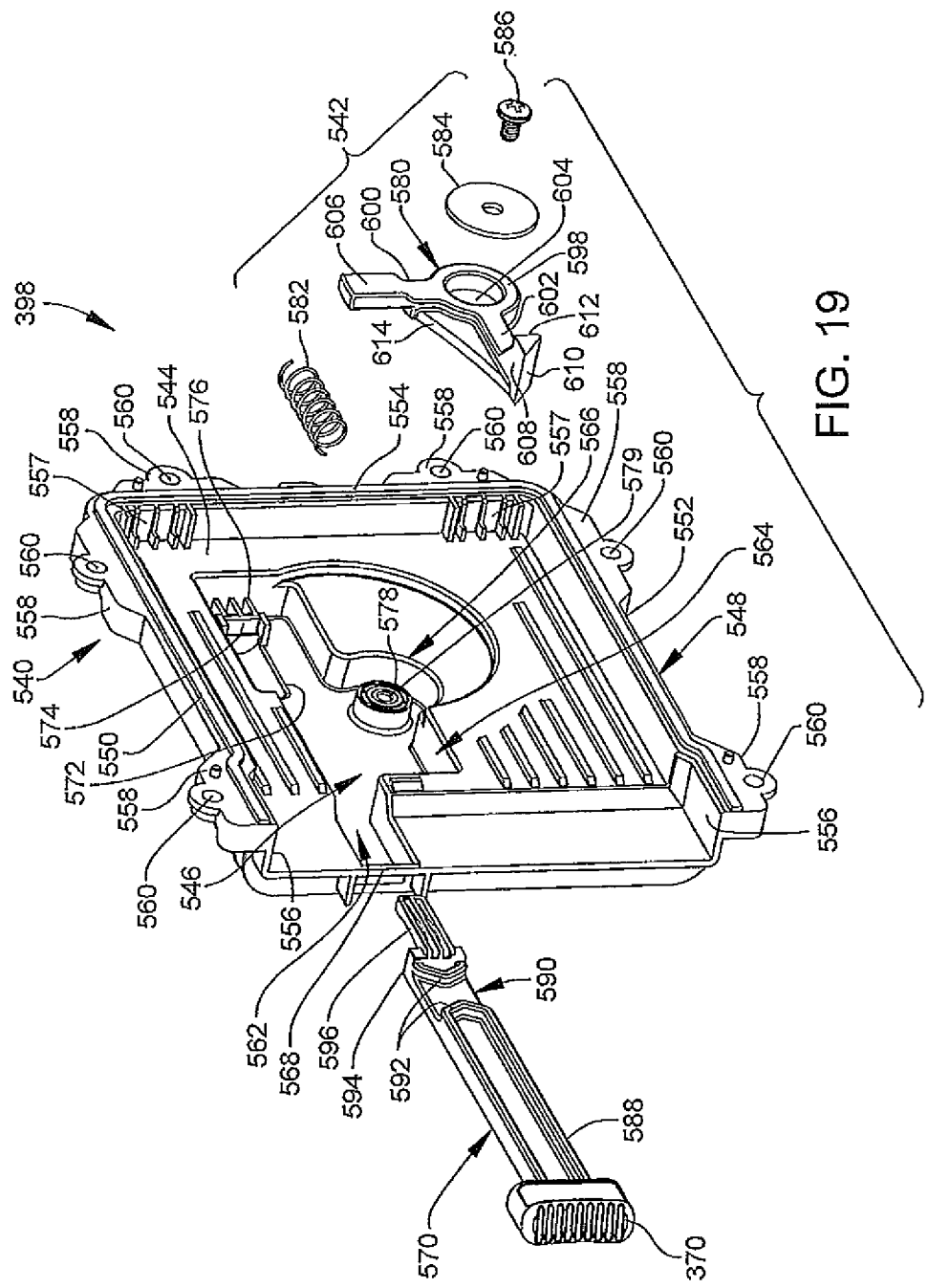

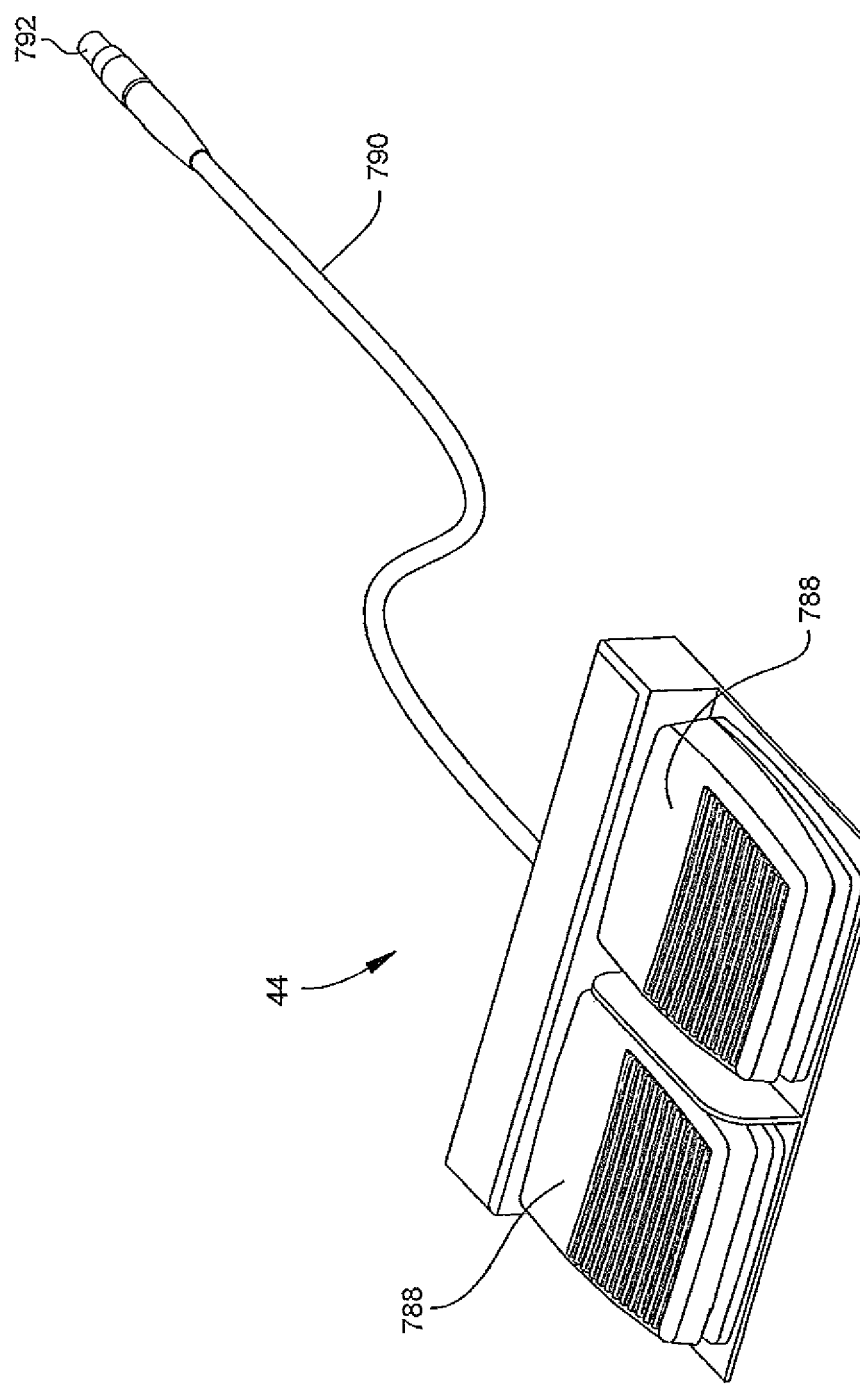

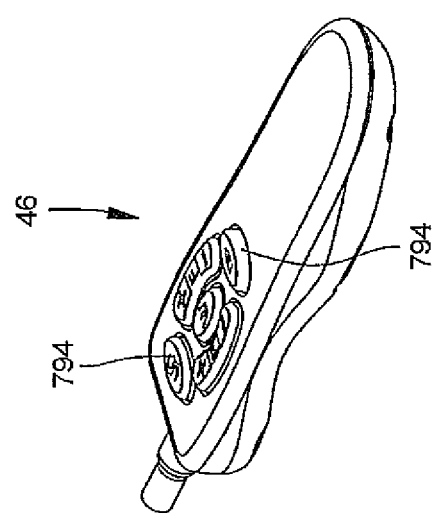

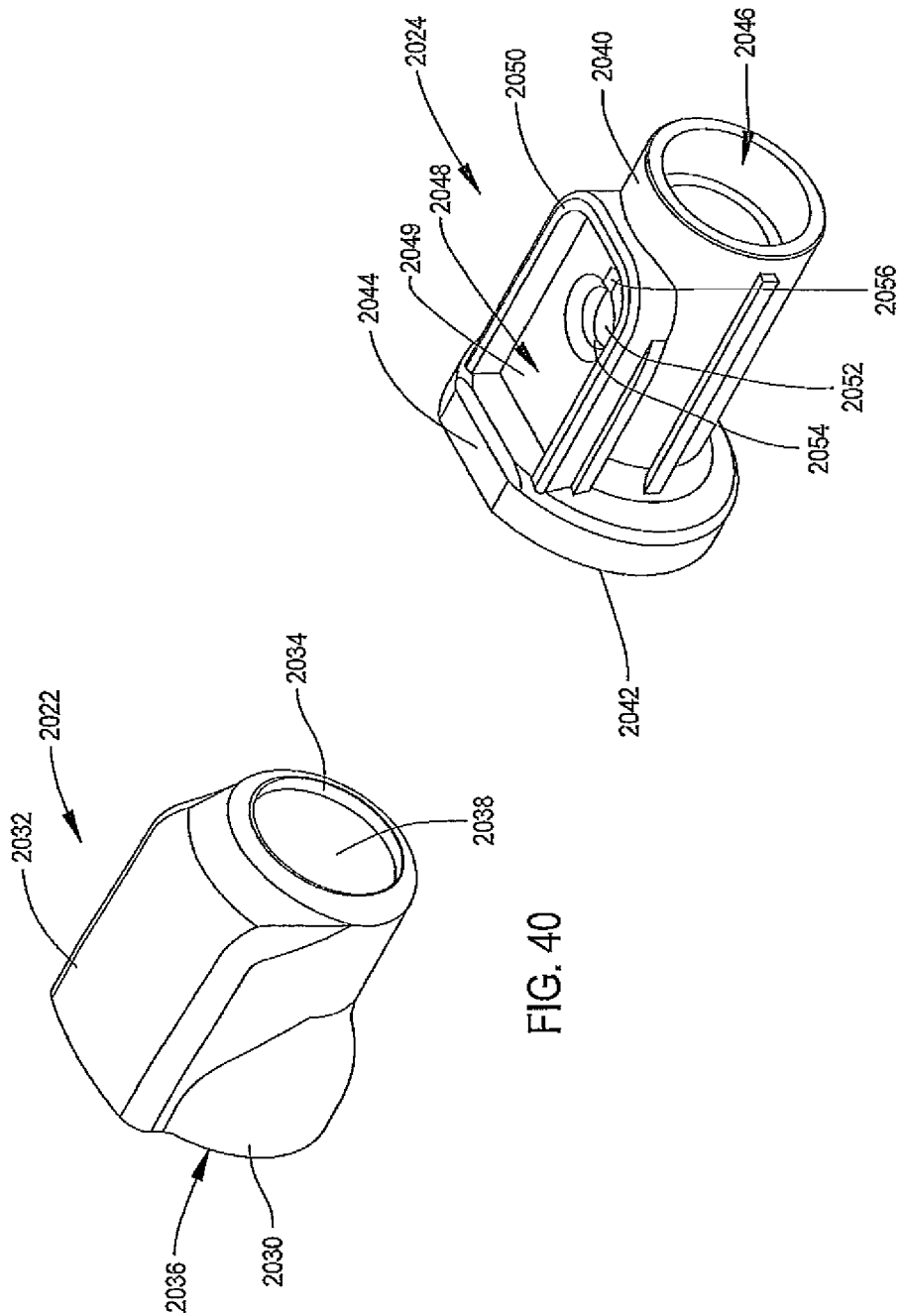

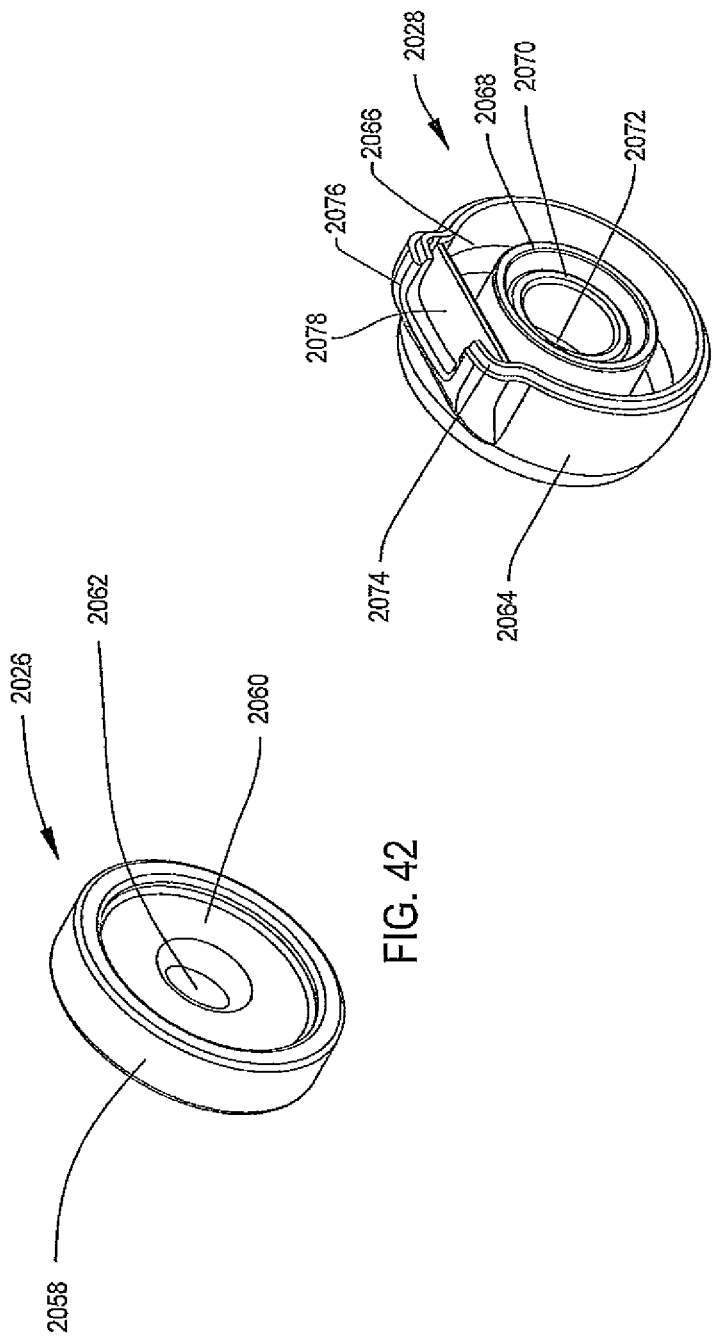

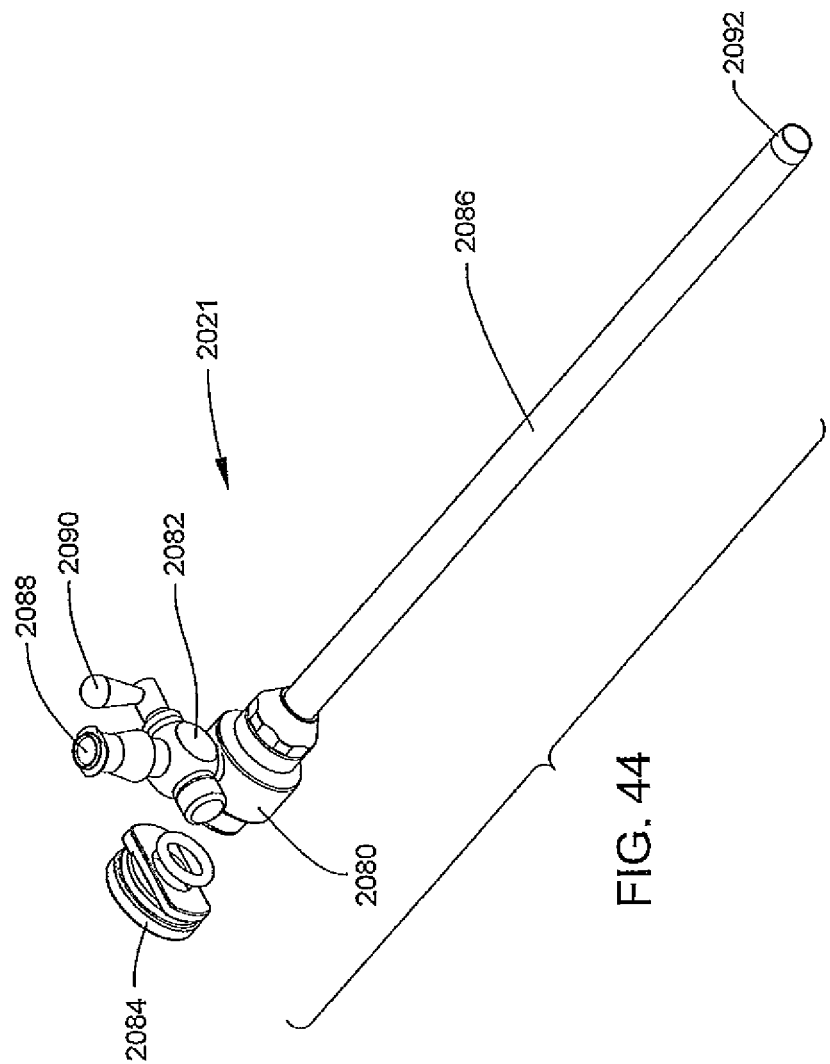

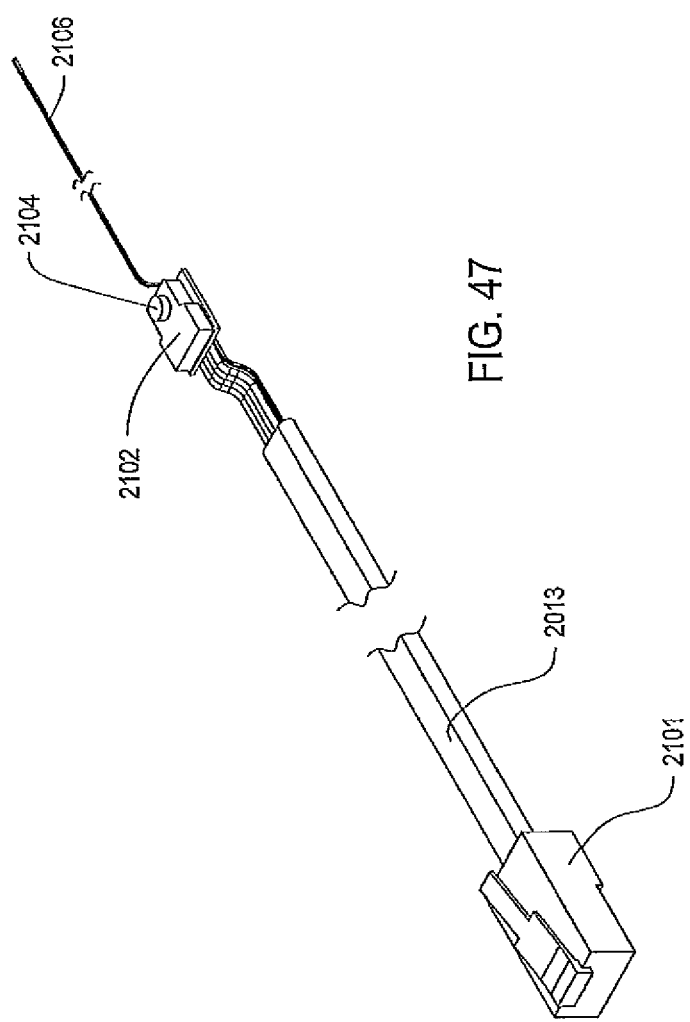

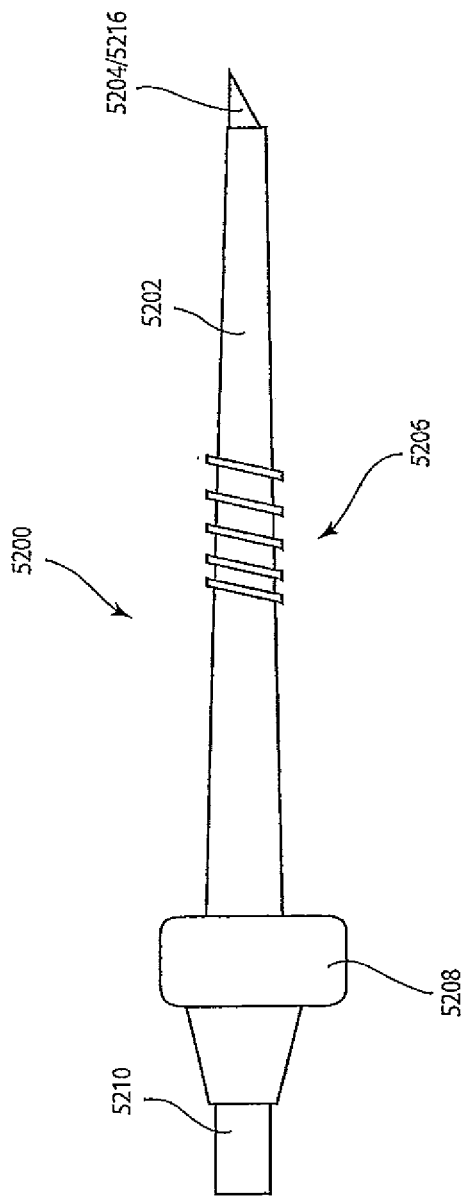
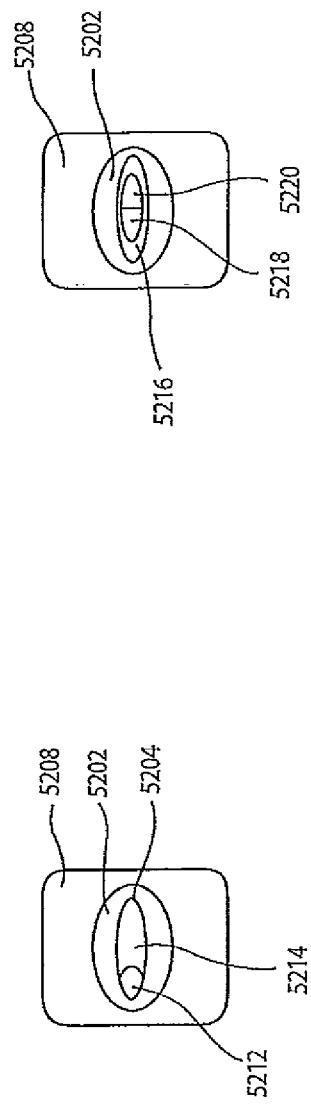
FIG. 52
FIG. 53A
FIG. 53B

CASSETTE FOR A SURGICAL FLUID MANAGEMENT PUMP SYSTEM

CROSS-REFERENCE TO RELATED APPLICATIONS

This is a continuation of U.S. patent application Ser. No. 13/803,511, filed Mar. 14, 2013, which issued as U.S. Pat. No. 9,603,990, which claims priority to U.S. Provisional Patent Application No. 61/620,814, filed Apr. 5, 2012, the disclosure of which is hereby incorporated by reference in its entirety. The '511 application is also a continuation-in-part of U.S. patent application Ser. No. 13/782,660, filed Mar. 1, 2013, which issued as U.S. Pat. No. 9,289,110, the disclosure of which is hereby incorporated by reference in its entirety.

FIELD OF THE INVENTION

This invention relates generally to pump system and, more particularly, to pump and auxiliary devices for surgical procedures.

BACKGROUND OF THE INVENTION

Fluid management pump systems are employed during surgical procedures to introduce sterile solution into surgical sites. One such procedure in which a fluid management pump is employed is during an endoscopic surgical procedure. In endoscopic surgery, an endoscope is inserted into the body at the site where the surgical procedure is to be performed. The endoscope is a surgical instrument that provides a view of the portion of the body in which it is inserted. Other surgical instruments are placed in the body at the surgical site. The surgeon views the surgical site through the endoscope in order to manipulate the other surgical instruments. The development of endoscopes and their companion surgical instruments has made it possible to perform minimally invasive surgery that eliminates the need to make large incisions to gain access to the surgical site. Instead, during endoscopic surgery, small openings, called portals, are formed in the patient. An advantage of performing endoscopic surgery is that since the portions of the body that are cut open are minimized, the portions of the body that need to heel after the surgery are likewise reduced. Still another advantage of endoscopic surgery is that it exposes less of the interior tissue of the patient's body to the open environment. This minimal opening of the patient's body lessens the extent to which the patient's internal tissue and organs are open to infection.

The ability to perform endoscopic surgery is enhanced by the development of fluid management pumps. A fluid management pump is designed to pump a sterile solution into the enclosed portion of the body at which the endoscopic surgical procedure is being performed. This solution expands and separates the tissue at the surgical site so as to increase both the field of view of the surgical site and the space available to the surgeon for manipulating the surgical instruments. One type of endoscopic surgery in which fluid management pumps have proven especially useful is in arthroscopic surgery. In arthroscopic surgery, a specially designed endoscope, called arthroscope, is employed to examine inter-bone joints and the ligaments and muscles that connect the bones. A fluid management pump is often employed in arthroscopic surgery to expand the space between the bones and adjacent soft tissue in order to increase the field in which the surgeon can perform the intended surgical procedure. Fluid management pumps are, during arthroscopic surgery, used to increase the surgical view of the joints that form an elbow, a knee, a wrist, or an ankle. Fluid management pumps are used both in endoscope surgery and in other surgical procedures to remove debris generated by the procedure.

A fluid management pump system includes a number of different components. There is the pump unit that supplies the motive force for pumping the sterile solution through an inflow tube into the surgical site. The actuation of the pump is regulated by a control unit. The control unit receives as input signals both surgeon entered commands and an indication of the liquid-state fluid pressure at the surgical site. Still another component of a fluid management pump system is the tube set. The tube set includes the fluid communication tubes that are connected between the pump unit, the control unit and the surgical site in the patient which is infused with the distention fluid. The tube set includes the previously described inflow tube through which the solution is introduced into the surgical site. There is also an outflow tube through which the solution and any waste material carried therewith are removed from the surgical site. Fluid flow from the site can be regulated by a valve integral with the control unit that selectively opens and closes the outflow tube. The tube set also includes a pressure feedback tube. The pressure feedback tube provides a fluid communication path between the surgical site and the control unit so that a pressure transducer integral with the control unit can monitor the fluid pressure at the surgical site. The pressure signal the transducer supplies is used by the control unit to regulate the actuation of the pump unit and to control the open/closed state of the fluid outflow tube.

Most fluid management pump systems further include cannulae that are inserted into the patient. The cannulae function as the actual fluid communication paths between the surgical site and the tubes forming the tube set. In order to minimize the number of portals that need to be formed in the patient, a single cannula can be provided that provides both the fluid communication into the body for the inflow tube and the pressure feedback tube and that functions as the guide bore through which the endoscope is inserted. These particular cannulae are called pressure sensing cannulae.

SUMMARY OF THE INVENTION

An aspect of the present invention is to provide an inflow cassette for a pump comprising a housing, peristaltic tubing, an input tube and an inflow tube. The housing has an internal flow path including an ingress path section and an egress path section. The peristaltic tubing is connected to the housing and is fluidly located between the ingress path section and the egress path section. The input tube is fluidly connected to the ingress path section and being configured to provide a fluid to the housing, with the ingress path section being fluidly located between the input tube and the peristaltic tubing. The inflow tube is fluidly connected to the egress path section and being configured to provide the fluid to a patient, with the egress path section being fluidly located between the ingress path section and the inflow tube. The housing has a damping flexible membrane covering a damping region of the egress path section, with the damping flexible membrane being configured to dampen pressure pulsations in the fluid passing through the damping region.

Another aspect of the present invention is to provide a pump assembly comprising a pump housing and an inflow cassette. The pump housing has an inflow cassette receptacle therein, with the inflow cassette receptacle having a rotary motor rotating a wheel. The inflow cassette is configured to be inserted into the inflow cassette receptacle of the pump housing. The inflow cassette comprises a cassette housing, peristaltic tubing, an input tube and an inflow tube. The cassette housing has an internal flow path including an ingress path section and an egress path section. The peristaltic tubing is connected to the cassette housing and is fluidly located between the ingress path section and the egress path section. The input tube is fluidly connected to the ingress path section and is configured to provide a fluid to the cassette housing, with the ingress path section being fluidly located between the input tube and the peristaltic tubing. The inflow tube is fluidly connected to the egress path section and is configured to provide the fluid to a patient, with the egress path section being fluidly located between the ingress path section and the inflow tube. The wheel engages the peristaltic tubing when the inflow cassette is inserted into the inflow cassette receptacle of the pump housing. Rotation of the wheel by the rotary motor causes the fluid to be pushed through the inflow cassette from the input tube to the inflow tube. The cassette housing has a damping flexible membrane covering a damping region of the egress path section, with the damping flexible membrane being configured to dampen pressure pulsations in the fluid passing through the damping region.

Yet another aspect of the present invention is to provide a pump assembly having a pump housing and a cassette. The pump housing has a cassette receptacle therein. The cassette receptacle has a rotary motor rotating a wheel. The pump housing has a plurality of individually actionable pressing members. The cassette is configured to be inserted into the cassette receptacle of the pump housing. The cassette comprises a cassette housing, peristaltic tubing, a plurality of suction tubes and a waste tube. The cassette housing has an internal flow path including an ingress path section and an egress path section. The peristaltic tubing is connected to the cassette housing and is fluidly located between the ingress path section and the egress path section. The plurality of suction tubes are fluidly connected to the ingress path section, with the ingress path section being fluidly located between the peristaltic tubing and the plurality of suction tubes. The waste tube is fluidly connected to the egress path section and being configured to provide a fluid to a waste receptacle, with the egress path section being fluidly located between the waste tube and the peristaltic tubing. The wheel engages the peristaltic tubing when the cassette is inserted into the cassette receptacle of the pump housing. Rotation of the wheel by the rotary motor causes the fluid to be pushed through the cassette from the plurality of suction tubes to the input tube. The plurality of individually actionable pressing members can each be individually actuated to pinch one of the plurality of suction tubes to at least partially prevent fluid flow through the one of the plurality of suction tubes.

Another aspect of the present invention is to provide a pump system comprising a pump, an inflow cassette and an outflow cassette. The pump has an inflow cassette receptacle and an outflow cassette receptacle therein. Each of the inflow cassette receptacle and the outflow cassette receptacle have a rotary motor rotating a wheel. The pump has a plurality of individually actionable pressing members. The inflow cassette is configured to be inserted into the inflow cassette receptacle of the pump and comprises an inflow cassette housing having an inflow internal flow path, inflow peristaltic tubing connected to the inflow cassette housing, an input tube fluidly connected to the inflow internal flow path and being configured to provide a washing fluid to the inflow cassette housing, and an inflow tube fluidly connected to the inflow internal flow path and being configured to provide the washing fluid to a patient. The outflow cassette is configured to be inserted into the outflow cassette receptacle of the pump and comprises an outflow cassette housing having an outflow internal flow path, outflow peristaltic tubing connected to the outflow cassette housing, a plurality of suction tubes fluidly connected to the outflow internal flow path, and a waste tube fluidly connected to the outflow internal flow path. The wheel of the inflow cassette receptacle engages the inflow peristaltic tubing when the inflow cassette is inserted into the inflow cassette receptacle of the pump. Rotation of the wheel of the inflow cassette receptacle by the rotary motor of the inflow cassette receptacle causes the washing fluid to be pushed through the inflow cassette from the input tube to the inflow tube. The wheel of the outflow cassette receptacle engages the outflow peristaltic tubing when the outflow cassette is inserted into the outflow cassette receptacle of the pump. Rotation of the wheel of the outflow cassette receptacle by the rotary motor of the outflow cassette receptacle causes the waste fluid to be pushed through the outflow cassette from the plurality of suction tubes to the waste tube. The inflow cassette housing has a damping flexible membrane covering a damping region of the inflow internal flow path, with the damping flexible membrane being configured to dampen pressure pulsations in the washing fluid passing through the damping region. The plurality of individually actionable pressing members can each be individually actuated to pinch one of the plurality of suction tubes to at least partially prevent fluid flow through the one of the plurality of suction tubes.

BRIEF DESCRIPTION OF DRAWINGS

FIG. 19 is an exploded perspective view of an ejection housing section of the inflow cassette receptacle assembly of the pump of the present invention.

FIG. 23 is a perspective view of a foot pedal of the present invention.

FIG. 24 is a perspective view of a remote control for the pump of the present invention.

FIG. 40 is a perspective view of a housing outer shell of the in-joint sensor of FIG. 38.

FIG. 41 is a perspective view of an inner member which resides inside the housing of FIG. 40.

FIG. 42 is a perspective view of an inner ring which engages with the inner member of FIG. 41.

FIG. 43 is a perspective view of a proximal member which attaches to the outer shell of FIG. 40.

FIG. 44 is a perspective view of in-flow tubing to be used with the in-joint sensor of FIG. 38.

FIG. 46 is a cross-sectional view of the shaft of the in-flow tubing of the in-joint sensor taken along the line XLVI-XLVI in FIG. 38.

FIG. 47 is a perspective, bottom view of sensors and attached cable, which are part of the in-joint sensor of FIG. 38.

FIG. 52 is a side elevational view of a needle-scopic in-joint sensor which may be part of or connected to the pump system.

FIG. 53A is an elevational end view of a first embodiment of the needle-scopic in-joint sensor of FIG. 52.

FIG. 53B is an elevational end view of a second embodiment of the needle-scopic in-joint sensor of FIG. 52.

DETAILED DESCRIPTION OF PREFERRED EMBODIMENTS

For purposes of description herein, it is to be understood that the invention may assume various alternative orientations, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1A:
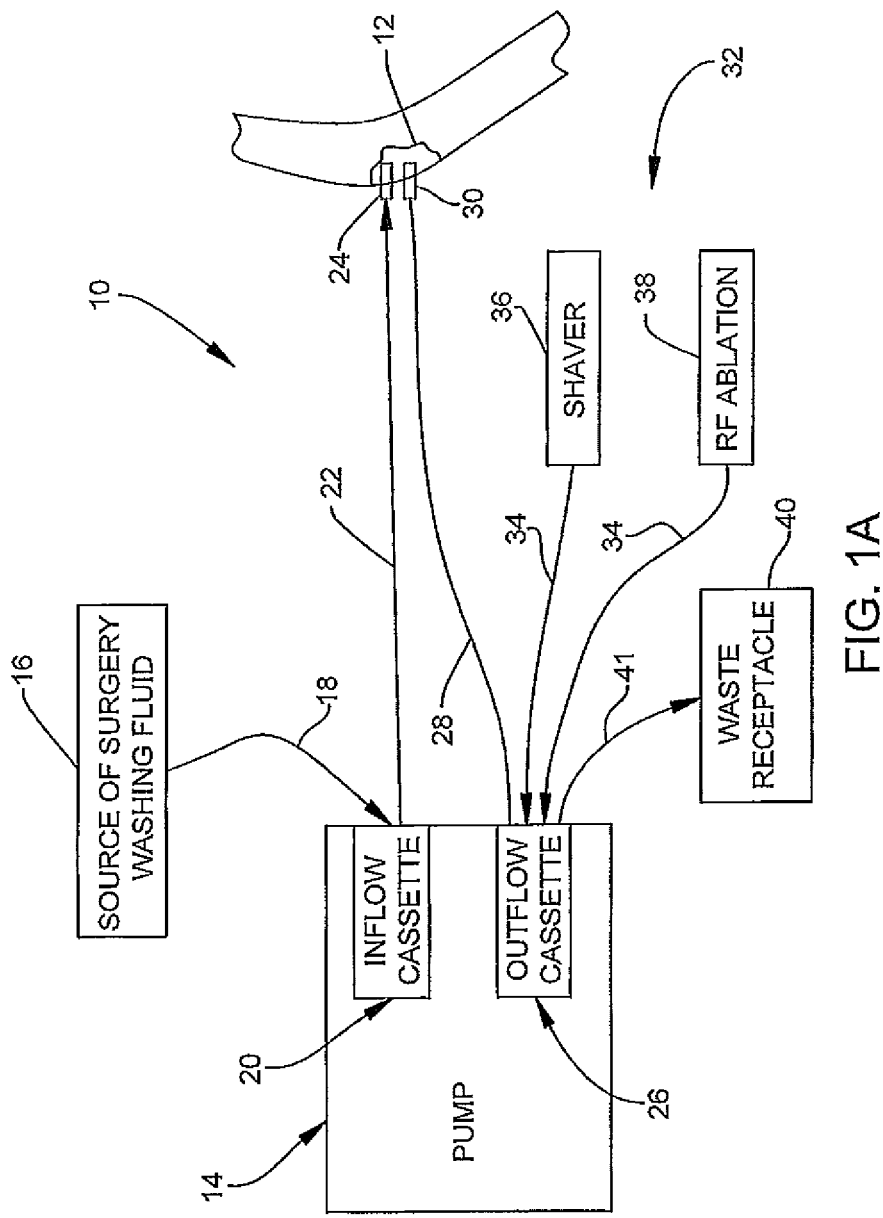
FIG. 1A is a schematic view of a pump system of the present invention illustrating flow paths through the pump system.

Referring to FIG. 1A, there is illustrated a pump system 10 of the present invention illustrating flow paths through the pump system 10. The pump system 10 includes a pump 14 configured to provide a surgery washing fluid to a body cavity 12 (e.g., a joint) during surgery and to suction waste fluid out of the body cavity 12.

As illustrated in FIG. 1A, the pump 14 receives a surgery washing fluid from a source of surgery washing fluid 16. The surgery washing fluid could be any washing fluid used in surgery and could be, for example, 0.9% saline or Ringer's lactate. The surgery washing fluid can provide irrigation to the body cavity 12, provide distension in a joint to give a surgeon room to operate in certain joints and/or provide tamponade to help with bleeding. Input tubing 18 is connected between the source of surgery washing fluid 16 and the pump 14 for supplying the surgery washing fluid to the pump 14. As illustrated in FIG. 1A, the pump 14 can have an inflow cassette 20 inserted therein for receiving the surgery washing fluid and for pushing the surgery washing fluid to the body cavity 12 through an inflow tube 22. Typically, the inflow tube 22 is inserted into and/or connected to an inflow cannula 24 inserted into the body cavity 12.

The illustrated pump 14 can also have an outflow cassette 26 inserted therein for suctioning the fluid out of the body cavity 12. An outflow tube 28 extends between the body cavity 12 and the outflow cassette 26, with the outflow tube 28 typically inserted into and/or connected to an outflow cannula 30 inserted into the body cavity 12. The outflow cassette 26 can also have one or more surgery devices 32 connected thereto by device suction tubing 34. The surgery devices 32 are configured to suction the fluid out of the body cavity 12 while the surgery devices 32 are being used within the body cavity 12. The surgery devices 32 can include a shaver 36, an RF ablation device 38 or any other surgery device that can suction waste fluid out of the body cavity 12. The outflow cassette 26 is connected to a waste receptacle 40 by waste tubing 41. The outflow cassette 26 works with the pump 14 to suction the waste fluid out of the body cavity 12 and to push the waste fluid into the waste receptacle 40 through the waste tubing 41. The input tubing 18, the inflow tube 22, the outflow tube 28, the device suction tubing 32 and the waste tubing 41 can have any length.

Figure 1B:
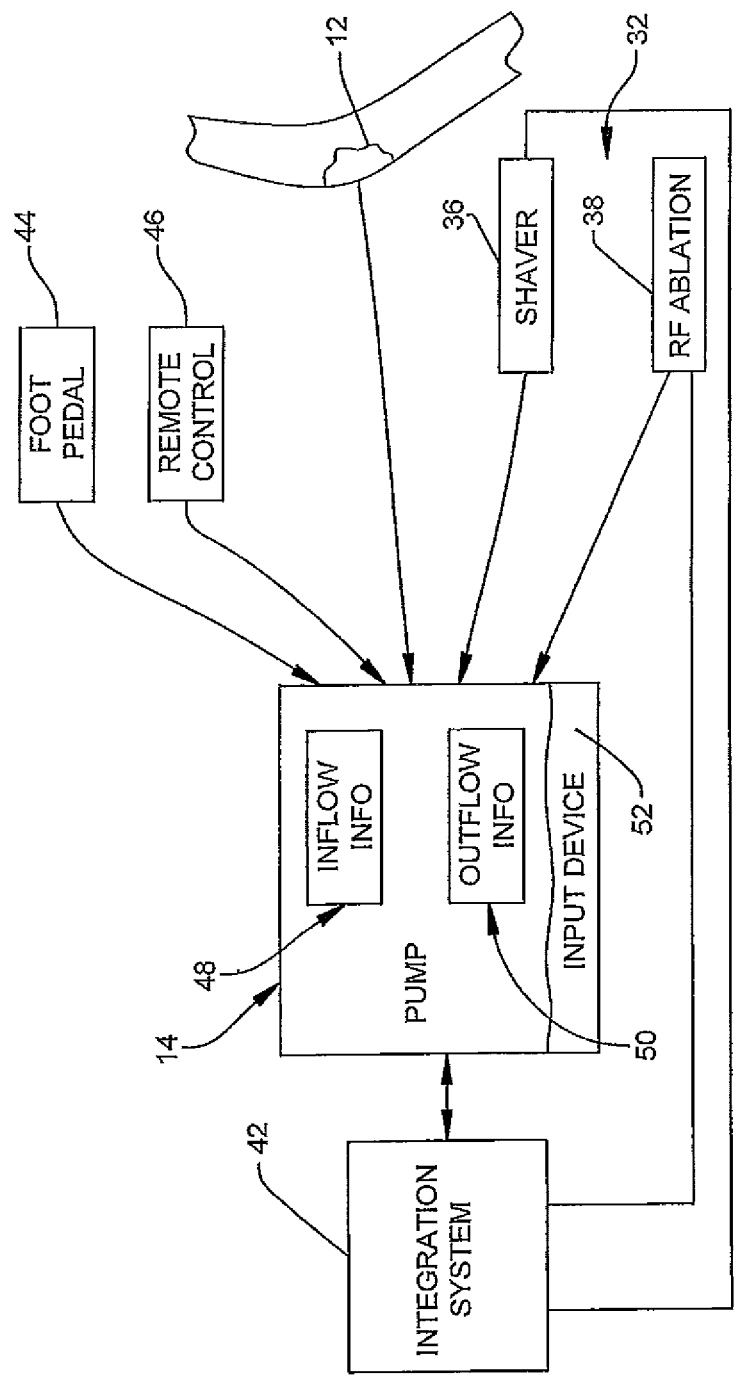
FIG. 1B is a schematic view of the pump system of the present invention illustrating communication paths through the system.

In the illustrated example, the pump system 10 can receive information from all elements of the pump system 10 to change the flow rate and/or pressure of the surgery washing fluid being provided to the body cavity 12 (i.e., inflow characteristics) and/or to change the flow rate and/or pressure of the waste fluid being suctioned from the body cavity 12 (i.e., outflow characteristics). FIG. 1B illustrates the information paths between the elements of the pump system 10 (which can be wired or wireless). In the illustrated example, the pump 14 and/or an integration system 42 can contain an algorithm for altering the inflow and/or outflow characteristics. Therefore, while most of the information paths are illustrated as being between the pump 14 and other elements, the information paths could lead to the integration system 42 instead of the pump 14. In some embodiments, the integration system 42 is disposed within a pump housing. The pump 14 and/or integration system 42 can include information from the body cavity 12 (e.g., pressure and temperature within the body cavity 12), the surgery devices 32 (e.g., the shaver 36 and/or the RF ablation device 38), a foot pedal 44, a remote control 46, inflow information 48 measured within the pump 14 including pressure information of the fluid outputted from the pump 14 and outflow information 50 measured within the pump 14 including pressure information of the fluid suctioned by the pump 14. The pump 14 can also include an input device 52 for inputting information directly into the pump 14 (e.g., a keyboard or touch screen). All of the information and how the information is used to alter the fluid inputs and outputs from the pump 14 are discussed in more detail below.

Figure 2:
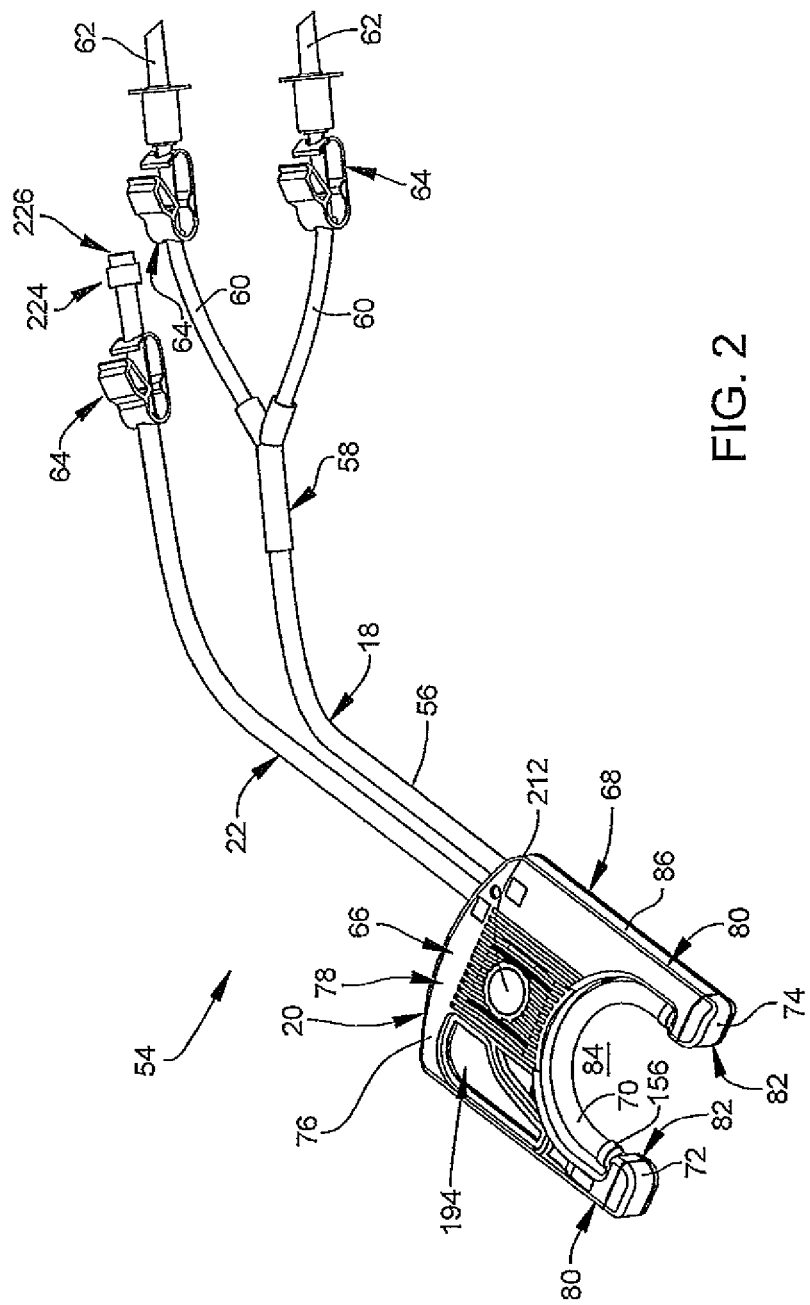
FIG. 2 is a perspective view of an inflow cassette tubing assembly of the present invention.

FIG. 2 illustrates an inflow cassette tubing assembly 54 for providing surgery washing fluid from the source of surgery washing fluid 16 to the body cavity 12. The inflow cassette tubing assembly 54 includes the input tubing 18, the inflow cassette 20 and the inflow tube 22. As explained in more detail below, the inflow cassette 20 is inserted into the pump 14 to push the surgery washing fluid through the inflow cassette 20.

In the illustrated example, the input tubing 18 is connected to the source of surgery washing fluid 16 and the inflow cassette 20. The input tubing 18 can be made of any tubing material and can be connected to the source of surgery washing fluid 16 in any manner. In the illustrated embodiment, the input tubing 18 includes a cassette connection portion 56, a Y-connector 58 and a pair of source tubing sections 60, each having an inflow spike 62 on an end thereof.

If the source of surgery washing fluid 16 is a bag of surgery washing fluid, the inflow spikes 62 can be inserted into the bag of surgery washing fluid to allow the surgery washing fluid to flow to the inflow cassette 20. While not shown, the inflow spikes 62 can have removable caps thereon for preventing the inflow spikes 62 from cutting or penetrating items other than the source of surgery washing fluid 16 when the inflow spikes 62 are not connected to the source of surgery washing fluid 16 and to keep the inflow spikes 62 sterile until the inflow spikes 62 are inserted into the source of washing fluid 16. Each source tubing section 60 of the input tubing 18 can have a pinch clamp 64 thereon. In use, one of the pinch clamps 64 can be closed to prevent flow through the source tubing section 60. When the pinch clamp 64 is closed, the source of surgery washing fluid 16 connected to the source tubing section 60 with the closed pinch clamp 64 can be changed when the source of surgery washing fluid 16 is empty. The source of surgery washing fluid 16 is changed by removing the inflow spike 62 therefrom. The inflow spike 62 is then inserted into a new source of surgery washing fluid 16 and the pinch clamp 64 can be opened to allow the surgery washing fluid from the new source of surgery washing fluid 16 to flow to the inflow cassette 20 through the source tubing section 60, the Y-connector 58 and the cassette connection portion 56, which is connected to the inflow cassette 20. With the Y-connector 58, two sources of surgery washing fluid 16 can be connected to the inflow cassette 20 such that a constant flow of surgery washing fluid can be provided to the inflow cassette 20 even when one of the sources of surgery washing fluid 16 is being changed. It is contemplated that the input tubing 18 could comprise a single tube with the inflow spike 62 or other connection device on an end thereof.

In the illustrated embodiment, the inflow cassette 20 (FIGS. 2-6) is connected to the cassette connection portion 56 of the input tubing 18 to receive the surgery washing fluid from the source of surgery washing fluid 16. As illustrated in FIG. 2, the inflow cassette 20 is substantially horseshoe shaped with an enlarged arched section 78 and a pair of legs 80 having inwardly facing feet 82 at an end thereof. A periphery of the arched section 78 and the legs 80 define a substantially arched edge 86. The legs 80 define an arched cutout 84 therebetween. Peristaltic tubing 70 extends from the inwardly facing feet 82 along a periphery of the arched cutout 84. As discussed in more detail below, the inflow cassette 20 is connected to the pump 14 by inserting the inwardly facing feet 82 of the inflow cassette 20 into the pump 14 first and pushing the enlarged arched section 78 until the inflow cassette 20 is fully engaged with the pump 14. Therefore, the inwardly facing feet 82 of the inflow cassette 20 define the insertion side thereof and a side of the inflow cassette 20 opposite the inwardly facing feet 82 defines the extraction side thereof.

Figure 5:
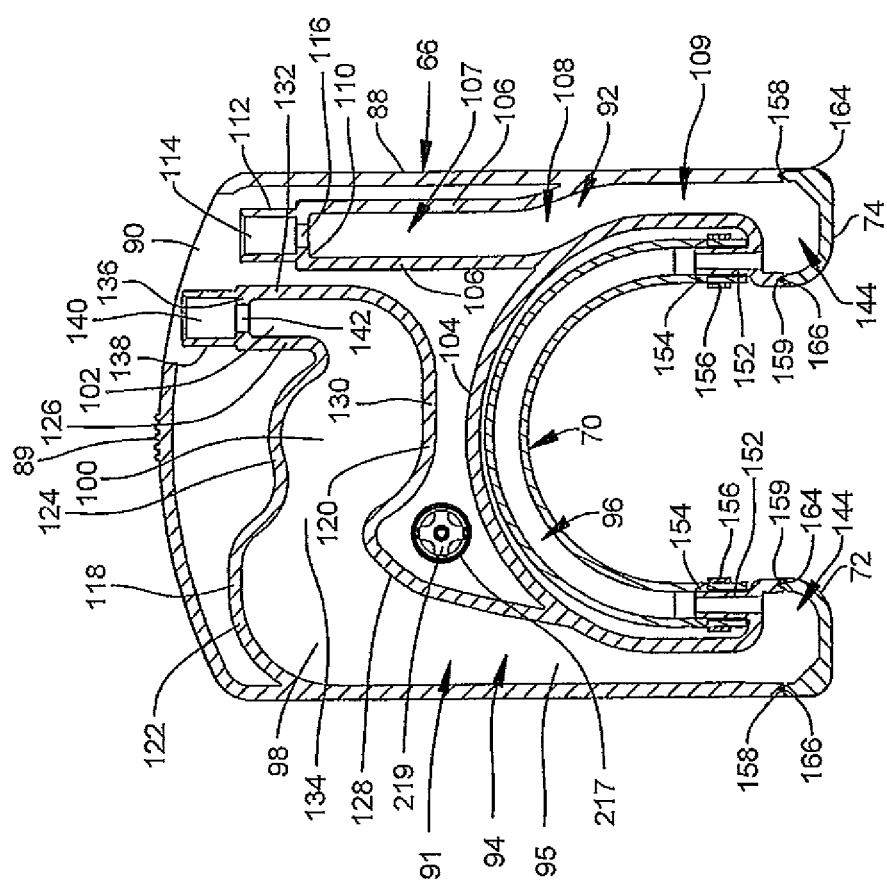
FIG. 5 is a top cross-sectional view of the inflow cassette of the present invention.

The illustrated inflow cassette 20 includes an interior fluid flow path 91 therethrough accepting the surgery washing fluid from the input tubing 18 and forcing the surgery washing fluid into the inflow tube 22. As best illustrated in FIG. 5, the interior fluid flow path 91 includes an ingress path section 92 receiving the surgery washing fluid entering the inflow cassette 20 and an egress path section 94. A peristaltic tube path section 96 located in the peristaltic tubing 70 (as illustrated in FIG. 2) is positioned between the ingress path section 92 and the egress path section 94 of the interior fluid flow path 91. The pump 14 pushes the surgery washing fluid through the peristaltic tube path section 96 from the ingress path section 92 to the egress path section 94. As the surgery washing fluid is pushed through the egress path section 94, the surgery washing fluid passes through an entry area 95, a damping chamber area 98 for damping pressure fluctuations of the surgery washing fluid, a pressure sensing area 100 for sensing a pressure of the surgery washing fluid, and then an exit area 102. Once the surgery washing fluid reaches the exit area 102 of the egress path section 94, the surgery washing fluid enters the inflow tube 22.

The illustrated inflow cassette 20 includes a top frame 66, a bottom plate 68, the peristaltic tubing 70, a left cap 72 and a right cap 74, which define the interior fluid flow path 91 through the inflow cassette 20 for accepting the surgery washing fluid from the input tubing 18 and forcing the surgery washing fluid into the inflow tube 22. The top frame 66 and the bottom plate 68 of the inflow cassette 20 are connected together to form a majority of the interior fluid flow path 91, with the peristaltic tubing 70, the left cap 72 and the right cap 74 being connected to the connected top frame 66 and bottom plate 68 to complete the interior fluid flow path 91. The top frame 66, the bottom plate 68, the left cap 72 and the right cap 74 can be made of any material (e.g., plastic injection molded parts) and can be connected in any manner (e.g., ultrasonic welding).

In the illustrated example, the top frame 66 (FIGS. 3 and 4) of the inflow cassette 20 includes a top plate 76 forming a top surface of the inflow cassette 20 and an interior top surface of the interior fluid flow path 91. The top frame 66 also includes a plurality of side walls forming side surfaces of the interior fluid flow path 91 through the inflow cassette 20. An interrupted U-shaped outer side wall 88 depends downwardly from the top plate 76 and defines the substantially arched edge 86 of the inflow cassette 20. The interrupted U-shaped outer side wall 88 can include ridges 89 on an exterior face thereof for assisting in pushing the inflow cassette 20 into the pump 14. A transition between the top plate 76 and the interrupted U-shaped outer side wall 88 is illustrated as being smooth and curved, but could have any configuration. A U-shaped inner wall 104 depends downwardly from the top plate 76 and defines the arched cutout 84 of the inflow cassette 20. A transition between the top plate 76 and the U-shaped inner wall 104 is also illustrated as being smooth and curved, but could have any configuration.

A parallel pair of ingress path section side walls 106 define side surfaces of a first area 107 of the ingress path section 92. As illustrated in FIG. 5, the pair of ingress path section side walls 106 intersect the interrupted U-shaped outer side wall 88 and the U-shaped inner wall 104 at a transition area 108, with the interrupted U-shaped outer side wall 88 and the U-shaped inner wall 104 defining a second area 109 of the ingress path section 92 after the transition area 108. A front end of the first area 107 of the ingress path section 92 defined by the ingress path section side walls 106 is bounded by a front ingress wall 110 having an inverted U-shaped ingress tube connection member 112 connected thereto. The inverted U-shaped ingress tube connection member 112 has a central aperture 114 configured to receive the input tubing 18 therein for connecting the input tubing 18 to the inflow cassette 20. The input tubing 18 can be connected to the inverted U-shaped ingress tube connection member 112 in any manner (e.g., ultrasonic welding, adhesive, interlocking mechanical connections, etc.) The interrupted U-shaped outer side wall 88 has an open area 90 at the extraction side of the inflow cassette 20 for receipt of the input tubing 18 to allow the input tubing 18 to be inserted into the central aperture 114 of the inverted U-shaped ingress tube connection member 112. The top frame 66 can include a hole 201 above the intersection of the input tubing 18 and the inverted U-shaped ingress tube connection member 112 for allowing access to the intersection for connecting the input tubing 18 to the inverted U-shaped ingress tube connection member 112. The front ingress wall 110 includes a centrally located hole 116 for allowing the surgery washing fluid to enter the interior fluid flow path 91 from the input tubing 18.

In the illustrated example, the interrupted U-shaped outer side wall 88 and the U-shaped inner wall 104 form side surfaces of the entry area 95 of the egress path section 94. The interrupted U-shaped outer side wall 88 also defines a side surface of a first portion of the damping chamber area 98 of the egress path section 94. A first egress section sidewall 118 defines side surfaces of a second portion of the damping chamber area 98, the pressure sensing area 100 and the exit area 102 of the egress path section 94. The first egress section sidewall 118 extends from the interrupted U-shaped outer side wall 88 adjacent the extraction side of the inflow cassette 20. The first egress section sidewall 118 has a first arcuate section 122 defining the second portion of the damping chamber area 98, a second arcuate section 124 defining a side of the pressure sensing area 100 and a straight section 126 defining a side of the exit area 102. A second egress section sidewall 120 also defines side surfaces of the damping chamber area 98, the pressure sensing area 100 and the exit area 102 of the egress path section 94. The second egress section sidewall 120 extends from the U-shaped inner wall 104 after the entry area 94 of the egress path section 94. The second egress section sidewall 120 has a first arcuate section 128 defining a side of the damping chamber area 98, a second arcuate section 130 defining a side of the pressure sensing area 100 and a straight section 132 defining a side of the exit area 102. The first egress section sidewall 118 and the second egress section sidewall 120 define a constriction 134 between the damping chamber area 98 and the pressure sensing area 100.

The illustrated inflow cassette 20 includes the exit area 102 that is bounded by a front egress wall 136 having an inverted U-shaped egress tube connection member 138 connected thereto. The inverted U-shaped egress tube connection member 138 has a central aperture 140 configured to receive the inflow tube 22 therein for connecting the inflow tube 22 to the inflow cassette 20. The inflow tube 22 can be connected to the inverted U-shaped egress tube connection member 138 in any manner (e.g., ultrasonic welding, adhesive, interlocking mechanical connections, etc.) The open area 90 of the interrupted U-shaped outer side wall 88 allows for receipt of the inflow tube 22 to be inserted into the central aperture 140 of the inverted U-shaped egress tube connection member 138. The top frame 66 can include a hole 199 above the intersection of the inflow tube 22 and the inverted U-shaped egress tube connection member 138 for allowing access to the intersection for connecting the inflow tube 22 to the inverted U-shaped egress tube connection member 138. The front egress wall 136 includes a centrally located hole 142 for allowing the surgery washing fluid to exit the interior fluid flow path 91 into the inflow tube 22.

Figure 3:
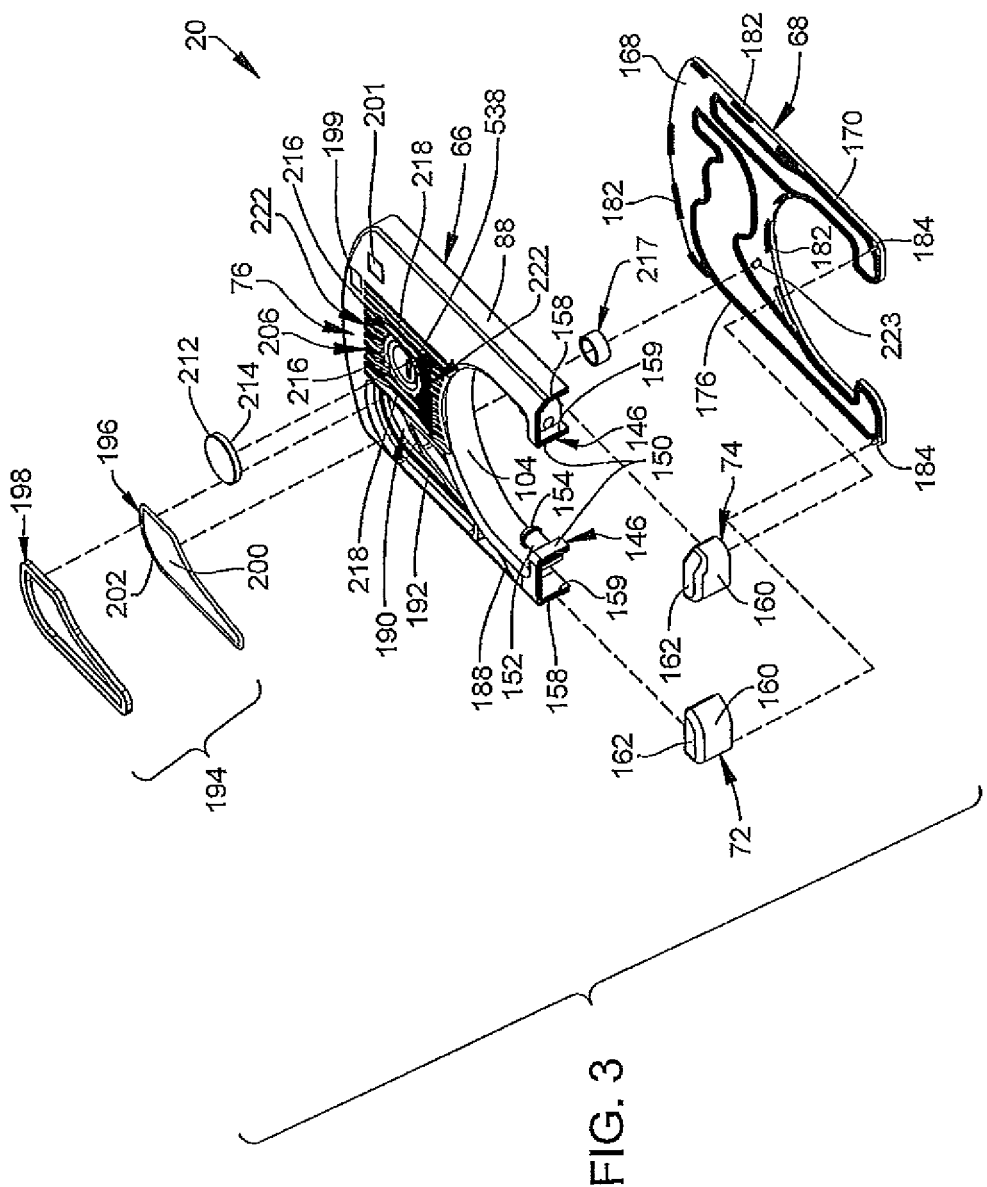
FIG. 3 is an exploded top perspective view of an inflow cassette of the present invention without peristaltic tubing.

In the illustrated example, the inflow cassette 20 includes peristaltic junction areas 144 at the end of the ingress path section 92 and at the beginning of the egress path section 94. Each peristaltic junction area 144 includes an L-shaped side wall 146 depending downward from the top plate 76 of the top frame 66 defining a portion of the inwardly facing feet 82 of the inflow cassette 20. Each L-shaped side wall 146 includes a long section 148 facing the arched cutout 84 of the inflow cassette 10 and a short section 150 facing the short section 150 on the other L-shaped side wall 146. The long sections 148 each have an outwardly facing cylinder 152 with a ramped prong 154 about an end thereof. As illustrated in FIG. 5, ends of the peristaltic tubing 70 are inserted over the outwardly facing cylinders 152 and locking cuffs 156 are inserted over the ends of the peristaltic tubing 70 between the ramped prong 154 and the long section 148 of the L-shaped side wall 146 to lock the ends of the peristaltic tubing 70 to the L-shaped side walls 146. As illustrated in FIG. 3, an edge of the short section 150 of the L-shaped side wall 146, an edge of the top plate 76 and an edge of the interrupted U-shaped outer side wall 88 of the top frame 66 at each peristaltic junction areas 144 defines a substantially U-shaped edge 158 having a substantially U-shaped recess 159. The substantially U-shaped edges 158 are configured to engage the left cap 72 and the right cap 74.

The illustrated left cap 72 and right cap 74 also define a portion of the peristaltic junction areas 144. Each of the left cap 72 and the right cap 74 includes a U-shaped end wall 160 and a top wall 162. Two end edges of the U-shaped end wall 160 and the top wall 162 define a U-shaped side edge 164 having a U-shaped projection 166. Each of the left cap 72 and the right cap 74 is connected to the top frame 66 by inserting the U-shaped projection 166 into the U-shaped recess 159 in the U-shaped edge 158 at each peristaltic junction area 144 until the U-shaped side edge 164 of the left cap 72 and the right cap 74 abuts the U-shaped edge 158 of the top frame 66. The left cap 72 and the right cap 74 can be securely connected to the top frame 66 by an interference fit between the U-shaped projection 166 of the left cap 72 and the right cap 74 and the U-shaped recess 159 in the U-shaped edge 158, by applying an adhesive between the U-shaped side edge 164 and the U-shaped edge 158 of the top frame 66, by welding (e.g., ultrasonic) the left cap 72 and the right cap 74 to the top frame 66 and/or any other connection method. The U-shaped end wall 160 of each of the left cap 72 and the right cap 74 also define a bottom U-shaped edge configured to engage the bottom plate 68 of the inflow cassette 20. While the top frame 66, the left cap 72 and the right cap 74 are illustrated as being three separate parts, it is contemplated that the top frame 66, the left cap 72 and the right cap 74 could be a single integral part or be formed by any number of parts.

In the illustrated example, the bottom plate 68 of the inflow cassette 20 is engaged with the top frame 66, the left cap 72 and the right cap 74 to complete the interior fluid flow path 91 through the inflow cassette 20. The bottom plate 68 has the same outer periphery as a combination of the top frame 66, the left cap 72 and the right cap 74. The bottom plate 68 includes a bottom panel 168 having an ingress path ridge 170 corresponding to the boundary of the ingress path section 92 of the interior fluid flow path 91. The ingress path ridge 170 is configured to be inserted into a corresponding ingress path channel 172 in a bottom edge 174 defined by a bottom of the front ingress wall 110, bottoms of the ingress path section side walls 106, bottoms of the U-shaped inner wall 104 and the interrupted U-shaped outer side wall 88 of the top frame 66 defining sides of the second area 109 of the ingress path section 92, and the bottom U-shaped edge of the right cap 74. The bottom plate 68 also includes an egress path ridge 176 corresponding to the boundary of the egress path section 94 of the interior fluid flow path 91. The egress path ridge 176 is configured to be inserted into a corresponding egress path channel 178 in a bottom edge 180 defined by the bottom U-shaped edge of the left cap 72, bottoms of the U-shaped inner wall 104 and the interrupted U-shaped outer side wall 88 of the top frame 66 defining sides of the entry area 95 of the egress path section 94, a bottom of the first egress section sidewall 118, a bottom of the second egress section sidewall 120 and a bottom of the front egress wall 136. The bottom plate 68 also includes a plurality of short connection ridges 182 configured to be inserted into corresponding short connection channels 183 in the bottom of the U-shaped inner wall 104 and the interrupted U-shaped outer side wall 88 of the top frame 66. Moreover, the bottom plate 68 can include a pair of posts 184 adjacent the peristaltic junction areas 144 of the inflow cassette 20 for insertion into corresponding holes 186 in the bottom U-shaped edge of the left cap 72 and the right cap 74. The bottom plate 68 can be connected to the top frame 66, the left cap 72 and the right cap 74 by an interference fit between the ingress path ridge 170 and the ingress path channel 172, the egress path ridge 176 and the egress path channel 178, the short connection ridges 182 and the short connection channels 183, and the posts 184 and the holes 186, by adhesive, by welding (e.g., ultrasonic) and/or by other connection methods.

The illustrated inflow cassette 20 is configured to have the surgery washing fluid suctioned out of the source of surgery washing fluid 16, pushed through the inflow cassette 20 and pushed through the inflow tube 22 into the body cavity 12. As the surgery washing fluid enters the inflow cassette 20, the surgery washing fluid passes through the centrally located hole 116 in the front ingress wall 110 and then through the first area 107, the transition area 108 and the second area 109 of the ingress path section 92. Once the surgery washing fluid reaches the peristaltic junction area 144, the surgery washing fluid enters the outwardly facing cylinder 152 holding the peristaltic tubing 70 adjacent the ingress path section 92 and then into the peristaltic tubing 70. As discussed in more detail below, the peristaltic tubing 70 is pinched moving in a direction from the ingress path section 92 towards the egress path section 94 of the interior fluid flow path 91. As the peristaltic tubing 70 is pinched, the surgery washing fluid therein is forced towards the egress path section 94. Moreover, a vacuum is created in the peristaltic tubing 70 behind the portion of the peristaltic tubing 70 being pinched, thereby suctioning the surgery washing fluid out of the source of surgery washing fluid 16 and into the inflow cassette 20.

In the illustrated example, after the surgery washing fluid exits the peristaltic tubing 70 in the inflow cassette 20, the surgery washing fluid enters the egress path section 94 of the interior fluid flow path 91. The washing fluid then sequentially passes through the entry area 95, the damping chamber area 98, the pressure sensing area 100 and the exit area 102 of the egress path section 94. As illustrated in FIG. 3, the top plate 76 of the top frame 66 includes a downwardly depending ramp 188 extending into the egress path section 94 between the entry area 95 and the damping chamber area 98 to lessen the distance between the bottom panel 168 of the bottom plate 68 and the top plate 76 of the top frame 66 of the inflow cassette 20. The downwardly depending ramp 188 constricts the area of the egress path section 94 in order to help condition the flow of fluid prior to entering the damping chamber area 98. The ramp 188 can reduce turbulence and recirculation caused by the redirection of the fluid as the fluid comes out of the peristaltic tubing 70. The distance between the bottom panel 168 of the bottom plate 68 and the top plate 76 of the top frame 66 of the inflow cassette 20 remains at the smaller distance in the damping chamber area 98, the pressure sensing area 100 and the exit area 102.

The pressure fluctuations of the surgery washing fluid passing through the egress path section 94 of the interior fluid flow path 91 are reduced or dampened in the damping chamber area 98. As illustrated in FIG. 3, the top plate 76 of the top frame 66 has a cut-out 190 over the damping chamber area 98. The cut-out 190 has a ledge 192 about a periphery thereof slightly below a level of the top plate 76. A damping assembly 194 is positioned over the damping chamber area 98. The damping assembly 194 includes a damping chamber frame 196 and a damping chamber flexible membrane 198. The damping chamber frame 196 has substantially the same periphery as the cut-out 190 in the top plate 76. The damping chamber flexible membrane 198 includes a center damping portion section 200 and a peripheral bulge 202. An underside of the damping chamber frame 196 includes a trough 204 for accepting the peripheral bulge 202 of the damping chamber flexible membrane 198. The damping chamber flexible membrane 198 is connected to the top frame 66 by sandwiching the damping chamber flexible membrane 198 between the damping chamber frame 196 and the ledge 192 about the periphery of the cut-out 190. The damping chamber frame 196 can be connected to the top frame 66 by an interference fit, by adhesive, by welding and/or by other connection methods.

In the illustrated example, the damping chamber flexible membrane 198 expands and contracts due to the pressure pulses generated in the surgery washing fluid passing through the peristaltic tubing 70. The compliance of the damping chamber flexible membrane 198 reduces an amplitude of the pressure pulses causing a more uniform flow entering into both the pressure sensing area 100 and the body cavity 12 with less pressure pulsing. The damping chamber flexible membrane 198 also helps produce a more uniform pressure wave that is easier to process (e.g., it can be easier for the pump 14 to measure the pressure of the surgery washing fluid in the pressure sensing area 100 because, since the pressure fluctuations are reduced, a sample time used to estimate the fluid pressure is reduced). The damping chamber flexible membrane 198 can be made of any non-permeable, flexible or elastic material (e.g., silicone).

After the surgery washing fluid passes the damping chamber area 98, a pressure of the surgery washing fluid is measured in the pressure sensing area 100. The top plate 76 of the top frame 66 has a rectangular recess 206 above the pressure sensing area 100. A circular seat 208 is located in a center of the rectangular recess 206, with the circular seat 208 including an access slot 538 leading to the pressure sensing area 100 from outside the inflow cassette 20 and a peripheral channel 210 adjacent an edge of the circular seat 208. A disc-shaped pressure sensing membrane 212 covers the circular seat 208, with the disc-shaped pressure sensing membrane 212 having a circular projection 214 extending downwardly from a margin thereof. The circular projection 214 sits within the peripheral channel 210 in the circular seat 208 to connect the disc-shaped pressure sensing membrane 212 to the top frame 66. The disc-shaped pressure sensing membrane 212 can be connected to the top frame 66 with an interference fit, adhesive, welding and/or any other connection scheme. A plurality of parallel guide strips 216 span the rectangular recess 206 except for the area occupied by the circular seat 208. The parallel guide strips 216 are parallel to a direction of insertion of the inflow cassette 20 into the pump 14. Two of the parallel guide strips 216 on either side of the circular seat 208 include thinner center sections 218. As discussed in more detail below, the two parallel guide strips 216 with the thinner center sections 218 are used to align the disc-shaped pressure sensing membrane 212 with a pressure sensor 492 in the pump 14. Most of the remaining parallel guide strips 216 include a trapezoidal cut-out, with a longer side of the trapezoidal cut-out being located at a top of the parallel guide strips 216. The trapezoidal cut-out is also used to align the disc-shaped pressure sensing membrane 212 with the pressure sensor in the pump 14. The trapezoidal cut-outs define a pair of ramps 222 on either side on the disc-shaped pressure sensing membrane 212 in a direction parallel with the parallel guide strips 216.

In the illustrated example, after the surgery washing fluid leaves the pressure sensing area 100, the surgery washing fluid enters the exit area 102 of the interior fluid flow path 91, enters the hole 142 in the front egress wall 136 and then enters the inflow tube 22. In the illustrated example, the inflow tube 22 is bonded or fixedly connected to the inverted U-shaped egress tube connection member 138 at the exit area 102 of the interior fluid flow path 91. The inflow cassette 20 can be used with a single person during a single surgical procedure. A distal end 224 of the inflow tube 22 can include a luer lock 226 (e.g., male luer lock 226) connection or any other connection for connecting the inflow tube 22 to the inflow cannula 24. It is contemplated that the inflow tube 22 can include a pinch clamp 64 thereon for preventing fluid flow through the inflow tube 22. It is also contemplated that the inflow tube 22 could be directly inserted into the body cavity 12.

Figure 7:
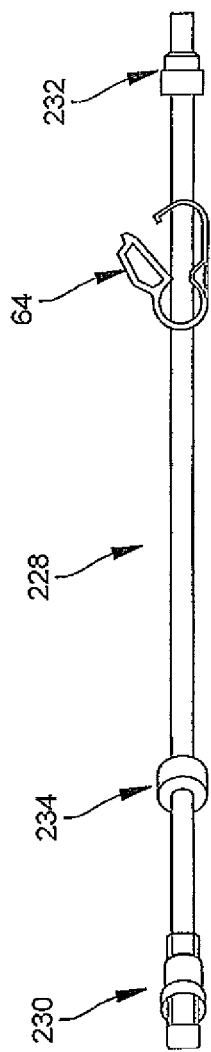
FIG. 7 is a side view of an auxiliary tube of the present invention.

The illustrated inflow cassette 20 can be used with a single person during a single surgical procedure as discussed above or can be used for a number of surgical procedures (being changed every certain number of hours (e.g., 24 hours)). In the latter situation (i.e., use for a number of surgical procedures), an auxiliary tube 228 (FIG. 7) can be located between the inflow tube 22 and the inflow cannula 24. The auxiliary tube 228 includes an entry side luer lock 230 (or other connection member) that is configured to mate with the luer lock 226 (or other connection member) on the inflow tube 22 and an exit side luer lock 232 (or other connection member) configured to mate with a luer lock (or other connection member) (not shown) on the inflow cannula 24. The auxiliary tube 228 includes a one-way check valve 234 so that fluid can never flow from the patient into the inflow cassette 20. It is contemplated that the entry side luer lock 230 and the exit side luer lock 232 are opposite connections in order to ensure that the auxiliary tube 228 is position in the right direction (i.e., positioned such that the surgery washing fluid can pass through the one-way check valve 234 in a path from the inflow cassette 20 to the inflow cannula 24). The auxiliary tube 228 can also include a pinch clamp 64 thereon for preventing fluid flow therethrough.

Figure 4:
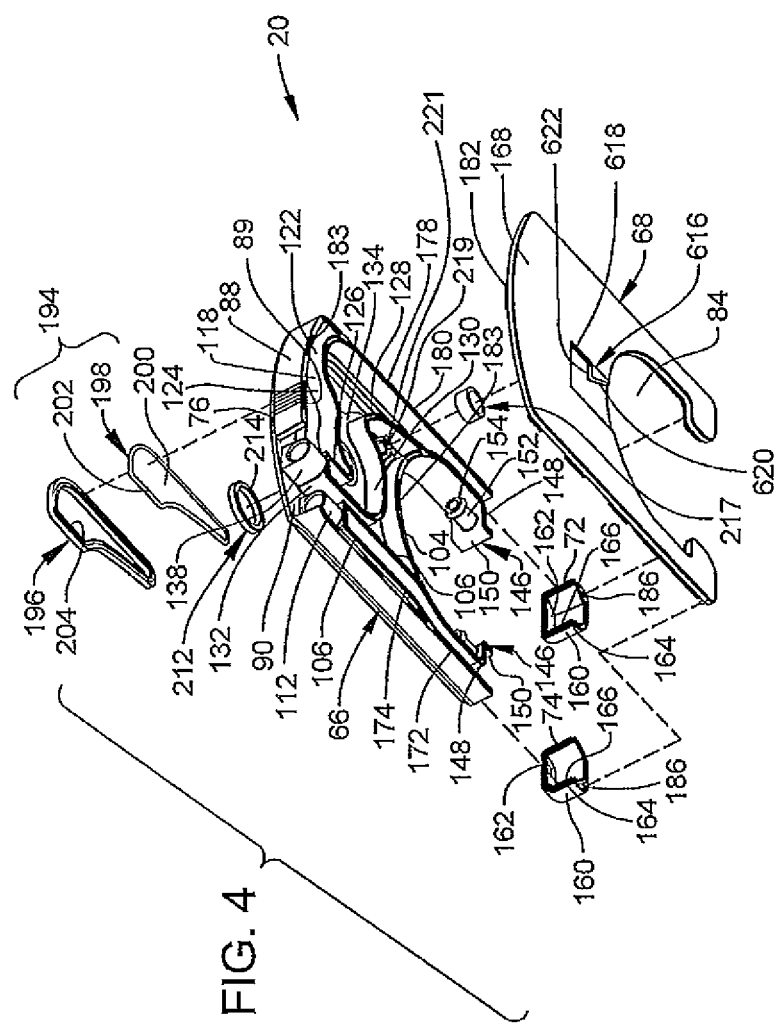
FIG. 4 is an exploded bottom perspective view of the inflow cassette of the present invention without peristaltic tubing.

In the illustrated example, the inflow cassette 20 could include an RF chip 217 for communicating information to the pump 14 once inserted into the pump 14. The RF chip 217 could have any configuration and could be located anywhere on or within the inflow cassette 20. In the illustrated example, the RF chip 217 is in the form of a cylinder located within the inflow cassette 20. As illustrated in FIG. 4, the top plate 76 of the top frame 66 includes a pronged tube 219 extending downwardly therefrom between the constriction 134 between the damping chamber area 98 and the pressure sensing area 100 of the interior fluid flow path 91 and the U-shaped inner wall 104. The RF chip 217 fits securely over the pronged tube 219. The pronged tube 219 can include an aperture 221 in a free end thereof that is configured to accept a pin 223 extending upwardly from the bottom panel 168 of the bottom plate 68 for assisting in aligning the bottom plate 68 with the top frame 66. The RF chip 217 is configured to include information including properties of the inflow cassette tubing assembly 54. For example, the RF chip 217 can include information related to properties of the inflow tube 22, the input tubing 18 and the peristaltic tubing 70 (e.g., material, size, pressure-loss characteristics, loss coefficient of the one-way check valve 234 of the auxiliary tube 228, etc.) to allow the control system to determine the flow rate of surgery washing fluid to the body cavity 12.

Figure 8:
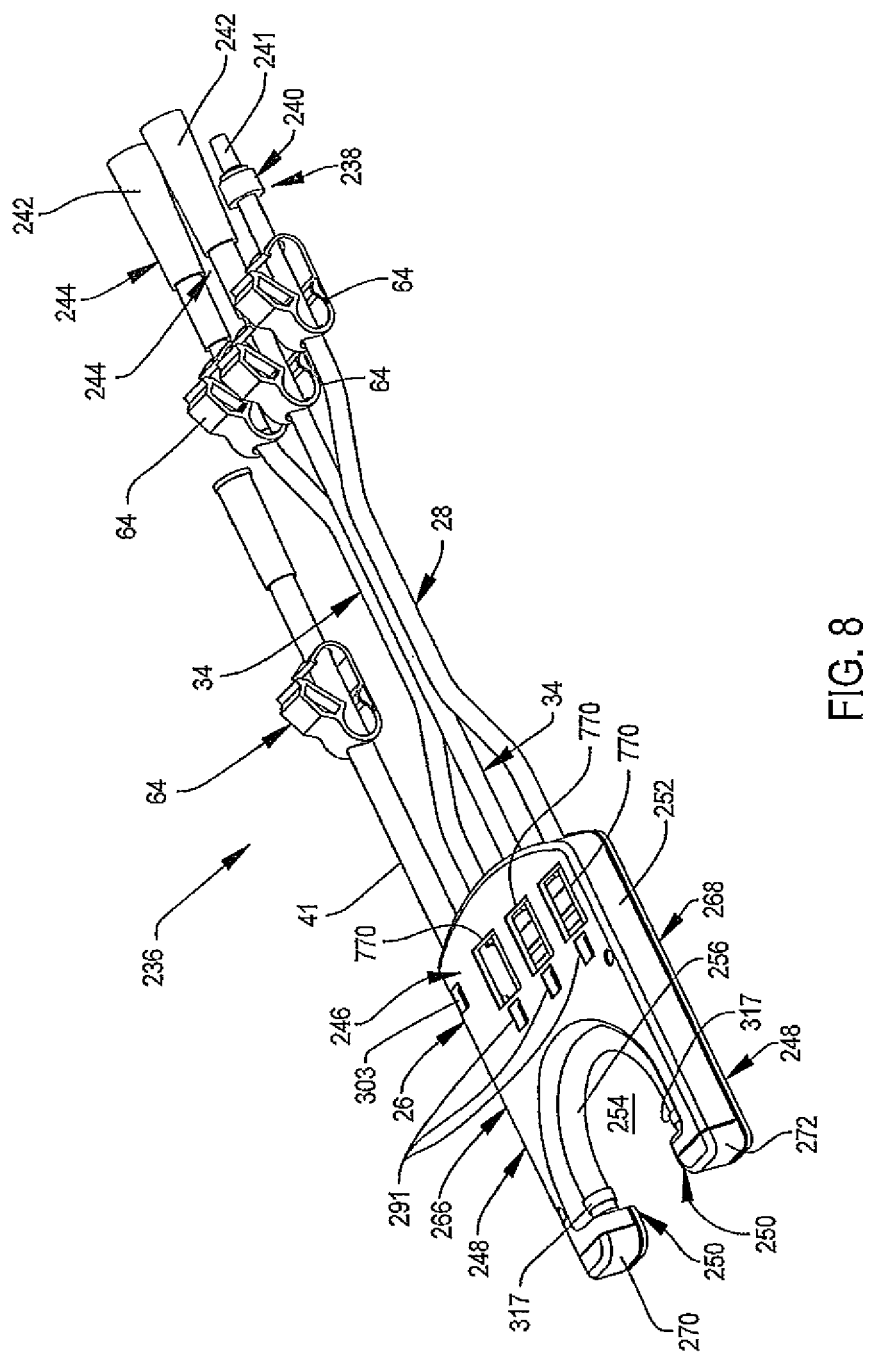
FIG. 8 is a perspective view of an outflow cassette tubing assembly of the present invention.

FIG. 8 illustrates an outflow cassette tubing assembly 236 for suctioning the waste fluid out of the body cavity 12 and to push the waste fluid into the waste receptacle 40. The outflow cassette tubing assembly 236 includes the outflow tube 28, the device suction tubing 34, the outflow cassette 26 and the waste tubing 41. As explained in more detail below, the outflow cassette 26 is inserted into the pump 14 to suction the waste fluid from the body cavity 12 and to push the waste fluid through the outflow cassette 26. It is further contemplated that the outflow tube 28 could be directly inserted into the body cavity 12, in which case the outflow tube 28 would not include any connection on an end thereof.

In the illustrated example, the outflow tube 28 is connected to the outflow cannula 30 and the outflow cassette 26. The outflow tube 28 can be made of any tubing material and can be connected to the outflow cannula 30 in any manner. In the illustrated embodiment, a distal end 238 of the outflow tube 28 includes a luer lock 240 (e.g., male luer lock 240) or any other connection for connecting the outflow tube 28 to the outflow cannula 30. In FIG. 8, the luer lock 240 has a luer cap 241 thereon. It is contemplated that the outflow tube 28 can include a pinch clamp 64 thereon for preventing fluid flow through the outflow tube 28.

Each device suction tubing 34 is configured to be connected to a surgery device 32 and the outflow cassette 26. Each device suction tubing 34 includes a suction fitting 242 on a distal end 244 thereof for connecting the device suction tubing 34 to one of the surgery devices 32. Each device suction tubing 34 can be made of any tubing material and can be connected to the surgery devices 32 in any manner. Furthermore, it is contemplated that each suction fitting 242 and each device suction tubing 34 can be color coded and/or labeled for use with the appropriate surgery device 32. It is also contemplated that each device suction tubing 34 can include a pinch clamp 64 thereon for preventing fluid flow through the device suction tubing 34. The outflow tube 28 and each of the device suction tubing 34 can initially be bonded together (as illustrated in FIG. 8), but can be able to be pulled apart if desired.

In the illustrated embodiment, the outflow cassette 26 (FIGS. 8-11) is connected to the outflow tube 28 and the device suction tubing 34 to suction the waste fluid from the body cavity 12. As illustrated in FIG. 8, the outflow cassette 26 has substantially the same periphery as the inflow cassette 20. Therefore, the outflow cassette 26 is substantially horseshoe shaped with an enlarged arched section 246 and a pair of legs 248 having inwardly facing feet 250 at an end thereof. A periphery of the arched section 246 and the legs 248 define a substantially arched edge 252. The legs 248 define an arched cutout 254 therebetween. Peristaltic tubing 256 extends from the inwardly facing feet 250 along a periphery of the arched cutout 254. As discussed in more detail below, the outflow cassette 26 is connected to the pump 14 by inserting the inwardly facing feet 250 of the outflow cassette 26 into the pump 14 first and pushing the enlarged arched section 246 until the outflow cassette 26 is fully engaged with the pump 14. Therefore, the inwardly facing feet 250 of the outflow cassette 26 define the insertion side thereof and a side of the outflow cassette 26 opposite the inwardly facing feet 250 defines the extraction side thereof.

Figure 11:
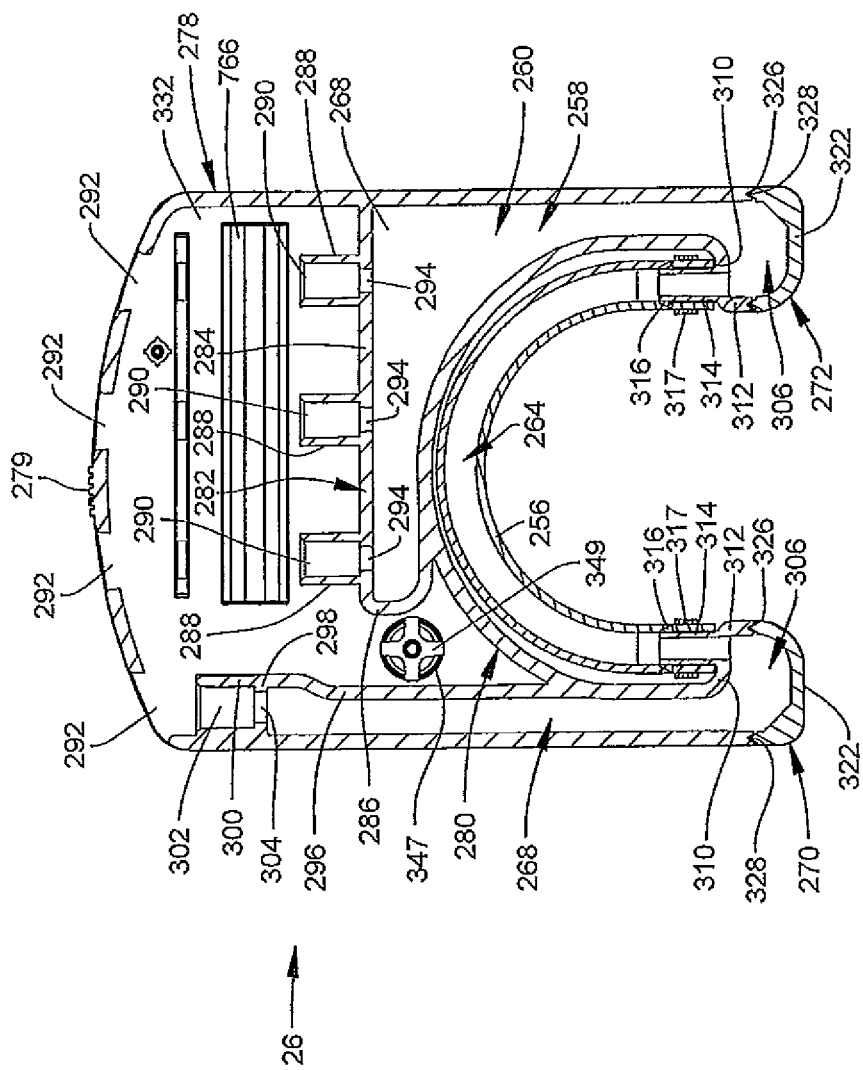
FIG. 11 is a top cross-sectional view of the outflow cassette of the present invention.

The illustrated outflow cassette 26 includes an interior fluid flow path 258 therethrough accepting the waste fluid from the outflow tube 28 and the device suction tubing 34 and forcing the waste fluid into the waste tubing 41. As best illustrated in FIG. 11, the interior fluid flow path 258 includes an ingress path section 260 receiving the waste fluid entering the outflow cassette 26 and an egress path section 262. A peristaltic tube path section 264 located in the peristaltic tubing 256 is positioned between the ingress path section 260 and the egress path section 262 of the interior fluid flow path 258. The pump 14 pushes the waste fluid through the peristaltic tube path section 264 from the ingress path section 260 to the egress path section 262. Once the waste fluid exits the egress path section 262, the waste fluid enters the waste tubing 41.

The illustrated outflow cassette 26 includes a top frame 266, a bottom plate 268, the peristaltic tubing 256, a left cap 270 and a right cap 272, which define the interior fluid flow path 258 through the outflow cassette 26 for accepting the waste fluid from the outflow tube 28 and the device suction tubing 34. The top frame 266 and the bottom plate 268 of the outflow cassette 26 are connected together to form a majority of the interior fluid flow path 258, with the peristaltic tubing 256, the left cap 270 and the right cap 272 being connected to the connected top frame 266 and bottom plate 268 to complete the interior fluid flow path 258. The top frame 266, the bottom plate 268, the left cap 270 and the right cap 272 can be made of any material (e.g., plastic injection molded parts) and can be connected in any manner (e.g., ultrasonic welding).

In the illustrated example, the top frame 266 (FIGS. 9 and 10) of the outflow cassette 26 includes a top plate 276 forming a top surface of the outflow cassette 26 and an interior top surface of the interior fluid flow path 258. The top frame 266 also includes a plurality of side walls forming side surfaces of the interior fluid flow path 258 through the outflow cassette 26. An interrupted U-shaped outer side wall 278 depends downwardly from the top plate 276 and defines the substantially arched edge 252 of the outflow cassette 26.

The interrupted U-shaped outer side wall 278 can include ridges 279 on an exterior face thereof for assisting in pushing the outflow cassette 26 into the pump 14. A transition between the top plate 276 and the interrupted U-shaped outer side wall 278 is illustrated as being smooth and curved, but could have any configuration. A U-shaped inner wall 280 depends downwardly from the top plate 276 and defines the arched cutout 254 of the outflow cassette 26. A transition between the top plate 276 and the U-shaped inner wall 280 is also illustrated as being smooth and curved, but could have any configuration.

The illustrated sides of the ingress path section 260 are defined by a portion of the interrupted U-shaped outer side wall 278, a portion of the U-shaped inner wall 280, the right cap 272 and a J-shaped entrance wall 282. The J-shaped entrance wall 282 includes a straight section 284 extending perpendicularly from an interior surface of the interrupted U-shaped outer side wall 278 and a curved section 286 that curves towards and joins the U-shaped inner wall 280. The straight section 284 of the J-shaped entrance wall 282 defines a front end of the ingress path section 260. Three inverted U-shaped ingress tube connection members 288 are connected to a front side of the straight section 284 of the J-shaped entrance wall 282. The inverted U-shaped ingress tube connection members 288 each have a central aperture 290 configured to receive the outflow tube 28 or one of the device suction tubing 34 therein for connecting the outflow tube 28 or one of the device suction tubing 34 to the outflow cassette 26. The top frame 266 can include holes 291 above the intersection of the outflow tube 28 or the device suction tubing 34 and each of the inverted U-shaped ingress tube connection members 288 for allowing access to the intersection for connecting the outflow tube 28 and the device suction tubing 34 to the inverted U-shaped ingress tube connection members 288. The outflow tube 28 and the device suction tubing 34 can be connected to the inverted U-shaped ingress tube connection members 288 in any manner (e.g., ultrasonic welding, adhesive, interlocking mechanical connections, etc.)

The illustrated interrupted U-shaped outer side wall 278 has three open areas 292 at the extraction side of the outflow cassette 26 for receipt of the outflow tube 28 and the device suction tubing 34 to allow the outflow tube 28 and the device suction tubing 34 to be inserted into the central apertures 290 of the inverted U-shaped ingress tube connection members 288. The straight section 284 of the J-shaped entrance wall 282 also includes a hole 294 aligned with each one of the open areas 292 of the inverted U-shaped ingress tube connection members 288 for allowing the waste fluid to enter the interior fluid flow path 258 from the outflow tube 28 and the device suction tubing 34. The right cap 272 also forms sides of the ingress path section 260 as discussed in more detail below.

In the illustrated example, sides of the egress path section 262 are defined by a portion of the interrupted U-shaped outer side wall 278, a portion of the U-shaped inner wall 280, the left cap 270, an inner egress side wall 296, and a front egress wall 298 having an inverted egress tube connection member 300 connected thereto. The inner egress side wall 296 extends from the U-shaped inner wall 280 and is parallel to the portion of the interrupted U-shaped outer side wall 278 defining the other wall of the portion of the egress path section 262, except for at an end of the egress path section 262, where the inner egress side wall 296 diverges slightly away from the interrupted U-shaped outer side wall 278. The inverted U-shaped egress tube connection member 300 is partially connected to the interrupted U-shaped outer side wall 278 and has a central aperture 302 configured to receive the waste tubing 41 therein for connecting the waste tubing 41 to the outflow cassette 26. The top frame 266 can include a hole 303 above the intersection of the waste tubing 41 and inverted U-shaped egress tube connection member 300 for allowing access to the intersection for connecting the waste tubing 41 to the inverted U-shaped egress tube connection member 300. The waste tubing 41 can be connected to the inverted U-shaped egress tube connection member 300 in any manner (e.g., ultrasonic welding, adhesive, interlocking mechanical connections, etc.) Another one of the open area 292 of the interrupted U-shaped outer side wall 278 allows for receipt of the waste tubing 41 to be inserted into the central aperture 302 of the inverted U-shaped egress tube connection member 300. The front egress wall 298 includes a centrally located hole 304 for allowing the waste fluid to exit the interior fluid flow path 258 into the waste tubing 41. The left cap 270 also forms sides of the egress path section 262 as discussed in more detail below.

Figure 9:
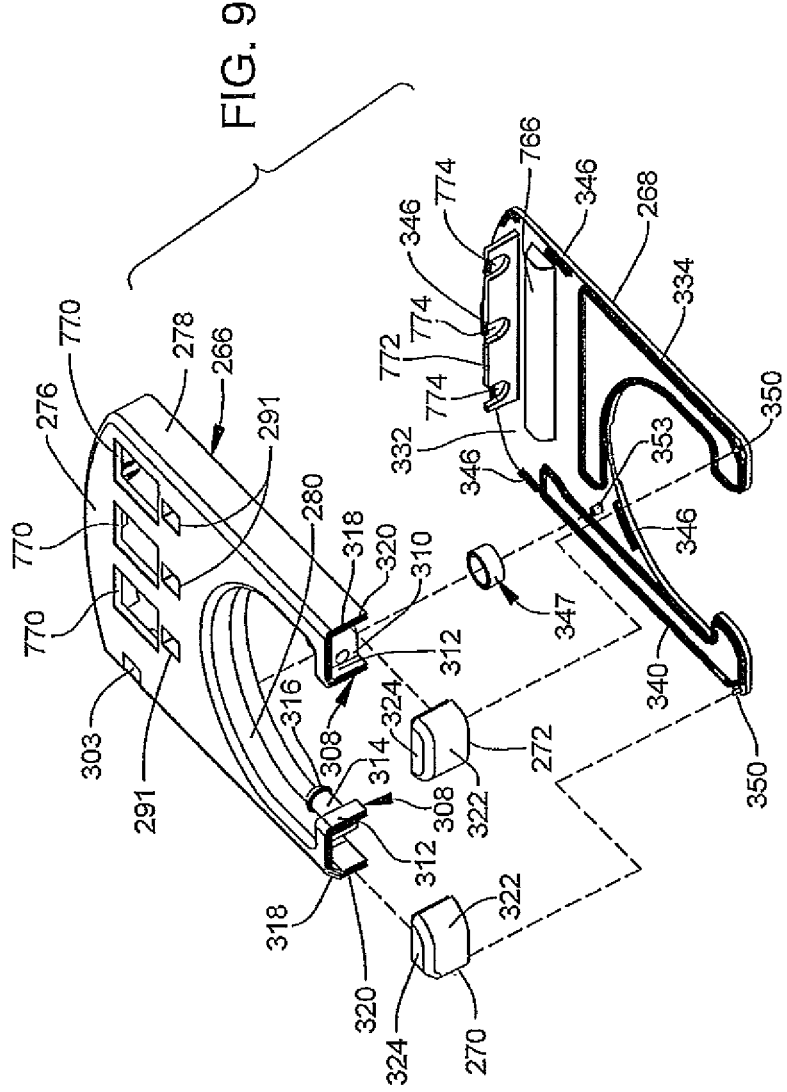
FIG. 9 is an exploded top perspective view of an outflow cassette of the present invention without peristaltic tubing.

The illustrated outflow cassette 26 includes peristaltic junction areas 306 at the end of the ingress path section 260 and at the beginning of the egress path section 262. Each peristaltic junction area 306 includes an L-shaped side wall 308 depending downward from the top plate 276 of the top frame 266, which defines a portion of the inwardly facing feet 250 of the outflow cassette 26. Each L-shaped side wall 308 includes a long section 310 facing the arched cutout 254 of the outflow cassette 26 and a short section 312, with each the short sections 312 facing the other L-shaped side wall 308. The long sections 310 each have an outwardly facing cylinder 314 with a ramped prong 316 about an end thereof. As illustrated in FIG. 11, ends of the peristaltic tubing 256 are inserted over the outwardly facing cylinders 314 and locking cuffs 317 are inserted over the ends of the peristaltic tubing 256 between the ramped prong 316 and the long section 310 of the L-shaped side wall 308 to lock the ends of the peristaltic tubing 256 to the L-shaped side walls 308. As illustrated in FIG. 9, an edge of the short section 312 of the L-shaped side wall 308, an edge of the top plate 276 and an edge of the interrupted U-shaped outer side wall 278 of the top frame 266 at each peristaltic junction areas 306 defines a substantially U-shaped edge 318 having a substantially U-shaped recess 320. The substantially U-shaped edges 318 are configured to engage the left cap 270 and the right cap 272.

The illustrated left cap 270 and right cap 272 also define a portion of the peristaltic junction areas 306. Each of the left cap 270 and the right cap 272 includes a U-shaped end wall 322 and a top wall 324. Two end edges of the U-shaped end wall 322 and the top wall 324 define a U-shaped side edge 326 having a U-shaped projection 328. Each of the left cap 270 and the right cap 272 is connected to the top frame 266 by inserting the U-shaped projection 328 into the substantially U-shaped recess 320 in the substantially U-shaped edge 318 at each peristaltic junction area 306 until the U-shaped side edge 326 of the left cap 270 and the right cap 272 abuts the substantially U-shaped edge 318 of the top frame 266. The left cap 270 and the right cap 272 can be securely connected to the top frame 266 by an interference fit between the U-shaped projection 328 of the left cap 270 and the right cap 272 and the substantially U-shaped recess 320 in the substantially U-shaped edge 318, by applying an adhesive between the U-shaped side edge 326 and the substantially U-shaped edge 318 of the top frame 266, by welding (e.g., ultrasonic) the left cap 270 and the right cap 272 to the top frame 266 and/or any other connection method. The U-shaped end wall 322 of each of the left cap 270 and the right cap 272 also define a bottom U-shaped edge 330 configured to engage the bottom plate 268 of the outflow cassette 26. While the top frame 266, the left cap 270 and the right cap 272 are illustrated as being three separate parts, it is contemplated that the top frame 266, the left cap 270 and the right cap 272 could be a single integral part or be formed by any number of parts.

In the illustrated example, the bottom plate 268 of the outflow cassette 26 is engaged with the top frame 266, the left cap 270 and the right cap 272 to complete the interior fluid flow path 258 through the outflow cassette 26. The bottom plate 268 has the same outer periphery as a combination of the top frame 266, the left cap 270 and the right cap 272. The bottom plate 268 includes a bottom panel 332 having an ingress path ridge 334 corresponding to the boundary of the ingress path section 260 of the interior fluid flow path 258. The ingress path ridge 334 is configured to be inserted into a corresponding ingress path channel 336 in a bottom edge 338 defined by a bottom of the J-shaped entrance wall 282, bottoms of the U-shaped inner wall 280 and the interrupted U-shaped outer side wall 278 of the top frame 266 defining the ingress path section 260, and the bottom U-shaped edge 330 of the right cap 272. The bottom plate 268 also includes an egress path ridge 340 corresponding to the boundary of the egress path section 262 of the interior fluid flow path 258. The egress path ridge 340 is configured to be inserted into a corresponding egress path channel 342 in a bottom edge 344 defined by the bottom U-shaped edge 330 of the left cap 270, bottoms of the U-shaped inner wall 280 and the interrupted U-shaped outer side wall 278 of the top frame 266 defining sides of the egress path section 262, a bottom of the inner egress side wall 296, and a bottom of the front egress wall 298. The bottom plate 268 also includes a plurality of short connection ridges 346 configured to be inserted into corresponding short connection channels 348 in the bottom of the U-shaped inner wall 280 and the interrupted U-shaped outer side wall 278 of the top frame 266. Moreover, the bottom plate 268 can include a pair of posts 350 adjacent the peristaltic junction areas 306 of the outflow cassette 26 for insertion into corresponding holes 352 in the bottom U-shaped edge 330 of the left cap 270 and the right cap 272. The bottom plate 268 can be connected to the top frame 266, the left cap 270 and the right cap 272 by an interference fit between the ingress path ridge 334 and the ingress path channel 336, the egress path ridge 340 and the egress path channel 342, the short connection ridges 346 and the short connection channels 348, and the posts 350 and the holes 352, by adhesive, by welding (e.g., ultrasonic) and/or by other connection methods.

The illustrated outflow cassette 26 is configured to have the waste fluid suctioned out of the body cavity 12, pushed through the outflow cassette 26 and pushed through the waste tubing 41 into the waste receptacle 40. As the waste fluid enters the outflow cassette 26, the waste fluid passes through one of the holes 294 in the straight section 284 of the J-shaped entrance wall 282 and then through the ingress path section 260. Once the waste fluid reaches the peristaltic junction area 306, the waste fluid enters the outwardly facing cylinder 314 holding the peristaltic tubing 256 adjacent the ingress path section 260 and then into the peristaltic tubing 256. As discussed in more detail below, the peristaltic tubing 256 is pinched moving in a direction from the ingress path section 260 towards the egress path section 262 of the interior fluid flow path 258. As the peristaltic tubing 256 is pinched, the waste fluid therein is forced towards the egress path section 262. Moreover, a vacuum is created in the peristaltic tubing 256 behind the portion of the peristaltic tubing 256 being pinched, thereby suctioning the waste fluid out of the body cavity 12 and into the outflow cassette 26.

In the illustrated example, after the waste fluid exits the peristaltic tubing 256 in the outflow cassette 26, the waste fluid enters the egress path section 262 of the interior fluid flow path 258. As the waste fluid leaves the egress path section 262, the waste fluid enters the centrally located hole 304 in the front egress wall 298 and then enters the waste tubing 41. In the illustrated example, the waste tubing 41 is bonded or fixedly connected to the inverted U-shaped egress tube connection member 300. It is contemplated that the waste tubing 41 can include a pinch clamp 64 thereon for preventing fluid flow through the waste tubing 41.

Figure 10:
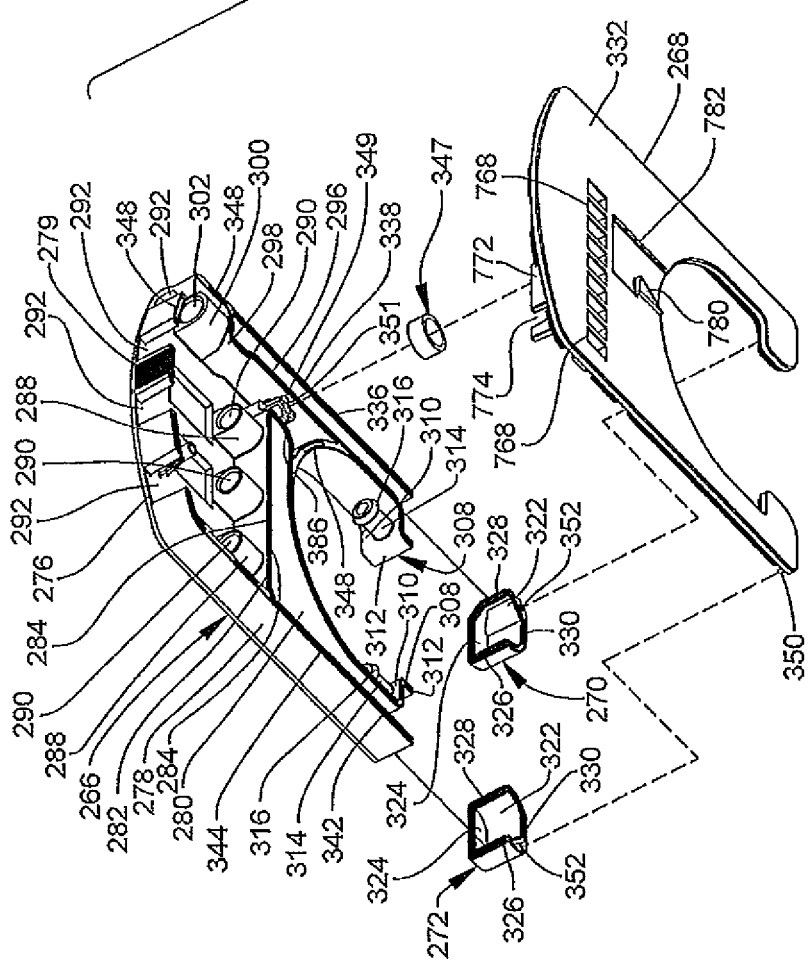
FIG. 10 is an exploded bottom perspective view of the outflow cassette of the present invention without peristaltic tubing.

In the illustrated example, the outflow cassette 26 could include an RF chip 347 for communicating information to the pump 14 once inserted into the pump 14. The RF chip 347 could have any configuration and could be located anywhere on or within the outflow cassette 26. In the illustrated example, the RF chip 347 is in the form of a cylinder located within the outflow cassette 26. As illustrated in FIG. 10, the top plate 276 of the top frame 266 includes a pronged tube 349 extending downwardly therefrom between the constriction 134 between the curved section 286 of the J-shaped entrance wall 282 and the inner egress side wall 296. The RF chip 347 fits securely over the pronged tube 349. The pronged tube 349 can include an aperture 351 in a free end thereof that is configured to accept a pin 353 extending upwardly from the bottom panel 332 of the bottom plate 268 for assisting in aligning the bottom plate 268 with the top frame 266. The RF chip 347 is configured to include information including properties of the outflow cassette tubing assembly 236. For example, the RF chip 347 can include information related to properties of the outflow tube 28, the device suction tubing 34, the waste tubing 41 and the peristaltic tubing 256 (e.g., material and size) to allow the control system to determine the flow rate of waste fluid from the body cavity 12 and/or to assist in slowing waste fluid flow through the outflow tube 28 and the device suction tubing 34 as described below (e.g., material and size of outflow tube 28 and device suction tubing 34 could be relevant when pinching the outflow tube 28 and the device suction tubing 34 to know how much to pinch the outflow tube 28 and device suction tubing 34).

Figure 12:
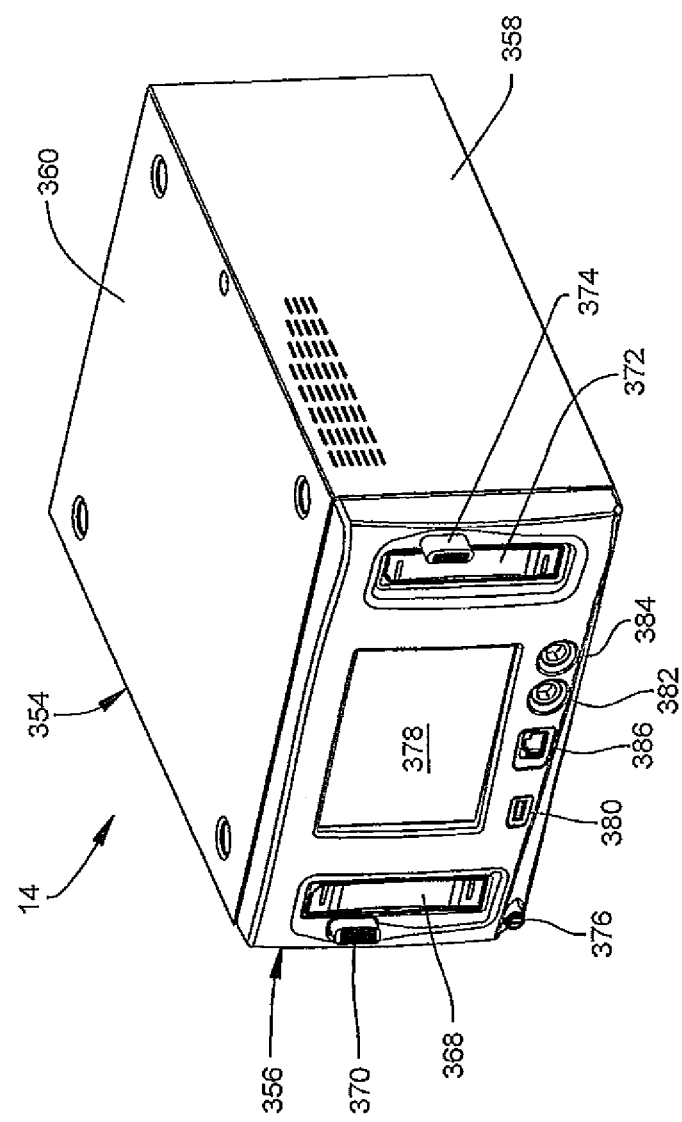
FIG. 12 is a perspective view of a pump of the present invention.
Figure 13:
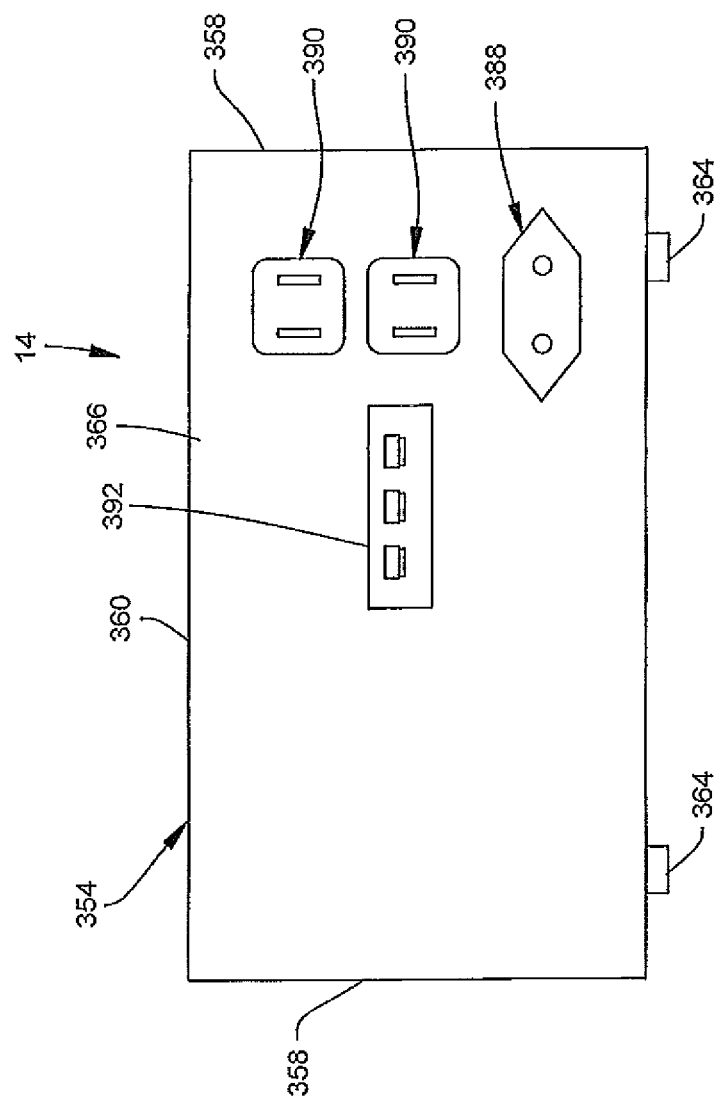
FIG. 13 is a rear view of the pump of the present invention.

The illustrated pump 14 (FIGS. 12-13) of the pump system 10 is configured to accept the inflow cassette 20 and the outflow cassette 26 therein to push the surgery washing fluid from the source of surgery washing fluid 16 to the body cavity 12 and to suction the waste fluid from the body cavity 12 and dispose of in the waste receptacle 40. The pump 14 can include a computer controller such as a micro-processor as discussed in more detail below that executes an algorithm to control at least the pump 14. The pump 14 includes a pump housing 354 having a front panel 356, sides 358, a top 360, a bottom 362 with support feet 364 and a rear panel 366. The front panel 356 includes an inflow cassette door 368 having an inflow cassette eject button 370 adjacent thereto and an outflow cassette door 372 having an outflow cassette eject button 374 adjacent thereto. Both the inflow cassette door 368 and the outflow cassette door 372 are spring biased to a closed position (as illustrated in FIG. 12), but will stay open when the inflow cassette 20 and the outflow cassette 26 are inserted into the pump housing 354, respectively. As discussed in more detail below, the inflow cassette 20 is inserted into the pump 14 through the inflow cassette door 368 and ejected from the pump 14 by pressing the inflow cassette eject button 370. Likewise, the outflow cassette 26 is inserted into the pump 14 though the outflow cassette door 372 and ejected from the pump 14 by pressing the outflow cassette eject button 374. A power button 376 is depressed to toggle the power to the pump 14.

In the illustrated example, the pump 14 includes a plurality of input ports for receiving information from all elements of the pump system 10 to change the flow rate and/or pressure of the surgery washing fluid to the body cavity 12 (i.e., inflow characteristics) and/or to change the flow rate and/or pressure of the suction of the waste fluid from the body cavity 12 (i.e., outflow characteristics). For example, the front panel 356 of the pump 14 can have a view screen 378 (e.g., LCD screen) for relaying information regarding the status of the pump 14 and the items connected thereto. The view screen 378 can also be a touch screen (and function as the input device 52) for allowing a user of the pump system 10 to set up user preferences and load settings for the pump 14 and/or change setting for the pump 14 during use. The pump 14 can also include a USB port 380, an 8 pin foot pedal port 382, a remote port 384 (e.g., a seven or eight pin port) and an auxiliary device port 386 (e.g., for connection to an in-joint pressure sensor). It is contemplated that the ports can have any connection scheme (e.g., 8 pin, USB, etc.) and can be connected to any device for supplying information to or receiving information from the pump 14.

The illustrated rear panel 366 of the pump housing 354 can also include input ports. For example, the rear panel 366 can include a power port 388 configured to accept a power cord connection element for supplying power to the pump 14. The rear panel 366 can also include power outlets 390 for devices connected to the pump 14 that need to be powered (e.g., the shaver 36 and the RF ablation device 38). The power outlets 390 can be configured to not only provide power to the surgery devices 32, but can also provide current and voltage information to the pump 14 to be used by the control system in the pump 14 to change the flow rate and/or pressure of the surgery washing fluid to the body cavity 12 (i.e., inflow characteristics) and/or to change the flow rate and/or pressure of the suction of the waste fluid from the body cavity 12 (i.e., outflow characteristics), especially for an unidentified third party surgery devices. The current and voltage delivered to the surgery devices 32 are tracked and the collected time-series data is used to determine when the surgery devices 32 are activated. This is be accomplished by, for example, comparing a shape of a quiescent current waveform with a shape of an applied current waveform at any given time which changes with activation and type of the surgery device 32. Instantaneous and past changes in the current wave form shape can be normalized to the changes in applied main voltage, and used in a linear-discrimination algorithm to optimally differentiate between times when the surgery devices 32 are off or activated. The resulting probability of surgery device 32 activation, especially for an unidentified third party device, is then passed to a motor control and pinch-valve activation algorithm to influence pump and suction performance as discussed in more detail below. The rear panel 366 can also include other information input ports 392 (e.g., a port for connecting the pump 14 to a Stryker® FIREWIRE™ Backbone bus arrangement as sold by Stryker® Corporation of Kalamazoo, Mich.). The Stryker® FIREWIRE™ Backbone bus arrangement is a bus arrangement that allows peer-to-peer communication between the various devices connected thereto. For example, the shaver 36 or RF ablation device 38 may be connected by the Stryker® FIREWIRE™ Backbone bus arrangement for two-way communication with the pump 14 and for communication with multiple devices. For instance, a remote controller device with connections to multiple devices may have a sub arrangement. For example, the shaver 36 and/or RF ablation device 38 connected over the Stryker® FIREWIRE™ Backbone bus arrangement avoids the necessity of individual connectors between the shaver 36 and RF ablation device 38 with multiple devices.

Figure 14:
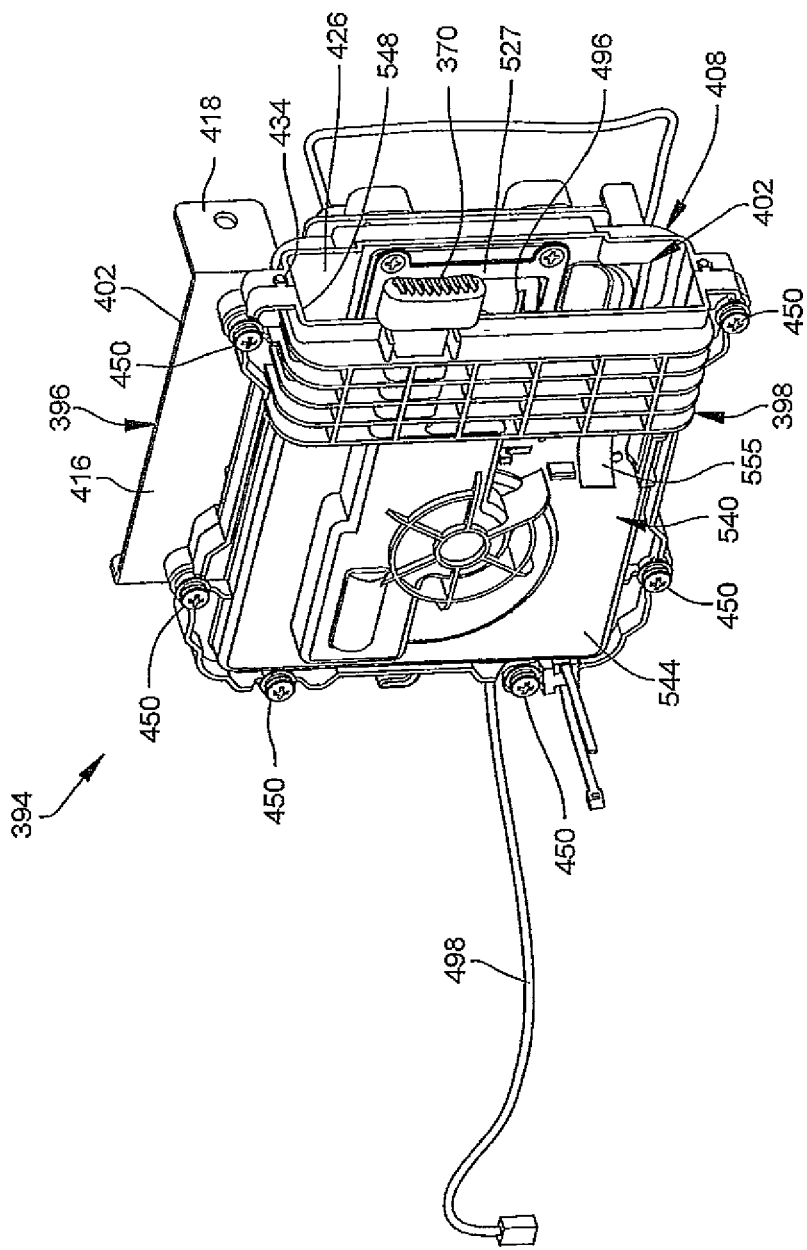
FIG. 14 is a perspective view of an inflow cassette receptacle assembly of the pump of the present invention.

When the illustrated inflow cassette 20 is inserted through the inflow cassette door 368, the inflow cassette 20 is received within an inflow cassette receptacle assembly 394 (FIGS. 14 and 15) within the pump housing 354. The inflow cassette receptacle assembly 394 includes a motor housing section 396, an ejection housing section 398 and a center seal 400. The center seal 400 is sandwiched between the motor housing section 396 and the ejection housing section 398. An inflow cassette receiving area 402 is defined between the motor housing section 396 and the ejection housing section 398, with the inflow cassette 20 being inserted through the inflow cassette door 368 and into the inflow cassette receiving area 402.

In the illustrated example, the motor housing section 396 (FIGS. 14-16) of the inflow cassette receptacle assembly 394 works to pump the surgery washing fluid through the inflow cassette 20. The motor housing section 396 includes a holding bracket 404, a pump motor 406, an inner housing member 408, pump motor seals 410, a roller wheel 412, and a sensor holder and housing assembly 414. The holding bracket 404 attaches the inflow cassette receptacle assembly 394 to the pump housing 354. The holding bracket 404 includes a plate 416 having a plurality of connection flanges 418 extending therefrom and a bottom foot 419. The bottom foot 419 rests on the bottom 362 of the pump housing 354 and fasteners are inserted through the connection flanges 418 and into the pump housing 354 to connect the inflow cassette receptacle assembly 394 to the pump housing 354. The plate 416 of the holding bracket 404 includes a circular motor opening 420 having a plurality of fastener openings 422 surrounding the circular motor opening 420 and a substantially rectangular sensing device opening 424. The holding bracket 404 can be made or any material (e.g., metal or plastic) and can have other configurations for maintaining the inflow cassette receptacle assembly 394 in position within the pump 14.

The illustrated inner housing member 408 of the motor housing section 396 of the inflow cassette receptacle assembly 394 is configured to receive a portion of the inflow cassette 20 when the inflow cassette 20 is inserted into the inflow cassette receptacle assembly 394. The inner housing member 408 includes a panel 426 connected to the holding bracket 404. The panel 426 includes a rectangular recessed area 427 having a circular motor opening 428 and a plurality of fastener openings 430 surrounding the circular motor opening 428. When the inner housing member 408 is connected to the holding bracket 404, the circular motor opening 420 and the plurality of fastener openings 422 of the holding bracket 404 are aligned with the circular motor opening 428 and the fastener openings 430 of the inner housing member 408, respectively. A substantially circular flange 432 surrounds the circular motor opening 428 and substantially circular ridges 433 surround each of the fastener openings 430 in the rectangular recessed area 427 of the panel 426.

In the illustrated example, the inner housing member 408 includes a substantially C-shaped flange 434 extending perpendicularly from the panel 426 and defining a top, a bottom and an end of the portion of the inflow cassette receptacle assembly 394 defined by the motor housing section 396 of the inflow cassette receptacle assembly 394. The substantially C-shaped flange 434 includes a top leg 436, a bottom leg 438 and a rear leg 440. The top leg 436 and the bottom leg 438 each have diverging ends 442 opposite the rear leg 440 for allowing the inflow cassette 20 to be easily accepted into the inflow cassette receiving area 402 of the portion of the inflow cassette receptacle assembly 394 defined by motor housing section 396 of the inflow cassette receptacle assembly 394. The rear leg 440 includes a first half of inwardly facing cassette feet receivers 444 for accepting a portion of the inwardly facing feet 82 of the inflow cassette 20 therein when the inflow cassette 20 is inserted into the inflow cassette receptacle assembly 394 to assist in properly aligning the inflow cassette 20 within the inflow cassette receptacle assembly 394. While not shown, the first half of the inwardly facing cassette feet receivers 444 (along with corresponding inwardly facing cassette feet receivers 557 in the ejection housing section 398) can hold coil springs for assisting in pushing the inflow cassette 20 out of the inflow cassette receptacle assembly 394 when the inflow cassette eject button 370 is depressed. A plurality of connection flanges 446 extend outward from an outside face of the substantially C-shaped flange 434. The connection flanges 446 have fastener openings 448 therein for accepting fasteners 450 to connect the motor housing section 396 to the ejection housing section 398. The inner housing member 408 can be formed of any material (e.g., injection molded plastic and/or metal).

The illustrated pump motor 406 is connected to the holding bracket 404 and the inner housing member 408 and is configured to rotate the roller wheel 412. The pump motor 406 includes a motor housing 452 and an output shaft 454. The pump motor 406 has a power supply (not shown) connected thereto for rotating the output shaft 454. The pump motor housing 452 includes a plurality of fastener holes 456. The pump motor 406, the holding bracket 404 and the inner housing member 408 are connected together by first surrounding the holding bracket 404 with the pump motor seals 410. Each pump motor seal 410 includes a central circular opening 458 surrounded by fastener openings 460. The holding bracket 404, the inner housing member 408 and the pump motor seals 410 are aligned such that the circular motor opening 420 of the holding bracket 404, the circular motor opening 428 in the inner housing member 408, and the central circular opening 458 in the pump motor seals 410 are aligned and such that the fastener openings 422 in the holding bracket 404, the fastener openings 430 in the inner housing member 408, and the fastener openings 460 in the pump motor seals 410 are aligned. Fasteners 462 are then inserted through the fastener openings 422 in the holding bracket 404, the fastener openings 430 in the inner housing member 408, the fastener openings 460 in the pump motor seals 410 and into the fastener holes 456 in the pump motor housing 452 to connect the pump motor 406 to the holding bracket 404 and the inner housing member 408. Once connected, the output shaft 454 of the pump motor 406 will extend through a center of the circular motor opening 420 of the holding bracket 404, the circular motor opening 428 in the inner housing member 408 and the central circular opening 458 in the pump motor seals 410.

Figure 15:
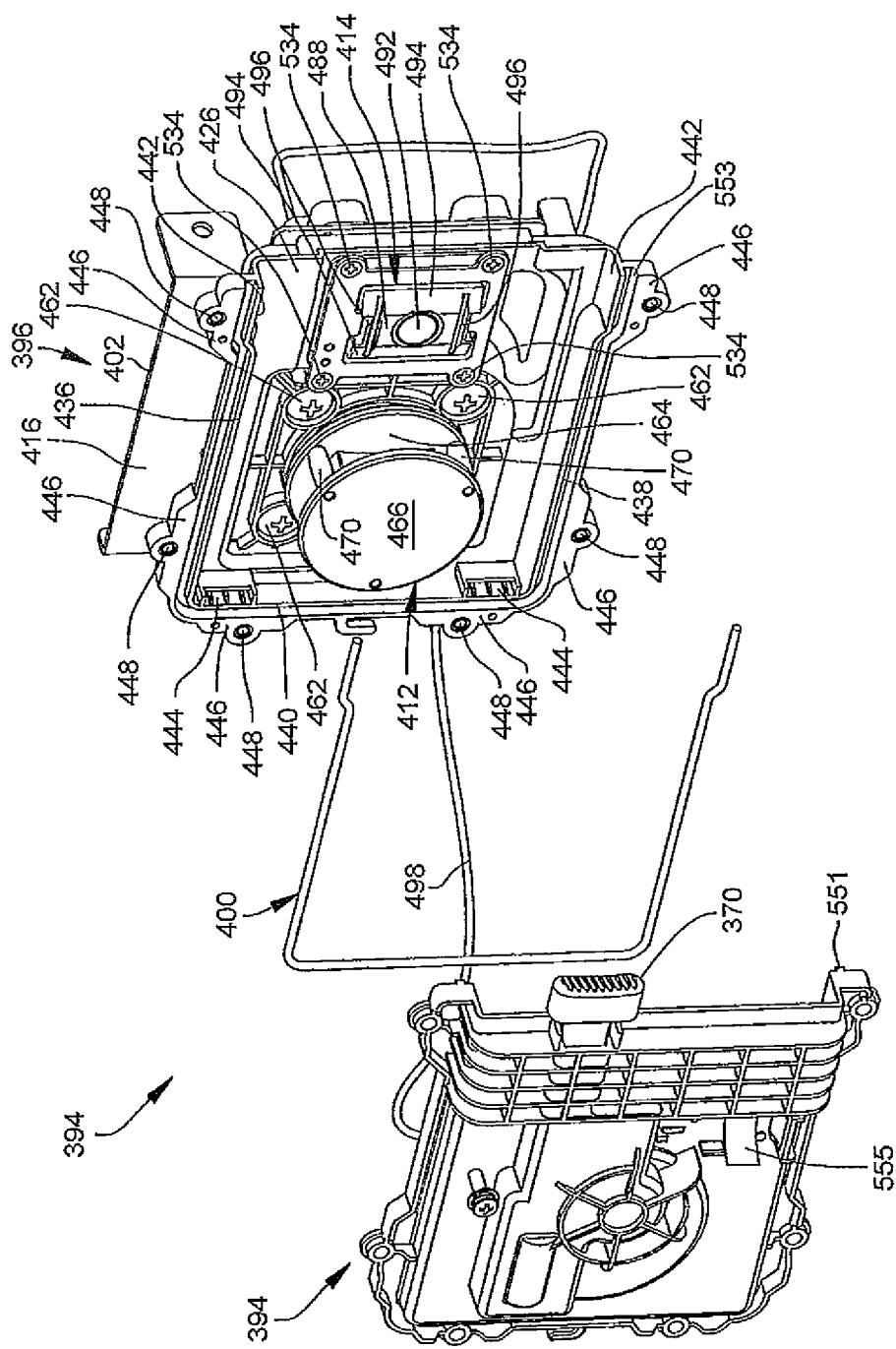
FIG. 15 is an exploded perspective view of the inflow cassette receptacle assembly of the pump of the present invention.
Figure 16:
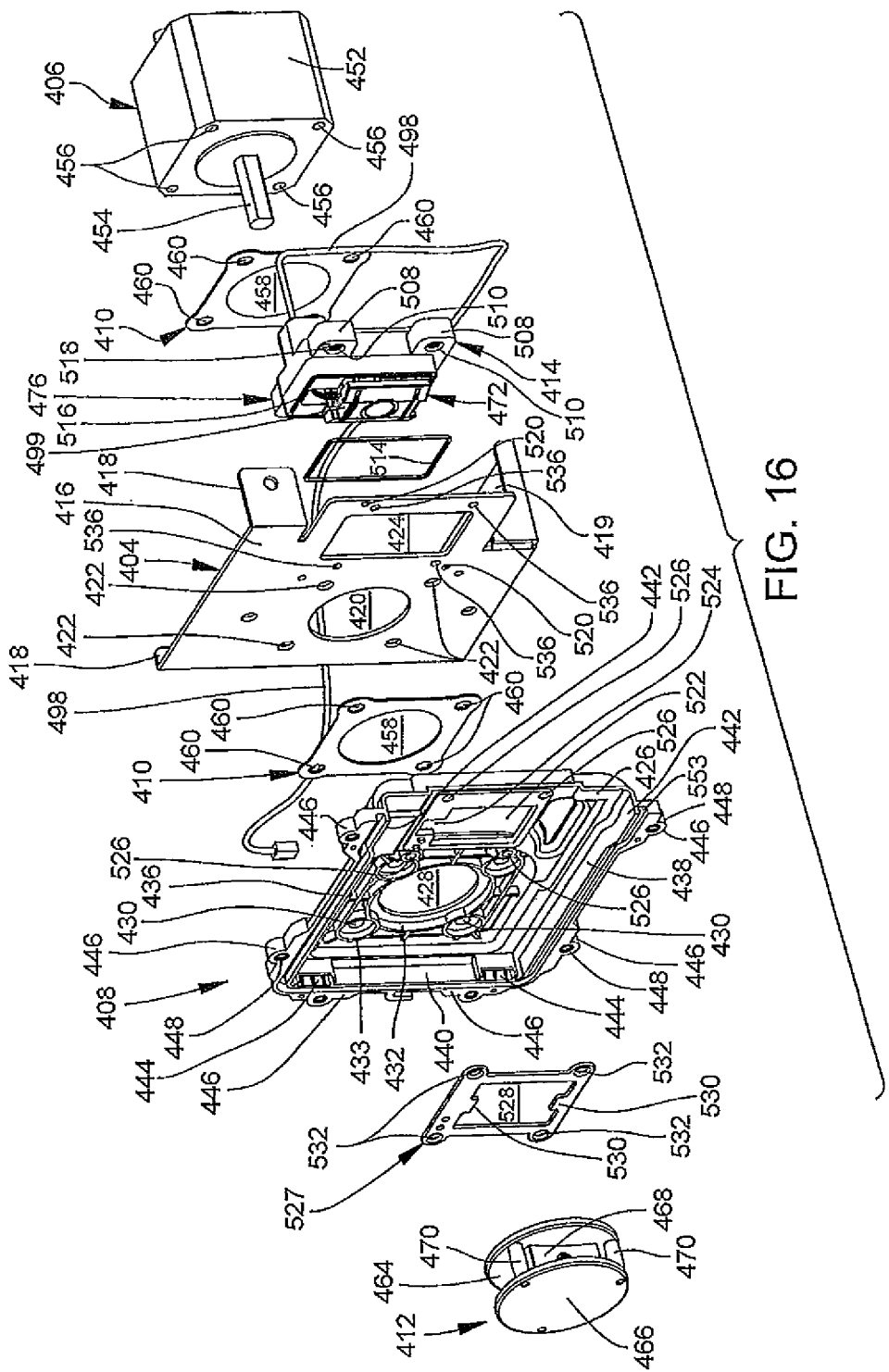
FIG. 16 is an exploded perspective view of a motor housing section of the inflow cassette receptacle assembly of the pump of the present invention.
Figure 17:
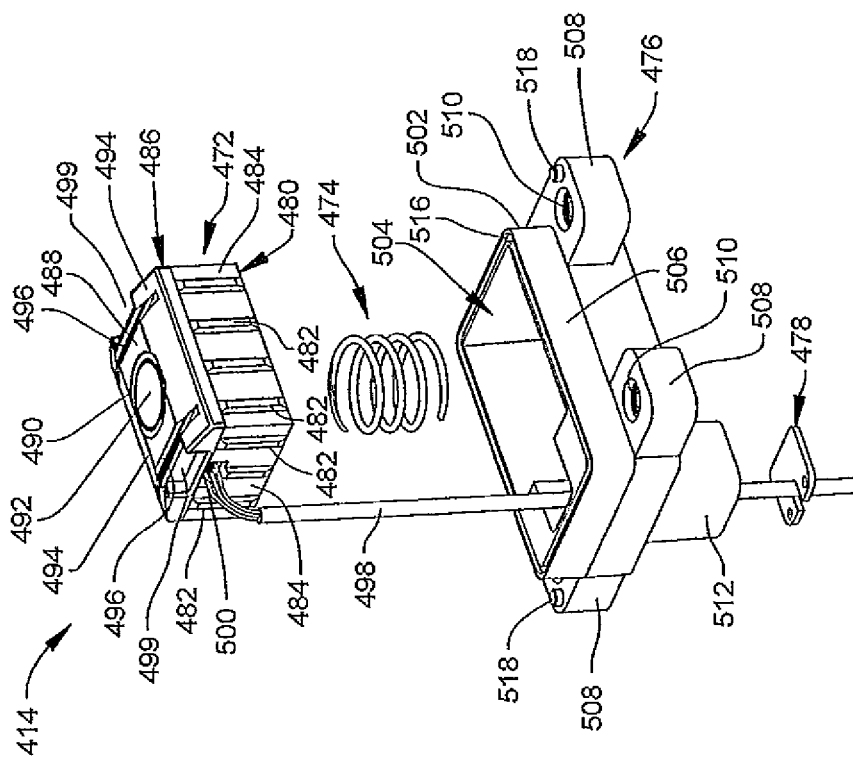
FIG. 17 is an exploded perspective view of a sensor holding and housing assembly of the motor housing section of the inflow cassette receptacle assembly of the pump of the present invention.
Figure 18:
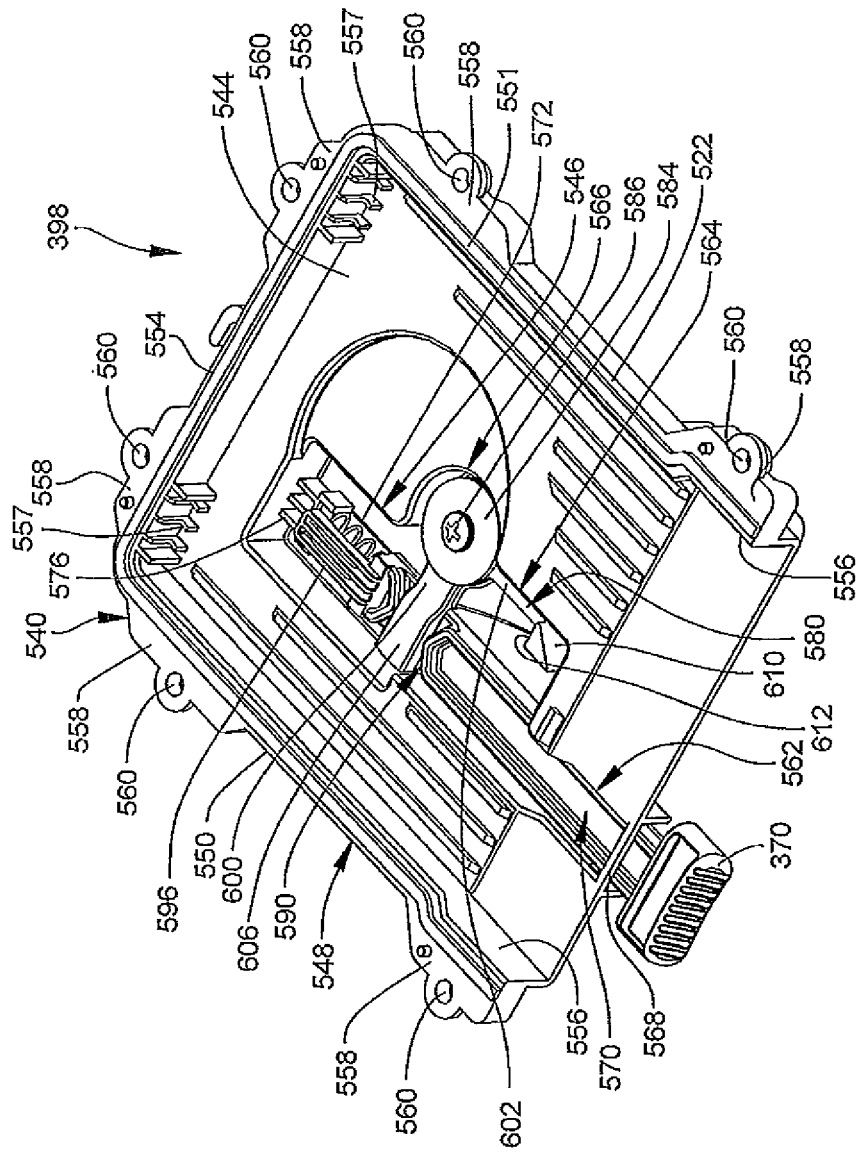
FIG. 18 is a side perspective view of an ejection housing section of the inflow cassette receptacle assembly of the pump of the present invention.

In the illustrated example, the roller wheel 412 is rotated by the pump motor 406. The roller wheel 412 includes a first disc 464, a second disc 466, a shaft receptacle 468 and a plurality of roller cylinders 470. The roller cylinders 470 extend between and are connected to the first disc 464 and the second disc 466. The roller cylinder 470 can include a center post fixedly connected to the first disc 464 and the second disc 466 and an outer sleeve configured to be able to freely rotate on the center post. In the illustrated example, three roller cylinders 470 extend between the first disc 464 and the second disc 466 adjacent the peripheral edge thereof such that rotation of the first disc 464 and the second disc 466 will move the roller cylinders 470 along the same circular path. It is contemplated that any number of roller cylinders 470 (e.g., 3, 4, 5, etc.) could be used. Increasing the number of roller cylinders 470 can decrease pressure pulses in the peristaltic tubing, but a maximum flow rate of the fluid through the peristaltic tubing is decreased at higher RPMs of the roller wheel 412 as the number of roller cylinders 470 increases. The number of roller cylinders 470 and the RPM of the roller wheel 412 are used as inputs into the control system to control the inflow characteristics. The shaft receptacle 468 is located between the first disc 464 and the second disc 466 and is connected to at least one of the same. The shaft receptacle 468 is configured to receive the output shaft 454 of the pump motor 406 therein such that rotation of the output shaft 454 will cause rotation of the first disc 464 and the second disc 466 to thereby rotate the roller cylinders 470 in a circular path centered about the output shaft 454. It is contemplated that the output shaft 454 could have a non-circular cross-section to allow the output shaft 454 to be received within the shaft receptacle 468 of the roller wheel 412 to easily rotate the roller wheel 412. As illustrated in FIG. 15, the first disc 464 of the roller wheel 412 sits on an edge of the substantially circular flange 432 extending around the circular motor opening 428 in the panel 426 of the inner housing member 408.

During use of the pump 14, the pump motor 406 will rotate the roller wheel 412 to push the surgery washing fluid through the peristaltic tubing 70 of the inflow cassette 20 by having the roller cylinders 470 compress the peristaltic tubing 70 along a length thereof from a beginning of the peristaltic tubing 70 adjacent the second area 109 of the ingress path section 92 towards the entry area 95 of the egress path section 94 of the interior fluid flow path 91. The egress path section 94 is designed in such a manner that as fluid initially moves through the inflow cassette 20, air is completely pushed out of the egress path section 94 so that there are no air bubbles entering into the body cavity 12 during a surgical procedure. As discussed in more detail below, the output of the pump motor 406 (e.g., speed of output shaft 454) can be used to alter the flow rate and/or pressure of the surgery washing fluid to the body cavity 12 (i.e., inflow characteristics). It is contemplated that the RPMs of the roller wheel 412 and a position of the roller wheel 412 and the roller cylinders 470 of the roller wheel 412 can be determined by any means. For example, an encoder coupled to the output shaft 454 of the pump motor 406 could include a Hall sensor and/or an optical reader to determine the RPMs of the output shaft 454 (and the roller wheel 412) and the position of the output shaft 454 (and the roller wheel 412) in a manner well known to those skilled in the art.

In the illustrated example, the sensor holder and housing assembly 414 (FIGS. 14-17) is connected to the holding bracket 404 and the inner housing member 408 and is configured to sense a pressure of the surgery washing fluid in the pressure sensing area 100 of the inflow cassette 20. The sensor holder and housing assembly 414 includes a sensor assembly 472, a biasing member 474, a sensor housing 476 and a sensor cable holder 478. The sensor assembly 472 includes a bottom block shaped section 480 having a plurality of parallel vertically extending ribs 482 extending from each of the side walls 484 thereof. The sensor assembly 472 also include a top section 486 having a top surface 488 with a centrally located sensor opening 490 having a pressure sensor 492 located therein. The top section 486 also includes a pair of angled surfaces 494 located on two opposite sides of the top surface 488. A pair of parallel rail receiving slots 496 extend through the angled surfaces 494 and the top surface 488 on two sides of the pressure sensor 492. A longitudinal direction of the parallel rail receiving slots 496 is perpendicular to a longitudinal direction of the angled surfaces 494. A pair of holding tab receiving slots 499 are positioned in ends of the top surface 488 outside of the parallel rail receiving slots 496. A sensor cable 498 connected to the pressure sensor 492 extends out of a cable opening 500 in the bottom block shaped section 480 directly below the top section 486 of the sensor assembly 472. The sensor assembly 472 is slidably received within the sensor housing 476.

The illustrated sensor housing 476 includes a tub 502 defining an open area 503 for receiving the sensor assembly 472 therein. The tub 502 has a rectangular periphery corresponding to a rectangular space defined by the outer ends of the parallel vertically extending ribs 482 extending from each of the side walls 484 of the bottom block shaped section 480 of the sensor assembly 472. The sensor assembly 472 is slid into the tub 502 of the sensor housing 476, with the biasing member 474 being located between a floor of the tub 502 and a bottom surface of the bottom block shaped section 480 of the sensor assembly 472. The biasing member 474 biases the sensor assembly 472 away from the floor of the tub 502 of the sensor housing 476. As the sensor assembly 472 slides within the tub 502 of the sensor housing 476, only the outer ends of the parallel vertically extending ribs 482 extending from each of the side walls 484 of the bottom block shaped section 480 of the sensor assembly 472 abut the side walls of the tub 502, thereby minimizing friction contact between the sensor housing 476 and the sensor assembly 472. In the illustrated example, the biasing member 474 is a coil metal spring. However, it is contemplated that any biasing member 474 could be used. The tub 502 includes a side bay 504 for receiving the sensor cable 498 therein to allow the sensor assembly 472 to easily slide within the sensor housing 476. A cable holding tube 512 extends from a bottom of the tub 502, with the sensor cable holder 478 being connected to the cable holding tube 512 for holding the sensor cable 498. As described in more detail below, the pressure sensor 492 in the sensor assembly 472 is used to measure the pressure of the surgery washing fluid within the pressure sensing area 100 of the interior fluid flow path 91 within the inflow cassette 20.

In the illustrated example, the sensor holder and housing assembly 414 is connected to the holding bracket 404 to be able to interact with the inflow cassette 20 within the pump 14. The sensor housing 476 includes a top rectangular outer wall 506 outside of the tub 502 and a plurality of side connection flanges 508 extending outwardly from the tub 502 below the top rectangular outer wall 506. Each of the side connection flanges 508 includes an internally threaded opening 510 therein. To assemble the motor housing section 396, the sensor housing 476 having the sensory assembly 472 therein is slid through the substantially rectangular sensing device opening 424 in the plate 416 of the holding bracket 404. The top rectangular outer wall 506 of the sensor housing 476 closely fits within the substantially rectangular sensing device opening 424. A rectangular seal 514 can be positioned within a rectangular channel 516 in a top edge of the top rectangular outer wall 506 of the sensor housing 476 to seal the sensor housing 476 against the holding bracket 404. Two of the side connection flanges 508 can include pins 518 extending therefrom adjacent to the internally threaded opening 510, with the pins 518 being configured to be received into complementary receiving holes 520 adjacent the substantially rectangular sensing device opening 424 in the plate 416 of the holding bracket 404 to assist in properly aligning the sensor holder and housing assembly 414 against the holding bracket 404.

The illustrated sensor holder and housing assembly 414 is also connected to the inner housing member 408 to be able to interact with the inflow cassette 20 within the pump 14. The inner housing member 408 includes a rectangular sensor hole 522 having an adjacent cable notch 524 along a short edge of the rectangular sensor hole 522. The top rectangular outer wall 506 of the sensor housing 476 closely fits within the rectangular sensor hole 522 in the inner housing member 408. The sensor cable 498 connected to the pressure sensor 492 and extending out of the cable opening 500 in the bottom block shaped section 480 the sensor assembly 472 extends through the cable notch 524. A plurality of fastener openings 526 surround the rectangular sensor hole 522. A front holding plate 527 connects the sensor holder and housing assembly 414 to the inner housing member 408, with the front holding plate 527 comprising a rectangular sensor opening 528 having a pair of aligned holding tabs 530 extending toward each other from opposite short sides of the rectangular sensor opening 528. The front holding plate 527 also includes a plurality of fastener openings 532 surrounding the rectangular sensor opening 528. The front holding plate 527 is placed over the inner housing member 408, with the rectangular sensor opening 528 of the front holding plate 527 overlying the rectangular sensor hole 522 of the inner housing member 408. As illustrated in FIG. 15, fasteners 534 are inserted through the fastener openings 532 in the front holding plate 527, through the fastener openings 526 in the inner housing member 408, through a plurality of fastener openings 536 in the holding bracket 404 adjacent the substantially rectangular sensing device opening 424, and into the internally threaded openings 510 in the side connection flanges 508 of the sensor housing 476. The pair of aligned holding tabs 530 of the front holding plate 527 slide within the pair of holding tab receiving slots 499 positioned in ends of the top surface 488 of the top section 486 of the sensor assembly 472 to maintain the sensor assembly 472 in proper alignment as the sensor assembly 472 is pressed toward and away from a bottom surface of the tub 502 of the sensor housing 476.

In the illustrated example, the pressure sensor 492 of the sensor assembly 472 is used to measure the pressure of the surgery washing fluid within the pressure sensing area 100 of the interior fluid flow path 91 within the inflow cassette 20. As the inflow cassette 20 is inserted into the inflow cassette receiving area 402 of the inflow cassette receptacle assembly 394, the top plate 76 of the top frame 66 of the inflow cassette 20 will abut against one of the angled surfaces 494 of the top section 486 of the sensor assembly 472 of the sensor holder and housing assembly 414. As the top plate 76 of the top frame 66 of the inflow cassette 20 abuts against one of the angled surfaces 494 of the top section 486 of the sensor assembly 472, the sensor assembly 472 will be pushed toward the bottom of the tub 502 of the sensor housing 476 against the bias of the biasing member 474. When the inflow cassette 20 is fully inserted into the inflow cassette receiving area 402 of the inflow cassette receptacle assembly 394, the biasing member 474 will push the sensor assembly 472 back outward from the bottom of the tub 502 of the sensor housing 476.

Once the illustrated inflow cassette 20 is fully inserted into the inflow cassette receiving area 402 of the inflow cassette receptacle assembly 394, the pressure sensor 492 in the sensor assembly 472 can begin measuring the pressure of the surgery washing fluid within the pressure sensing area 100 of the interior fluid flow path 91 within the inflow cassette 20. When the inflow cassette 20 is fully inserted into the pump 14, the angled surfaces 494 of the top section 486 of the sensor assembly 472 will abut against the ramps 222 of the top frame 66 of the inflow cassette 20. The abutment of the ramps 222 and the angled surfaces 494 help to align the pressure sensor 492 of the top section 486 of the sensor assembly 472 over the disc-shaped pressure sensing membrane 212 in the circular seat 208 of the inflow cassette 20. Furthermore, the two of the parallel guide strips 216 on either side of the circular seat 208 that have the thinner center sections 218 will be accepted into the parallel rail receiving slots 496 in the top section 486 of the sensor assembly 472, thereby correctly aligning the pressure sensor 492 of the top section 486 of the sensor assembly 472 over the disc-shaped pressure sensing membrane 212 in the circular seat 208 of the inflow cassette 20.

Figure 6:
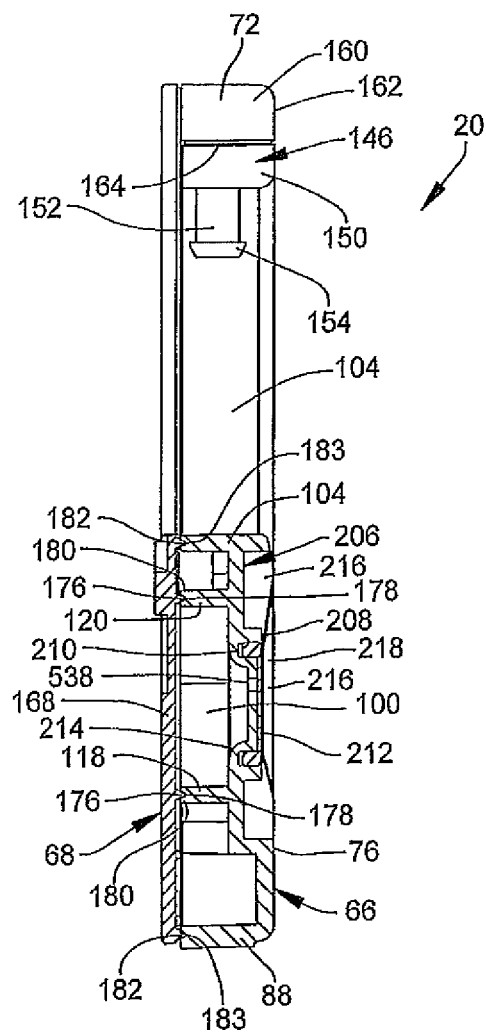
FIG. 6 is a side cross-sectional view of the inflow cassette of the present invention.

In the illustrated example, once the pressure sensor 492 of the top section 486 of the sensor assembly 472 is aligned with the disc-shaped pressure sensing membrane 212 in the circular seat 208 of the inflow cassette 20, the pressure of the surgery washing fluid within the pressure sensing area 100 of the interior fluid flow path 91 within the inflow cassette 20 can be measured. As illustrated in FIG. 6, once the surgery washing fluid in the inflow cassette 20 reaches the pressure sensing area 100, the surgery washing fluid flows through an access slot 538 in the bottom of the rectangular recess 206 in the top frame 66 of the inflow cassette 20 to an area directly below the disc-shaped pressure sensing membrane 212. The pressure of the surgery washing fluid will provide a force against the disc-shaped pressure sensing membrane 212, which will in turn provide a force against the pressure sensor 492 of the top section 486 of the sensor assembly 472. The pressure sensor 492 of the top section 486 of the sensor assembly 472 will convert the force applied thereto from the disc-shaped pressure sensing membrane 212 into a signal (for example, analog or digital), which is sent through the sensor cable 498 to the control system of the pump 14. As described in more detail below, the pressure of the surgery washing fluid in the pressure sensing area 100 of the interior fluid flow path 91 within the inflow cassette 20 can be used to alter the flow rate and/or pressure of the surgery washing fluid to the body cavity 12. During removal of the inflow cassette 20 from the inflow cassette receptacle assembly 394, the sensor assembly 472 presses against the biasing member 474 and moves further into the tub 502 to allow the inflow cassette 20 to pass thereby.

The illustrated ejection housing section 398 of the inflow cassette 20 maintains the inflow cassette 20 within the inflow cassette receiving area 402 to allow the pump motor 406 to pump the surgery washing fluid through the inflow cassette 20 and to allow the pressure within the pressure sensing area 100 to be sensed by the pressure sensor 492. The ejection housing section 398 includes an outer housing member 540 and a locking assembly 542. The outer housing member 540 works with the inner housing member 408 of the motor housing section 396 of the inflow cassette receptacle assembly 394 to hold the inflow cassette 20 and the locking assembly 542 locks the inflow cassette 20 within the inflow cassette receptacle assembly 394.

In the illustrated example, the outer housing member 540 of the ejection housing section 398 of the inflow cassette receptacle assembly 394 is configured to receive a portion of the inflow cassette 20 when the inflow cassette 20 is inserted into the inflow cassette receptacle assembly 394. The outer housing member 540 has an overall shape very similar to the inner housing member 408 of the motor housing section 396. The outer housing member 540 includes a panel 544 having a locking assembly recess 546. An outside face of the panel 544 can include an RF antenna 555 for receiving the information on the RF chip 217 in the inflow cassette 20. The RF antenna 555 communicates the information on the RF chip 217 to the control system of the pump 14. In the illustrated example, the outer housing member 540 includes a substantially C-shaped flange 548 extending perpendicularly from the panel 544 and defining a top, a bottom and an end of the portion of the inflow cassette receptacle assembly 394 defined by the ejection housing section 398 of the inflow cassette receptacle assembly 394. The substantially C-shaped flange 548 includes a top leg 550, a bottom leg 552 and a rear leg 554. A plurality of connection flanges 558 extend outward from an outside face of the substantially C-shaped flange 548. The connection flanges 558 have fastener openings 560 therein for accepting fasteners 450 to connect the motor housing section 396 to the ejection housing section 398. The substantially C-shaped flange 548 of the outer housing member 540 can include a C-shaped ridge 551 extending laterally therefrom, with the C-shaped ridge 551 extending into a C-shaped channel 553 in the C-Shaped flange 434 of the inner housing member 408 of the motor housing section 396. The center seal 400 can be compressed by the C-shaped ridge 551 within the C-shaped channel 553 when the motor housing section 396 is connected to the ejection housing section 398 with the fasteners 450.

The illustrated top leg 550 and the bottom leg 552 each have diverging ends 556 opposite the rear leg 554 for allowing the inflow cassette 20 to be easily accepted into the inflow cassette receiving area 402 of the portion of the inflow cassette receptacle assembly 394 defined by the ejection housing section 398 of the inflow cassette receptacle assembly 394. The rear leg 554 includes a second half of the inwardly facing cassette feet receivers 557 for accepting a portion of the inwardly facing feet 82 of the inflow cassette 20 therein when the inflow cassette 20 is inserted into the inflow cassette receptacle assembly 394 to assist in properly aligning the inflow cassette 20 within the inflow cassette receptacle assembly 394. While not shown, the second half of the inwardly facing cassette feet receivers 557 (along with corresponding inwardly facing cassette feet receivers 444 in the motor housing section 396) can hold coil springs for assisting in pushing the inflow cassette 20 out of the inflow cassette receptacle assembly 394 when the inflow cassette eject button 370 is depressed.

The illustrated outer housing member 540 includes the locking assembly recess 546 in the panel 544, with the locking assembly recess 546 receiving the locking assembly 542 therein. The locking assembly recess 546 includes a top elongated substantially rectangular ejection button mechanism slot 562, a bottom short substantially rectangular lock wedge movement area 564 and an annular rim area 566 adjacent the bottom short substantially rectangular lock wedge movement area 564. A bridge 568 spans over the front edge of the top elongated substantially rectangular ejection button mechanism slot 562 for assisting in maintaining an ejection button mechanism 570 within the top elongated substantially rectangular ejection button mechanism slot 562 as discussed in more detail below. The top elongated substantially rectangular ejection button mechanism slot 562 includes a spring half pipe holder 572 in a rear portion thereof, with a spring abutment wall 574 being located at a rear end of the spring half pipe holder 572. The outer housing member 540 can include abutment wall supports 576 behind the spring abutment wall 574 for providing stability to the spring abutment wall 574. The annular rim area 566 includes a cylindrical lock lever hub 578 with a centrally located threaded opening 579 extending from a bottom surface thereof.

In the illustrated example, the locking assembly 542 is positioned within the locking assembly recess 546 in the panel 544 of the outer housing member 540. The locking assembly 542 includes the ejection button mechanism 570, a lock lever 580, a spring 582, a washer 584 and a fastener 586. The ejection button mechanism 570 includes a rod 588 having the inflow cassette eject button 370 on a front end thereof. The rod 588 has a rear channel 590 in a side face thereof and extending from a top to a bottom of the rod 588. The illustrated rear channel 590 includes a pair of vertically aligned chevron-shaped side walls 592. A rear end of the rod 588 defines a pushing wall 594. An alignment finger 596 extends rearwardly from a rear end of the rod 588.

Figure 20:
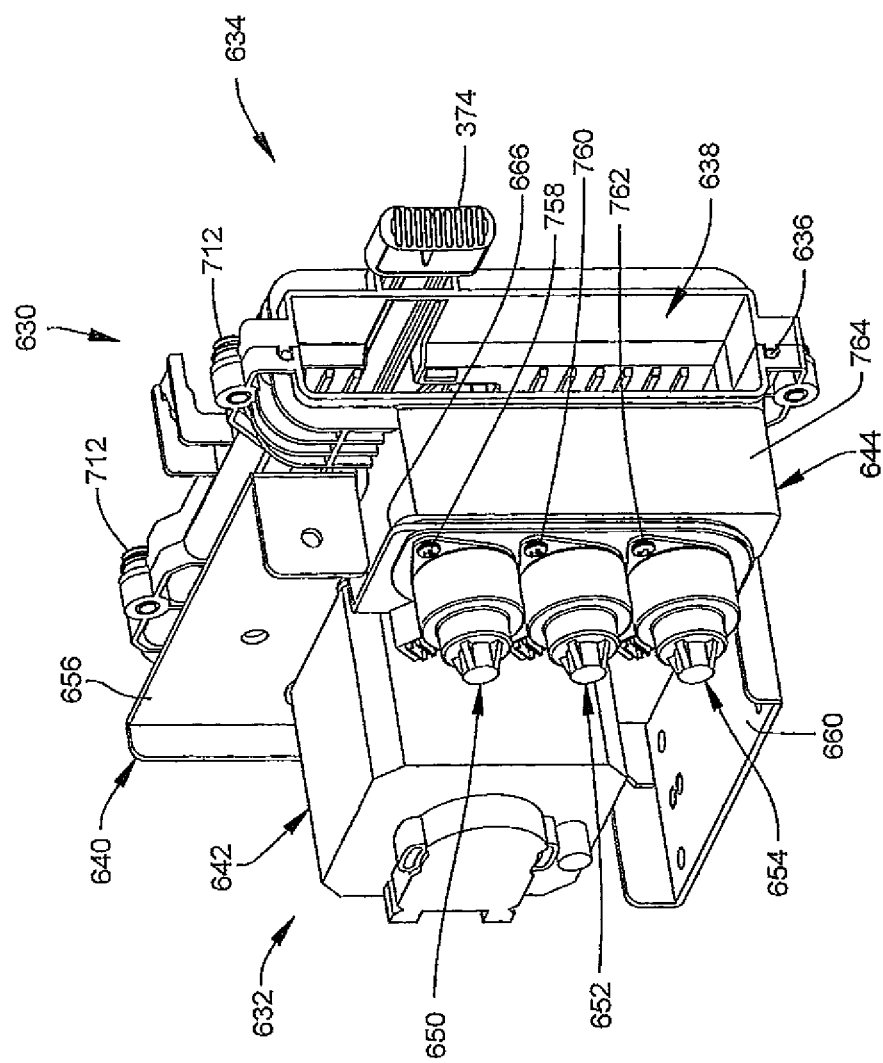
FIG. 20 is a perspective view of an outflow cassette receptacle assembly of the pump of the present invention.

The illustrated ejection button mechanism 570 is connected to the outer housing member 540 by sliding the alignment finger 596 and the rod 588 of the ejection button mechanism 570 under the bridge 568 over the front edge of the top elongated substantially rectangular ejection button mechanism slot 562 and into the top elongated substantially rectangular ejection button mechanism slot 562 as illustrated in FIG. 20. Before the ejection button mechanism 570 is fully inserted into the top elongated substantially rectangular ejection button mechanism slot 562, the spring 582 is positioned in the spring half pipe holder 572 in the rear portion of the top elongated substantially rectangular ejection button mechanism slot 562. As the ejection button mechanism 570 is fully inserted into the top elongated substantially rectangular ejection button mechanism slot 562, the spring 582 is compressed between the pushing wall 594 at the rear end of the rod 588 and the spring abutment wall 574 located at the rear end of the spring half pipe holder 572. Therefore, the spring 582 will push the rod 588 and the ejection button mechanism 570 in a direction out of the top elongated substantially rectangular ejection button mechanism slot 562. The lock lever 580 maintains the ejection button mechanism 570 within the top elongated substantially rectangular ejection button mechanism slot 562.

In the illustrated example, the lock lever 580 keeps the inflow cassette 20 within the inflow cassette receiving area 402 of the inflow cassette receptacle assembly 394. The lock lever 580 includes a rim 598, a first arm 600 and a second arm 602. The rim 598 includes a central opening 604 having a diameter substantially corresponding to an outer diameter of the cylindrical lock lever hub 578 in the annular rim area 566 of the locking assembly recess 546 in the panel 544 of the outer housing member 540. The first arm 600 extends radially from the rim 598 and includes an offset hand 606 at a distal end thereof. The second arm 602 also extends radially from the rim 598 at about 270° offset from the first arm 600. The second arm 602 has a triangular wedge 608 extending from an end thereof in a direction parallel to the axis of rotation of the lock lever 580. The triangular wedge 608 is formed as a right triangle with an angled edge 610 facing away from the rim 598 and a holding edge 612 facing the rim 598. The lock lever 580 can include a strut 614 extending between the first arm 600 and the second arm 602.

The illustrated lock lever 580 maintains the ejection button mechanism 570 within the top elongated substantially rectangular ejection button mechanism slot 562. Once the ejection button mechanism 570 has been inserted into the top elongated substantially rectangular ejection button mechanism slot 562 as discussed above, the lock lever 580 is inserted into the locking assembly recess 546 by inserting the cylindrical lock lever hub 578 in the annular rim area 566 of the locking assembly recess 546 in the panel 544 of the outer housing member 540 into the central opening 604 in the rim 598 of the lock lever 580. The lock lever 580 is positioned within the locking assembly recess 546 such that the offset hand 606 at the end of the first arm 600 extends into the rear channel 590 in the rod 588 between the vertically aligned chevron-shaped side walls 592. Furthermore, the second arm 602 extends into the bottom short substantially rectangular lock wedge movement area 564. To securely lock the lock lever 580 to the outer housing member 540, the fastener 586 is positioned through an opening in the washer 584, through the central opening 604 in the rim 598 of the lock lever 580, and into the internal centrally located threaded opening 579 in the cylindrical lock lever hub 578. The washer 584 holds the lock lever 580 in position within the locking assembly recess 546 in the panel 544 of the outer housing member 540 and allows the lock lever 580 to rotate a small amount about the cylindrical lock lever hub 578.

In the illustrated example, the lock lever 580 and the ejection button mechanism 570 work with the inflow cassette 20 to lock the inflow cassette 20 within the inflow cassette receiving area 402 of the inflow cassette receptacle assembly 394 and to eject the inflow cassette 20 from the inflow cassette receiving area 402 of the inflow cassette receptacle assembly 394. As illustrated in FIG. 4, the bottom plate 68 of the inflow cassette 20 includes a triangular lock block 616 located in a locking indentation 618 adjacent the arched cutout 84. The triangular lock block 616 includes an abutment edge 620 and a lock edge 622. The inflow cassette 20 is inserted into and withdrawn from the inflow cassette receiving area 402 of the inflow cassette receptacle assembly 394 along an insertion line between the insertion side and the extraction side thereof of the inflow cassette 20. The abutment edge 620 of the triangular lock block 616 on the bottom plate 68 of the inflow cassette 20 is angled relative to the insertion line and the lock edge 622 is perpendicular to the insertion line.

Figure 19A:
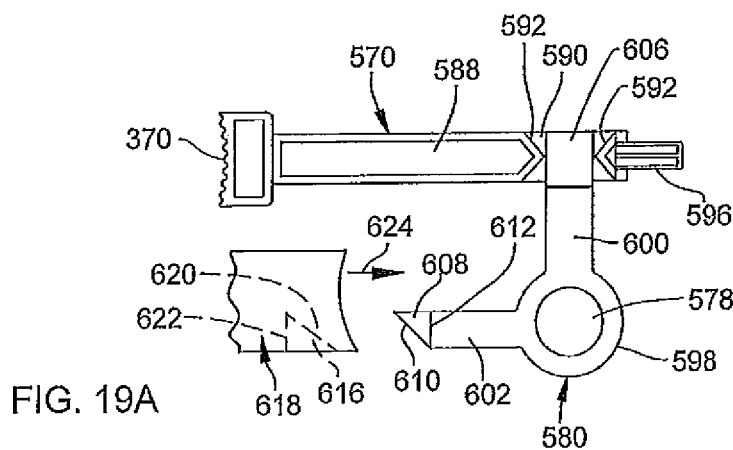
FIG. 19A is a partial sectional view illustrating the inflow cassette of the present invention being loaded into the pump.
Figure 19B:
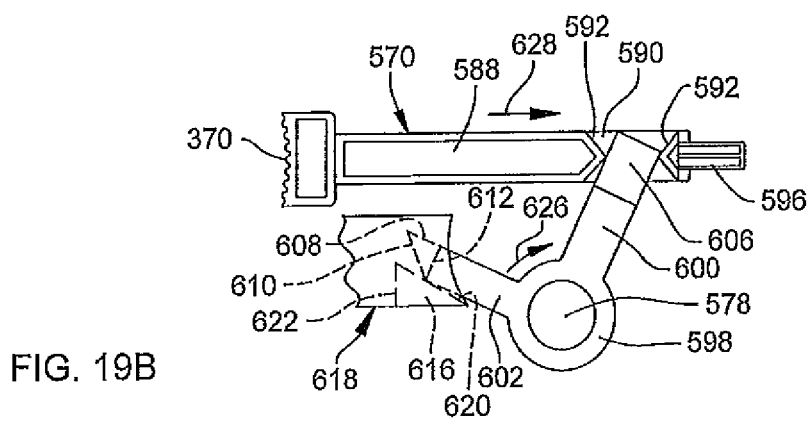
FIG. 19B is a partial sectional view illustrating interaction between the inflow cassette and the ejection housing section of the inflow cassette receptacle assembly of the pump of the present invention as the inflow cassette is being loaded into the pump.
Figure 19C:
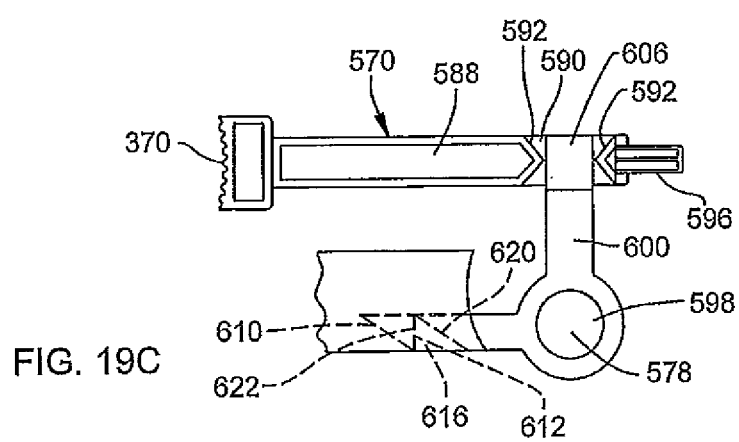
FIG. 19C is a partial sectional view illustrating interaction between the inflow cassette and the ejection housing section of the inflow cassette receptacle assembly of the pump of the present invention as the inflow cassette is loaded in the pump.

FIGS. 19A-19C illustrate the engagement between the lock lever 580 and the triangular lock block 616 as the inflow cassette 20 is inserted into the inflow cassette receiving area 402 of the inflow cassette receptacle assembly 394. As illustrated in FIG. 19A, as the inflow cassette 20 is inserted into the inflow cassette receiving area 402 of the inflow cassette receptacle assembly 394 along line 624 parallel to the insertion line, the abutment edge 620 of the triangular lock block 616 will abut the angled edge 610 of the triangular wedge 608 of the lock lever 580, causing the angled edge 610 of the triangular wedge 608 of the lock lever 580 to rise as illustrated in FIG. 19B and cause the lock lever 580 to rotate clockwise along arcuate line 626 about the cylindrical lock lever hub 578. Clockwise rotation of the lock lever 580 along arcuate line 626 causes the first arm 600 to push against the vertically aligned chevron-shaped side walls 592 in the rear channel 590 of the rod 588 to force the rod 588 of the ejection button mechanism 570 to move rearward along line 628 against the bias of the spring 582. Once the inflow cassette 20 is fully inserted into the inflow cassette receiving area 402 of the inflow cassette receptacle assembly 394, the abutment edge 620 of the triangular lock block 616 will no longer abut the angled edge 610 of the triangular wedge 608 of the lock lever 580. Since the triangular lock block 616 no longer abuts the triangular wedge 608 of the lock lever 580, the force of the spring 582 will push the rod 588 of the ejection button mechanism 570 back to the left as shown in FIG. 19C, causing the lock lever 580 to rotate counterclockwise along arcuate line 626 about the cylindrical lock lever hub 578. Once the triangular wedge 608 of the lock lever 580 abuts a bottom side wall of the bottom short substantially rectangular lock wedge movement area 564, the holding edge 612 of the triangular wedge 608 of the lock lever 580 will oppose the lock edge 622 of the triangular lock block 616 to prevent removal of the inflow cassette 20 from the inflow cassette receiving area 402 of the inflow cassette receptacle assembly 394.

In order to remove the inflow cassette 20 from the inflow cassette receiving area 402 of the inflow cassette receptacle assembly 394, the inflow cassette eject button 370 is depressed to cause movement of the ejection button mechanism 570 and the lock lever 580. First, depression of the inflow cassette eject button 370 will cause the ejection button mechanism 570 to move rearward along line 628 as illustrated in FIG. 19B, thereby forcing the vertically aligned chevron-shaped side walls 592 of the rear channel 590 in the rod 588 to push against the first arm 600 of the lock lever 580 and force the lock lever 580 to rotate clockwise along arcuate line 626 about the cylindrical lock lever hub 578. Once the holding edge 612 of the triangular wedge 608 of the lock lever 580 is above and not in front of the lock edge 622 of the triangular lock block 616 of the inflow cassette 20, the inflow cassette 20 will not be locked within the inflow cassette receiving area 402 of the inflow cassette receptacle assembly 394. The force of the peristaltic tubing 70 against the roller wheel 412 in the pump 14 and/or the force of the springs in the inwardly facing cassette feet receivers 444 and 557 will cause the inflow cassette 20 to move slightly out of the inflow cassette receiving area 402 of the inflow cassette receptacle assembly 394, thereby allowing the inflow cassette 20 to be easily grasped and removed from the inflow cassette receiving area 402 of the inflow cassette receptacle assembly 394. It is contemplated that the cassette feet receivers 444 and 557 can be formed without springs such that only the force of the peristaltic tubing 70 is used to eject the inflow cassette 20. Furthermore, the force of the spring 582 will force the lock lever 580 to rotate counterclockwise as discussed above, which will force the angled edge 610 of the triangular wedge 608 to move against the abutment edge 620 of the triangular lock block 616 of the inflow cassette 20, thereby forcing the inflow cassette 20 further out of the inflow cassette receiving area 402 of the inflow cassette receptacle assembly 394 as the two angled surfaces meet.

When the illustrated outflow cassette 26 is inserted through the outflow cassette door 372, the outflow cassette 26 is received within an outflow cassette receptacle assembly 630 (FIGS. 20 and 21) within the pump housing 354. The outflow cassette receptacle assembly 630 includes a motor housing section 632, an ejection housing section 634 and a center seal 636. The center seal 636 is sandwiched between the motor housing section 632 and the ejection housing section 634. An outflow cassette receiving area 638 is defined between the motor housing section 632 and the ejection housing section 634, with the outflow cassette 26 being inserted through the outflow cassette door 372 and into the outflow cassette receiving area 638.

In the illustrated example, the motor housing section 632 (FIGS. 20-22) of the outflow cassette receptacle assembly 630 works to pump the waste fluid through the outflow cassette 26. The motor housing section 632 includes a holding bracket 640, a pump motor 642, an outer housing member 644, pump motor seals 646, a roller wheel 648, a first device suction tubing stepper motor assembly 650, a second device suction tubing stepper motor assembly 652 and an outflow tube stepper motor assembly 654. The holding bracket 640 attaches the outflow cassette receptacle assembly 630 to the pump housing 354. The holding bracket 640 includes a plate 656 having a pair of top connection flanges 658 extending therefrom and a bottom foot 660. The bottom foot 660 rests on the bottom 362 of the pump housing 354 and fasteners are inserted through the connection flanges 658 and into the pump housing 354 to connect the outflow cassette receptacle assembly 630 to the pump housing 354. The plate 656 of the holding bracket 640 includes a circular motor opening 662 having a plurality of fastening openings 664 surrounding the circular motor opening 662. An L-shaped stepper motor connection flange 666 includes a first leg 668 extending rearwardly from a side edge of the plate 656 and a second leg 670 extending laterally from an end edge of the first leg 668. The second leg 670 of the L-shaped stepper motor connection flange 666 includes a top stepper motor opening 672 with adjacent top stepper motor fastener holes 674, a middle stepper motor opening 676 with adjacent middle stepper motor fastener holes 678, and a bottom stepper motor opening 680 with adjacent bottom stepper motor fastener holes 682. The L-shaped stepper motor connection flange 666 holds the first device suction tubing stepper motor assembly 650, the second device suction tubing stepper motor assembly 652 and the outflow tube stepper motor assembly 654 as discussed in more detail below.

The illustrated outer housing member 644 of the motor housing section 632 of the outflow cassette receptacle assembly 630 is configured to receive a portion of the outflow cassette 26 when the outflow cassette 26 is inserted into the outflow cassette receptacle assembly 630. The outer housing member 644 includes a panel 684 connected to the holding bracket 640. The panel 684 includes a rectangular recessed area 686 having a circular motor opening 688 and a plurality of fastening openings 690 surrounding the circular motor opening 688. When the outer housing member 644 is connected to the holding bracket 640, the circular motor opening 662 and the plurality of fastening openings 664 of the holding bracket 640 are aligned with the circular motor opening 688 and the fastening openings 690 of the outer housing member 644, respectively. A substantially circular flange 692 surrounds the circular motor opening 688 and substantially circular ridges 694 surround each of the fastening openings 690 in the rectangular recessed area 686 of the panel 684.

In the illustrated example, the outer housing member 644 includes a substantially C-shaped flange 696 extending perpendicularly from the panel 684 and defining a top, a bottom and an end of the portion of the outflow cassette receptacle assembly 630 defined by the motor housing section 632 of the outflow cassette receptacle assembly 630. The substantially C-shaped flange 696 includes a top leg 698, a bottom leg 700 and a rear leg 702. The top leg 698 and the bottom leg 700 each have diverging ends 704 opposite the rear leg 702 for allowing the outflow cassette 26 to be easily accepted into the outflow cassette receiving area 638 of the portion of the outflow cassette receptacle assembly 630 defined by motor housing section 632 of the outflow cassette receptacle assembly 630. The rear leg 702 includes a first half of inwardly facing cassette feet receivers 706 for accepting a portion of the inwardly facing feet 250 of the outflow cassette 26 therein when the outflow cassette 26 is inserted into the outflow cassette receptacle assembly 630 to assist in properly aligning the outflow cassette 26 within the outflow cassette receptacle assembly 630. While not shown, the first half of the inwardly facing cassette feet receivers 706 (along with corresponding inwardly facing cassette feet receivers 784 in the ejection housing section 634) can hold coil springs for assisting in pushing the outflow cassette 26 out of the outflow cassette receptacle assembly 630 when the outflow cassette eject button 374 is depressed. A plurality of connection flanges 708 extend outward from an outside face of the substantially C-shaped flange 696. The connection flanges 708 have fastener openings 710 therein for accepting fasteners 712 to connect the motor housing section 632 to the ejection housing section 398.

The illustrated pump motor 642 is connected to the holding bracket 640 and the outer housing member 644 and is configured to rotate the roller wheel 648. The pump motor 642 includes a motor housing 714 and an output shaft 716. The pump motor 642 has a power supply (not shown) connected thereto for rotating the output shaft 716. The motor housing 714 includes a plurality of fastener holes 718. The pump motor 642, the holding bracket 640 and the outer housing member 644 are connected together by first surrounding the holding bracket 640 with the pump motor seals 646. Each pump motor seal 646 includes a central circular opening 720 surrounded by fastener openings 722. The holding bracket 640, the outer housing member 644 and the pump motor seals 646 are aligned such that the circular motor opening 662 of the holding bracket 640, the circular motor opening 688 in the outer housing member 644, and the central circular opening 720 in the pump motor seals 646 are aligned and such that the fastening openings 664 in the holding bracket 640, the fastening openings 690 in the outer housing member 644, and the fastener openings 722 in the pump motor seals 646 are aligned. Fasteners are then inserted through the fastening openings 664 in the holding bracket 640, the fastening openings 690 in the outer housing member 644, the fastener openings 722 in the pump motor seals 646 and into the fastener holes 718 in the motor housing 714 to connect the pump motor 642 to the holding bracket 640 and the outer housing member 644. Once connected, the output shaft 716 of the pump motor 642 will extend through a center of the circular motor opening 662 of the holding bracket 640, the circular motor opening 688 in the outer housing member 644 and the central circular opening 720 in the pump motor seals 646.

In the illustrated example, the roller wheel 648 is rotated by the pump motor 642. The roller wheel 648 includes a first disc 726, a second disc 728, a shaft receptacle 730 and a plurality of roller cylinders 732. The roller cylinders 732 extend between and are connected to the first disc 726 and the second disc 728. The roller cylinder 732 can include a center post fixedly connected to the first disc 726 and the second disc 728 and an outer sleeve configured to be able to freely rotate on the center post. In the illustrated example, three roller cylinders 732 extend between the first disc 726 and the second disc 728 adjacent the peripheral edge thereof such that rotation of the first disc 726 and the second disc 728 will move the roller cylinders 732 along the same circular path. It is contemplated that any number of roller cylinders 732 (e.g., 3, 4, 5, etc.) could be used. Increasing the number of roller cylinders 732 can decrease pressure pulses in the peristaltic tubing, but a maximum flow rate of the fluid through the peristaltic tubing is decreased at higher RPMs of the roller wheel 648 as the number of roller cylinders 732 increases. The number of roller cylinders 732 and the RPM of the roller wheel 648 are used as inputs into the control system to control the outflow characteristics. The shaft receptacle 730 is located between the first disc 726 and the second disc 728 and is connected to at least one of the same. The shaft receptacle 730 is configured to receive the output shaft 716 of the pump motor 642 therein such that rotation of the output shaft 716 will cause rotation of the first disc 726 and the second disc 728 to thereby rotate the roller cylinders 732 in a circular path centered about the output shaft 716. It is contemplated that the output shaft 716 could have a non-circular cross-section to allow the output shaft 716 to be received within the shaft receptacle 730 of the roller wheel 648 to easily rotate the roller wheel 648. The first disc 726 of the roller wheel 648 sits on an edge of the substantially circular flange 692 extending around the circular motor opening 688 in the panel 684 of the outer housing member 644.

During use of the pump 14, the pump motor 642 will rotate the roller wheel 648 to push the waste fluid through the peristaltic tubing 256 of the outflow cassette 26 by having the roller cylinders 732 compress the peristaltic tubing 256 along a length thereof from a beginning of the peristaltic tubing 256 adjacent the ingress path section 260 towards the egress path section 262 of the interior fluid flow path 258. As discussed in more detail below, the output of the pump motor 642 (e.g., speed of output shaft 716) can be used to alter the flow rate and/or pressure of the waste fluid exiting the body cavity 12 (i.e., outflow characteristics). It is contemplated that the RPMs of the roller wheel 648 and a position of the roller wheel 648 and the roller cylinders 732 of the roller wheel 648 can be determined by any means. For example, an encoder coupled to the output shaft 716 of the pump motor 642 could include a Hall sensor and/or an optical reader to determine the position of the RPMs of the output shaft 716 (and the roller wheel 648) and the position of the output shaft 716 (and the roller wheel 648) in a manner well known to those skilled in the art.

In the illustrated example, the first device suction tubing stepper motor assembly 650, the second device suction tubing stepper motor assembly 652 and the outflow tube stepper motor assembly 654 are connected to the holding bracket 640. Each of the first device suction tubing stepper motor assembly 650, the second device suction tubing stepper motor assembly 652 and the outflow tube stepper motor assembly 654 includes a linear actuator 734, a rod 736 and a compression head 738. Each linear actuator 734 includes a connection plate 740 having a pair of fastener openings 742. The compression head 738 is connected to an end of the rod 736 extending away from the linear actuator 734 and the linear actuator 734 is configured to move the rod 736 and the compression head 738 linearly. A stepper motor assembly seal 744 is overlaid each face of the second leg 670 of the L-shaped stepper motor connection flange 666 of the holding bracket 640. Each stepper motor assembly seal 744 includes a top stepper motor opening 746 with adjacent top stepper motor fastener holes 748, a middle stepper motor opening 750 with adjacent middle stepper motor fastener holes 752, and a bottom stepper motor opening 754 with adjacent bottom stepper motor fastener holes 756.

Figure 21:
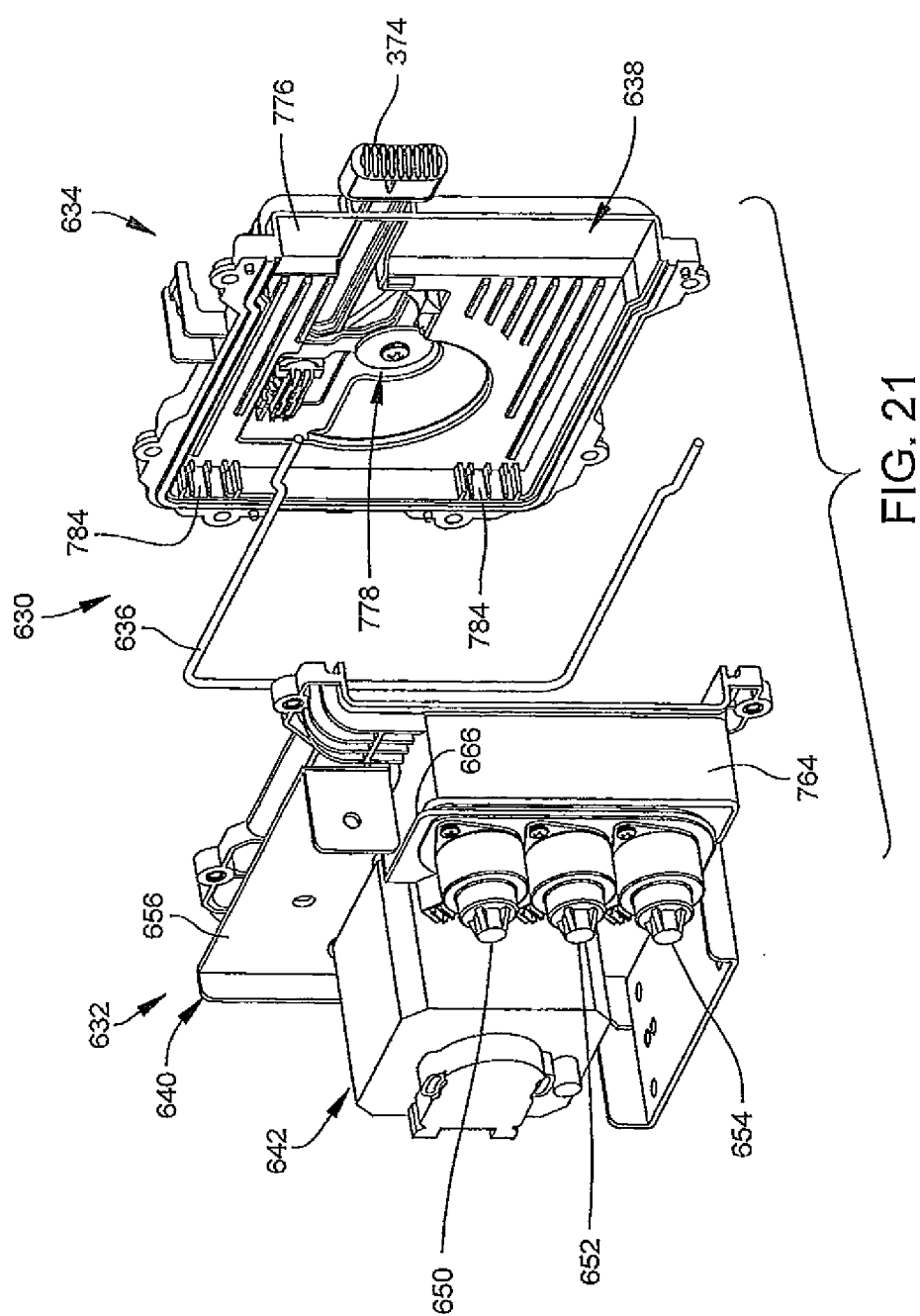
FIG. 21 is an exploded perspective view of the outflow cassette receptacle assembly of the pump of the present invention.
Figure 22:
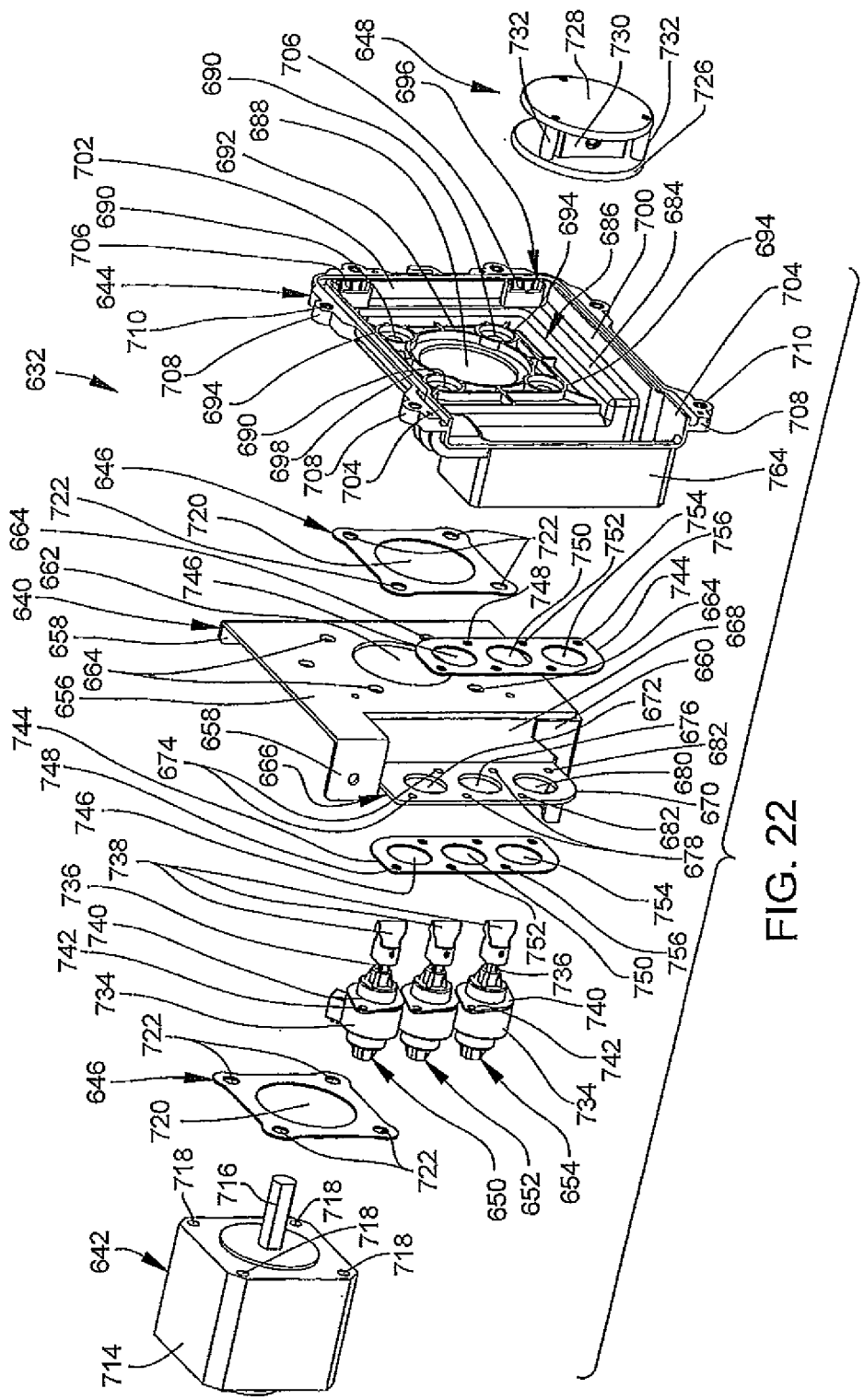
FIG. 22 is an exploded perspective view of a motor housing section of the outflow cassette receptacle assembly of the pump of the present invention.

As illustrated in FIGS. 20 and 21, fasteners 758 extend through fastener openings 742 in the connection plate 740 of the linear actuator 734 of first device suction tubing stepper motor assembly 650, the top stepper motor fastener holes 748 in each of the stepper motor assembly seals 744 and the top stepper motor fastener holes 674 in the second leg 670 of the L-shaped stepper motor connection flange 666 of the holding bracket 640 to connect the first device suction tubing stepper motor assembly 650 to the holding bracket 640. Likewise, fasteners 760 extend through fastener openings 742 in the connection plate 740 of the linear actuator 734 of second device suction tubing stepper motor assembly 652, the middle stepper motor fastener holes 752 in each of the stepper motor assembly seals 744 and the middle stepper motor fastener holes 678 in the second leg 670 of the L-shaped stepper motor connection flange 666 of the holding bracket 640 to connect the second device suction tubing stepper motor assembly 652 to the holding bracket 640. Moreover, fasteners 762 extend through fastener openings 742 in the connection plate 740 of the linear actuator 734 of the outflow tube stepper motor assembly 654, the bottom stepper motor fastener holes 756 in each of the stepper motor assembly seals 744 and the bottom stepper motor fastener holes 682 in the second leg 670 of the L-shaped stepper motor connection flange 666 of the holding bracket 640 to connect the outflow tube stepper motor assembly 654 to the holding bracket 640.

Once the first device suction tubing stepper motor assembly 650 is connected to the holding bracket 640, the rod 736 and the compression head 738 thereof will extend axially out of the top stepper motor opening 672. Likewise, once the second device suction tubing stepper motor assembly 652 is connected to the holding bracket 640, the rod 736 and the compression head 738 thereof will extend axially out of the middle stepper motor opening 676. Furthermore, once the outflow tube stepper motor assembly 654 is connected to the holding bracket 640, the rod 736 and the compression head 738 thereof will extend axially out of the bottom stepper motor opening 680. The rods 736 and the compression heads 738 are surrounded by a rectangular pocket 764 extending rearwardly from the panel 684 adjacent the rectangular recessed area 686 in the outer housing member 644.

In the illustrated example, the first device suction tubing stepper motor assembly 650, the second device suction tubing stepper motor assembly 652 and the outflow tube stepper motor assembly 654 are configured to prevent fluid flow through a first one of the device suction tubing 34, a second one of the device suction tubing 34 and the outflow tube 28, respectively. As illustrated in FIGS. 9 and 11, the bottom plate 268 of the outflow cassette 26 includes an elongated press ridge 766 located between the inverted U-shaped ingress tube connection members 288 and the open areas 292 in the interrupted U-shaped outer side wall 278. The bottom plate 268 can includes a plurality of mold holes 768 for allowing a mold to form the elongated press ridge 766 in a manner well known to those skilled in the art. The top frame 266 includes three access openings 770 in the top plate 276 above the elongated press ridge 766. The pump 14 is configured to selectively actuate the linear actuators 734 of the first device suction tubing stepper motor assembly 650, the second device suction tubing stepper motor assembly 652 and/or the outflow tube stepper motor assembly 654 to extend the rod 736 and compression head 738 thereof to pinch a first one of the device suction tubing 34, a second one of the device suction tubing 34 and/or the outflow tube 28, respectively, between the compression head 738 and the elongated press ridge 766, thereby preventing or restricting fluid flow through the first one of the device suction tubing 34, the second one of the device suction tubing 34 and/or the outflow tube 28, respectively. It is noted that the stepper motors (or any other motor configured to move the linear actuator) can be activated to pinch the suction tubing 34 and/or the outflow tube 28 to restrict flow of fluid therethrough without preventing all of the fluid passing therethrough (e.g., the motors moving the linear actuators can be configured to move the compression heads 738 to an infinite variety of positions). An alignment plate 772 extends upwardly from the bottom plate 268 between the elongated press ridge 766 and the open areas 292 in the interrupted U-shaped outer side wall 278. The alignment plate 772 includes three alignment grooves 774, with each alignment groove 774 accepting one of the first one of the device suction tubing 34, the second one of the device suction tubing 34 or the outflow tube 28 therein for preventing movement of the first one of the device suction tubing 34, the second one of the device suction tubing 34 and the outflow tube 28 during pinching thereof.

The illustrated ejection housing section 634 of the outflow cassette 26 maintains the outflow cassette 26 within the outflow cassette receiving area 638 to allow the pump motor 642 to pump the waste fluid through the outflow cassette 26. The ejection housing section 634 includes an inner housing member 776 and a locking assembly 778. The inner housing member 776 works with the outer housing member 644 of the motor housing section 632 of the outflow cassette receptacle assembly 630 to hold the outflow cassette 26 and the locking assembly 778 locks the outflow cassette 26 within the outflow cassette receptacle assembly 630. The ejection housing section 634 is an identical mirror image of the ejection housing section 398 of the inflow cassette receptacle assembly 394. The ejection housing section 634 of the outflow cassette receptacle assembly 630 functions identically to the ejection housing section 398 of the inflow cassette receptacle assembly 394, and works with a triangular lock block 780 located in a locking indentation 782 in the rear of the bottom plate 268 of the outflow cassette 26 to maintain the outflow cassette 26 within the outflow cassette receiving area 638 in the same manner that the ejection housing section 398 of the inflow cassette receptacle assembly 394 works with the triangular lock block 616 of the inflow cassette 20 to maintain the inflow cassette 20 within the inflow cassette receiving area 402. Accordingly, a detailed discussion of the ejection housing section 634 of the outflow cassette 26 is not required. The ejection housing section 634 of the outflow cassette 26 can include an RF antenna (not shown) on an outer face thereof for receiving the information on the RF chip 347 in the outflow cassette 26. The RF antenna communicates the information on the RF chip 347 to the control system of the pump 14.

FIG. 23 illustrates the foot pedal 44 of the pump system 10. The foot pedal 44 can include a pair of foot actuators 788. The foot actuators 788 can be depressed for turning the pump or systems thereof on and off and adjust pump settings such as pressure and flow. Software for the pump 14 can allow for the foot pedal to be configured according to user preferences. For example, the foot actuators 788 can be depressed to activate or deactivate the fluid flow through the inflow cassette 20 and/or the outflow cassette 26. The foot pedal 44 also includes a communication cord 790 having a input end 792 configured to be inserted into the 8 pin foot pedal port 382 in the pump 14 to connect the foot pedal 44 to the pump 14. It is also contemplated that the foot pedal 44 can be wired to the pump 14 (or control system thereof) in other manners or can wirelessly communicate with the pump 14 (or control system thereof).

FIG. 24 illustrates the remote control 46 of the pump system 10. The remote control 46 includes a plurality of buttons 794 for controlling basic functionality of the pump 14. For example, the buttons 794 can make the pump 14 provide more or less pressure in the surgery washing fluid, provide more or less suction of the waste fluid, turn the pump 14 on and off, and swap between different hardware settings (e.g., scope/cannula combinations) to allow for a surgeon to switch the scope and/or cannula being used without stopping the pump 14 and having to re-calibrate or re-select for new hardware. The remote control 46 can include a communication cord (not shown) having a input end 792 configured to be inserted into the 8 pin remote port 384 in the pump 14 to connect the remote control 46 to the pump 14. It is also contemplated that the remote control 46 can be wired to the pump 14 (or control system thereof) in other manners or can wirelessly communicate with the pump 14 (or control system thereof).

Figure 25A:
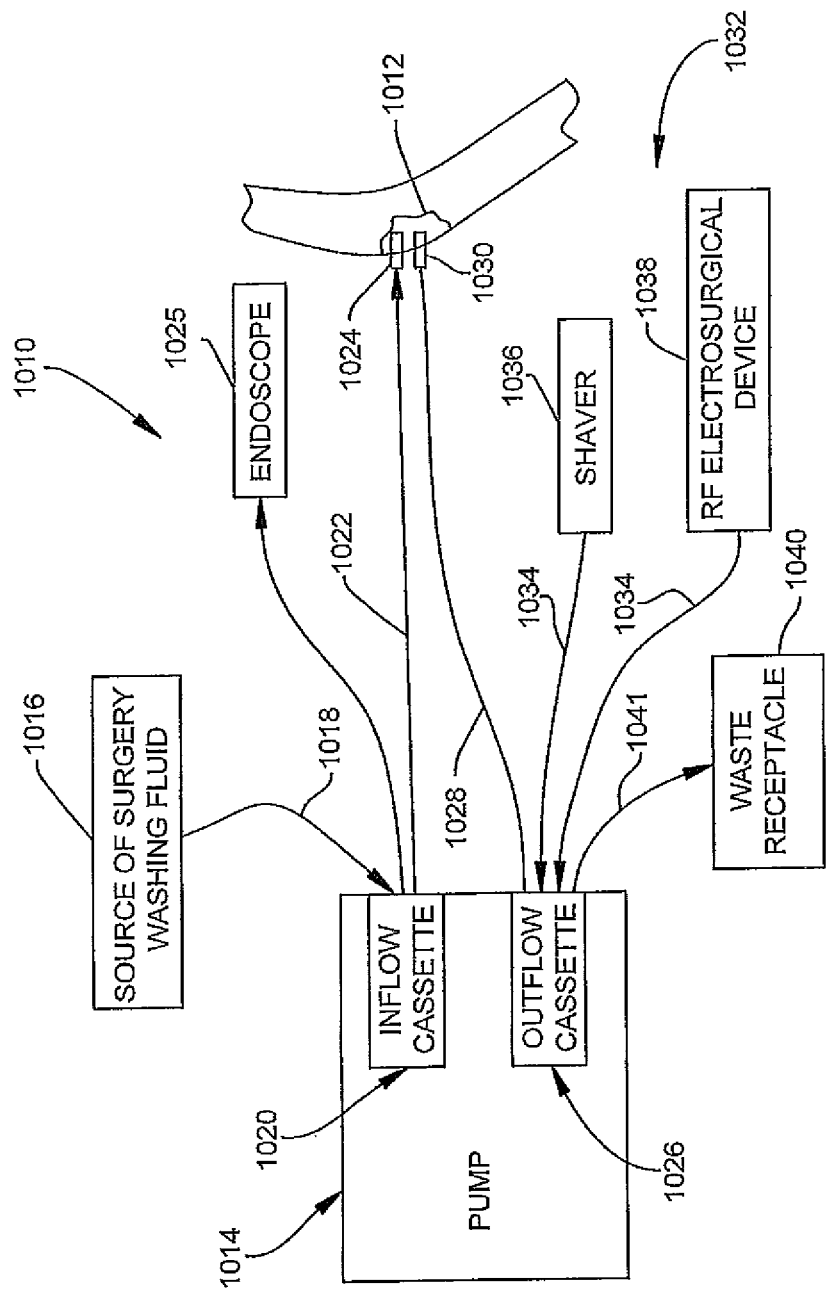
FIG. 25A is a schematic view of an embodiment of a pump system of the present invention illustrating flow paths through the pump system.

Referring to FIG. 25A, there is illustrated another embodiment of the pump system 1010 of the present invention illustrating flow paths through the pump system. The embodiment illustrated in FIG. 25A and discussed below incorporates features from the earlier described embodiments and is not mutually exclusive therefrom. Thus, the embodiments discussed above are within the scope of the embodiments discussed hereinafter. Specifically, the following elements described above can be used in the present embodiment and are identified in the present embodiment by adding 1000 to the numbering scheme (e.g., the pump 14 described above can be a pump 1014 described in the present embodiment): the pump system 10, the pump 14, the source of surgery washing fluid 16, the input tubing 18, the inflow cassette 20, the inflow tube 22, the inflow cannula 24, the outflow cassette 26, the outflow tube 28, the outflow cannula 30, the surgery device 32, the device suction tubing 34, the shaver 36, the RF ablation device 38 that cuts or coagulates tissue, the waste receptacle 40, the waste tubing 41, the integration system 42, the foot pedal 44, the remote control 46, the inflow information 48, the outflow information 50 and the input device 52. The integration system 42 identified above could also be used as a multi-device operating room controller 1043 of the present embodiment.

The pump system 1010 includes the pump 1014 configured to provide a surgery washing fluid to a body cavity 1012 (e.g., a joint) during surgery and to suction waste fluid out of the body cavity 1012.

As illustrated in FIG. 25A, the pump 1014 receives a surgery washing fluid from a source of surgery washing fluid 1016. Input tubing 1018 connects between the source of surgery washing fluid 1016 and the pump 1014 for supplying the surgery washing fluid. As illustrated in FIG. 25A, the pump 1014 can have an inflow cassette 1020 inserted therein for receiving the surgery washing fluid and for pushing the surgery washing fluid to the body cavity 1012 through an inflow tube 1022. Typically, the inflow tube 1022 is inserted into and/or connected to an inflow cannula 1024 inserted into the body cavity 1012. In some embodiments, an endoscope 1025 can be utilized with the inflow cannula 1024 to provide washing fluid to the body cavity 1012.

The illustrated pump 1014 can also have an outflow cassette 1026 inserted therein for suctioning fluid out of the body cavity 1012. An outflow tube 1028 extends between the body cavity 1012 and the outflow cassette 1026, with the outflow tube 1028 typically inserted into and/or connected to an outflow cannula 1030 inserted into the body cavity 1012. Device suction tubing 1034 can connect the outflow cassette 1026 to one or more surgery devices 1032 (which can be a cutting device). The surgery devices 1032 are configured to suction the fluid out of the body cavity 1012 while the surgery devices 1032 are being used within the body cavity 1012. The surgery devices 1032 can include a shaver 1036 having a shaver processor 1037, an RF electrosurgical probe device or ablation device 1038 having an electrosurgical device processor 1039, or any other surgery device that can suction waste fluid out of the body cavity 1012. The outflow cassette 1026 is connected to a waste receptacle 1040 by waste tubing 1041.

Figure 25B:
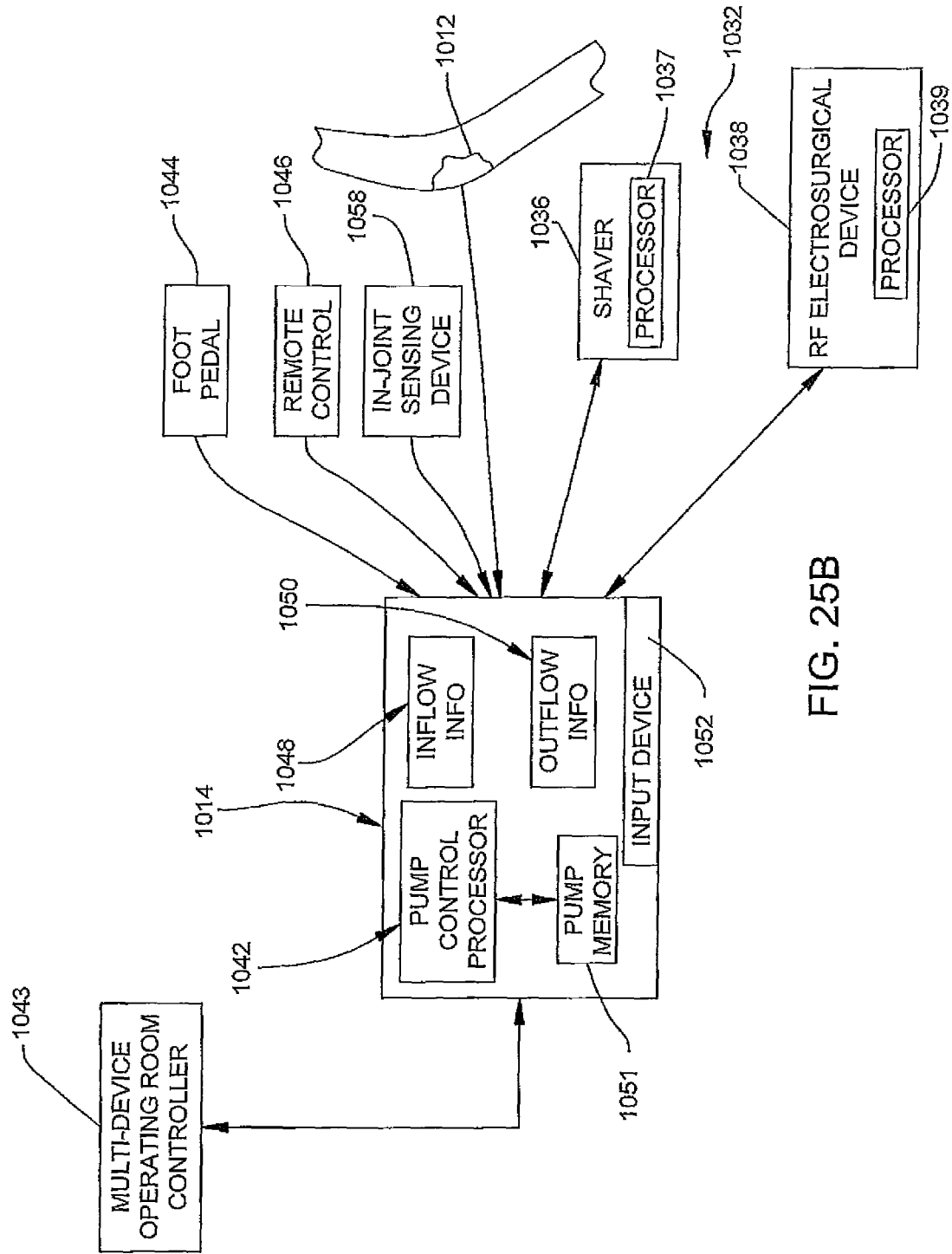
FIG. 25B is a schematic view of the pump system embodiment of FIG. 25A illustrating communication paths through the pump system.

In the illustrated example, the pump system 1010 can receive information from various elements of the pump system to change the flow rate and/or pressure of the surgery washing fluid being provided to the body cavity 1012 (i.e., inflow characteristics) and/or to change the flow rate and/or pressure of the waste fluid being suctioned from the body cavity 1012 (i.e., outflow characteristics). FIG. 25B illustrates the information paths between various elements of the pump system 1010. In the illustrated example, the pump 1014 includes a pump control processor 1042, such as a microprocessor, that includes programs and/or algorithms for altering the inflow and/or outflow characteristics of the pump 1014. The pump control processor 1042 can obtain information from the body cavity 1012 (e.g., pressure and temperature within the body cavity 1012), the cassettes 1020, 1026, the surgical device processors of the surgical devices 1032 (e.g., the shaver processor 1037 and/or the RF electrosurgical device processor 1039), the multi-device operating room controller 1043 capable of controlling plural surgery devices including the pump 1014, a foot pedal 1044, a remote control 1046, inflow information 1048 measured within the pump 1014 including pressure head information for the fluid output from the pump 1014 and outflow information 1050 including pressure information of the outflow fluid suctioned from the surgical site in the joint by the pump 1014. In some embodiments, an in-joint sensing device 1058 is provided to directly sense temperature and/or pressure at the surgical site in a joint. The pump 1014 can include a pump memory device 1051 that stores information received by the pump control processor 1042 and can prestore information regarding various devices, such as the cassettes, the surgical devices and various cutting accessories. The pump 1014 can also include an input interface or input device 1052 for inputting information directly to the pump (e.g., a keyboard or touch screen).

Figure 26:
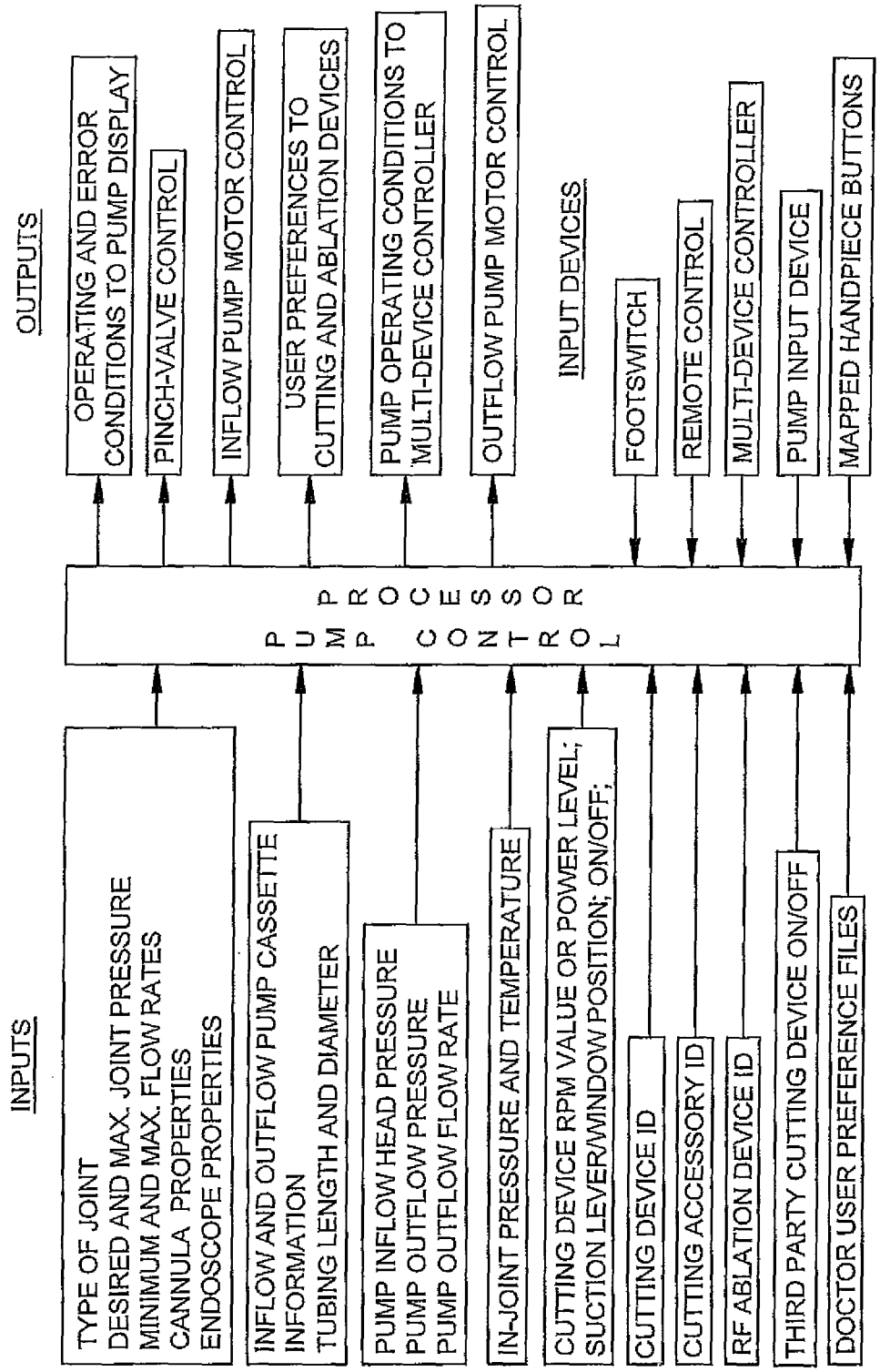
FIG. 26 is a block diagram showing inputs provided to the pump control processor and outputs from the pump control processor.

FIG. 26 illustrates various inputs, outputs and input devices that are provided with a pump control processor 1042. The input devices include the multi-device operating room controller 1043, the foot pedal 1044, the remote control 1046 and the pump input device 1052.

In various embodiments, only some of the inputs shown in FIG. 26 are provided to the pump control processor 1042 and only selected ones of the outputs are output therefrom. For example, in some embodiments of the invention there is no outflow pump motor control. In other embodiments, an unidentified third party surgical device is provided, wherein the pump control processor 1042 does not know device parameters of such a surgical device. Many embodiments of the invention do not include an in-joint pressure sensor or an in-joint temperature sensor, and thus such directly measured joint pressure values are not provided to the pump control processor 1042. In some embodiments, a multi-device operating room controller 1043 is not connected to the pump system 1010. Further, additional inputs and outputs for the pump control processor 1042 that are not shown in FIG. 26 are also contemplated.

In the embodiments discussed above, only inflow fluid flow control is provided by the pump 1014 and the pump control processor 1042 to initially maintain a constant desired in-joint pressure ($P_{joint}$) without the use of an in-joint pressure sensor. In other embodiments, inflow/outflow fluid control is provided by the pump 1014 and the pump joint pressure is again maintained without an in-joint pressure sensor.

Identified Components:

In one embodiment, the type of inflow cannula 1024, type of endoscope 1025, and the type of inflow tube 1022 and length thereof are identified. Identification information for each of the components is input into the pump control processor 1042 manually or automatically. The dimensions and length of the inflow and outflow tubing that is secured to the pump cassettes 1020, 1026, along with other properties, is typically automatically read by RF communication or identified by the pump control processor 1042 when the inflow and outflow cassettes 1020, 1026 are inserted into the pump 1014.

The pump control processor 1042 utilizes stored or read dimensions and other values for the known identified components to calculate a pressure loss ($P_{loss}$) curve based on the dimensions and characteristics of the inflow tubing 1022, the inflow cannula 1024 and the endoscope 1025 that define an inflow path to the surgical site 1012 in the joint. Details for the inflow tubing, the endoscope 1025 and the inflow cannula 1024 can be stored in pump memory 1051. An algorithm or program executed by the pump control processor 1042 calculates coefficients ($COEF_1$ and $COEF_2$) defining the $P_{loss}$ curve from the properties including the dimensions and length of the tubing 1022, and properties including dimensions of both the cannula 1024 and the endoscope 1025. The coefficients are provided in an equation including speed or velocity, typically revolutions per minute (RPMs) of an inflow pump motor to calculate a $P_{loss}$ value at a point on the $P_{loss}$ curve as defined for a given inflow pump motor speed.

Obtaining a $P_{loss}$ value on the $P_{loss}$ curve for an RPM value of the inflow pump motor requires an algorithm or program calculating a second order polynomial using the load coefficients $COEF_1$, $COEF_2$ as set forth in the following equation:

$$P_{loss} = COEF_1 \times (RPM\ value)^2 + COEF_2 \times (RPM\ value).$$

The above pressure loss equation results in a calculated $P_{loss}$ value at a given RPM value for the inflow motor of the pump system.

A measured head pressure ($P_{head}$) sensed by a pump inflow pressure sensor of the pump 1014 disposed at or near the inflow pump cassette 1020 is used to calculate the in-joint pressure using the following equation:

$$P_{joint} = P_{head} - P_{loss}$$

Using the above calculation, the pump control processor 1042 The pump control processor 1042 controls the inflow pump controls the inflow pump motor to maintain the $P_{joint}$ value at a generally constant predetermined desired pressure value regardless of the outflow arrangement.

The pump control processor 1042 controls the inflow pump motor over a range in which there is a linear relationship between the inflow flow rate (Inflow) and the inflow pump motor RPM value using the following equation:

$$Inflow = COEF_{INFL} \times (RPM\ value).$$

The inflow coefficient $COEF_{INFL}$ value is loaded from a look-up table for the identified hardware (cannula, inflow tubing, etc.) connected to the pump.

In some embodiments, an inflow cannula provides fluid to a joint without an endoscope. In such an instance, the pump control processor 1042 simply determines the load coefficients and inflow coefficient from the inflow tubing and the inflow cannula. In other embodiments the cannula is an outflow cannula or a different cannula.

In operating the pump system, location of the inflow cannula 1024 at the surgical site 1012 in the joint and adequate flow of inflow fluid to the surgical site in the joint is determined to avoid providing flow when the inflow cannula is not disposed in the joint and to prevent a high pressure when there is low flow with the cannula disposed in the joint. Finally, incorrectly identified components, such as an inflow cannula, an endoscope or other components, along with erroneous information provided to the pump control processor 1042 is determined to prevent the pump system from applying high fluid pressure to a joint.

Joint Test Routine:

From the identified components, such as the inflow cannula and the endoscope provided with the cannula and the length and diameter of the tubing, the pump control processor 1042 determines a $P_{head}$ cannula in-joint value, a $P_{head}$ flow test value, a time in-joint value and a time low flow value.

Figure 27:
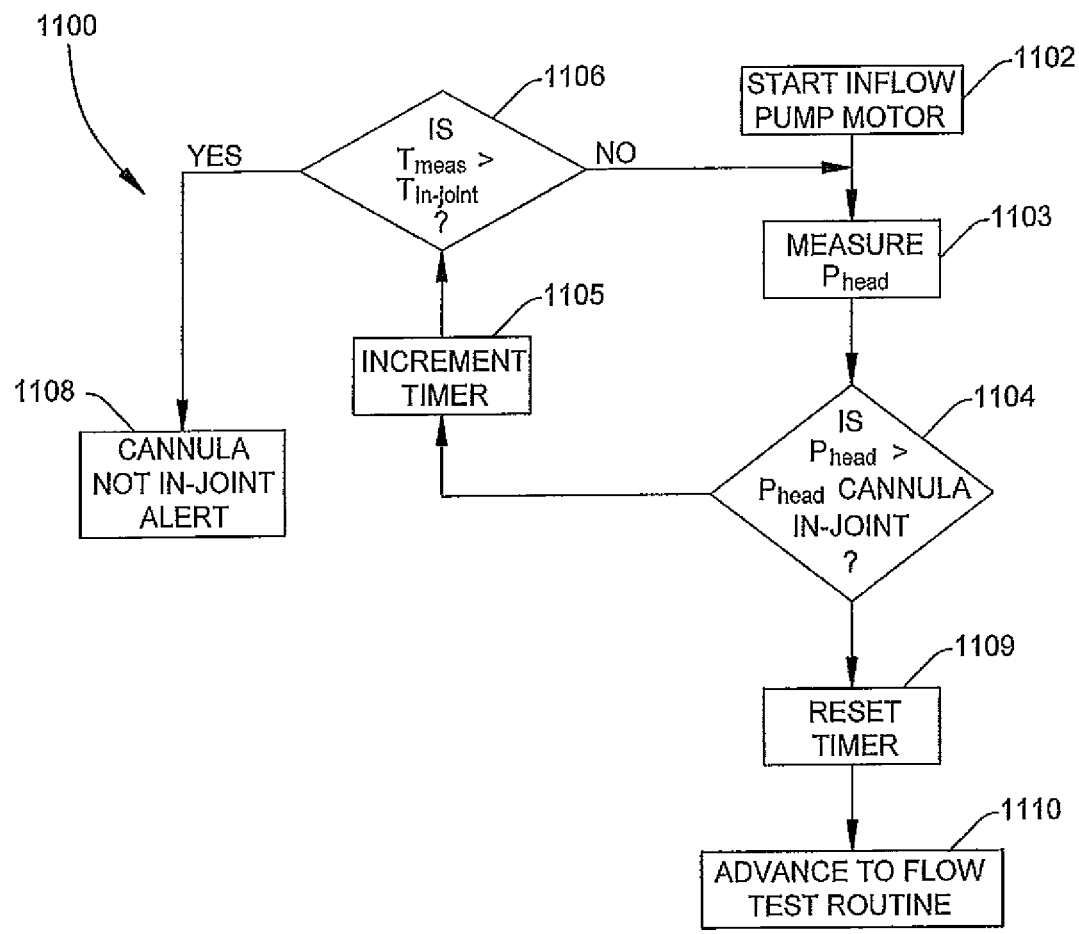
FIG. 27 is a flowchart of a pump system operating routine that determines if a cannula is disposed at a surgical site in a joint.

FIG. 27 shows a cannula in-joint test routine 1100 for the pump system. The cannula in-joint test routine 1100 executes as follows. At step 1102, the pump control processor 1042 drives the inflow pump motor at a cannula in-joint test RPM value. At step 1103, $P_{head}$ is measured by the inflow pressure sensor. At step 1104, measured $P_{head}$ is compared with a $P_{head}$ cannula in-joint value. When $P_{head}$ is not greater than $P_{head}$ cannula in-joint value, the routine 1100 advances to step 1105 whereat the timer is incremented from a zero time start value. The routine 1100 then advances to step 1106 and the incremented measured time is compared with a time in-joint value. So long as the measured time value is not greater than the predetermined time in-joint value, the routine 1100 returns to step 1103 whereat $P_{head}$ is again measured.

At step 1104, $P_{head}$ is again compared with the $P_{head}$ cannula in-joint value. If $P_{head}$ is again greater than $P_{head}$ cannula in-joint, the routine 1100 again advances to step 1105 whereat the timer is incremented, and then advances to step 1106.

At step 1106, if the measured time is greater than time in-joint, the joint test routine 1100 advances to step 1108. At step 1108, the pump control processor 1042 outputs a cannula not in-joint alert to indicate that the inflow cannula is not properly placed at a surgical site in a joint. Typically, the inflow pump motor also is stopped.

Figure 28:
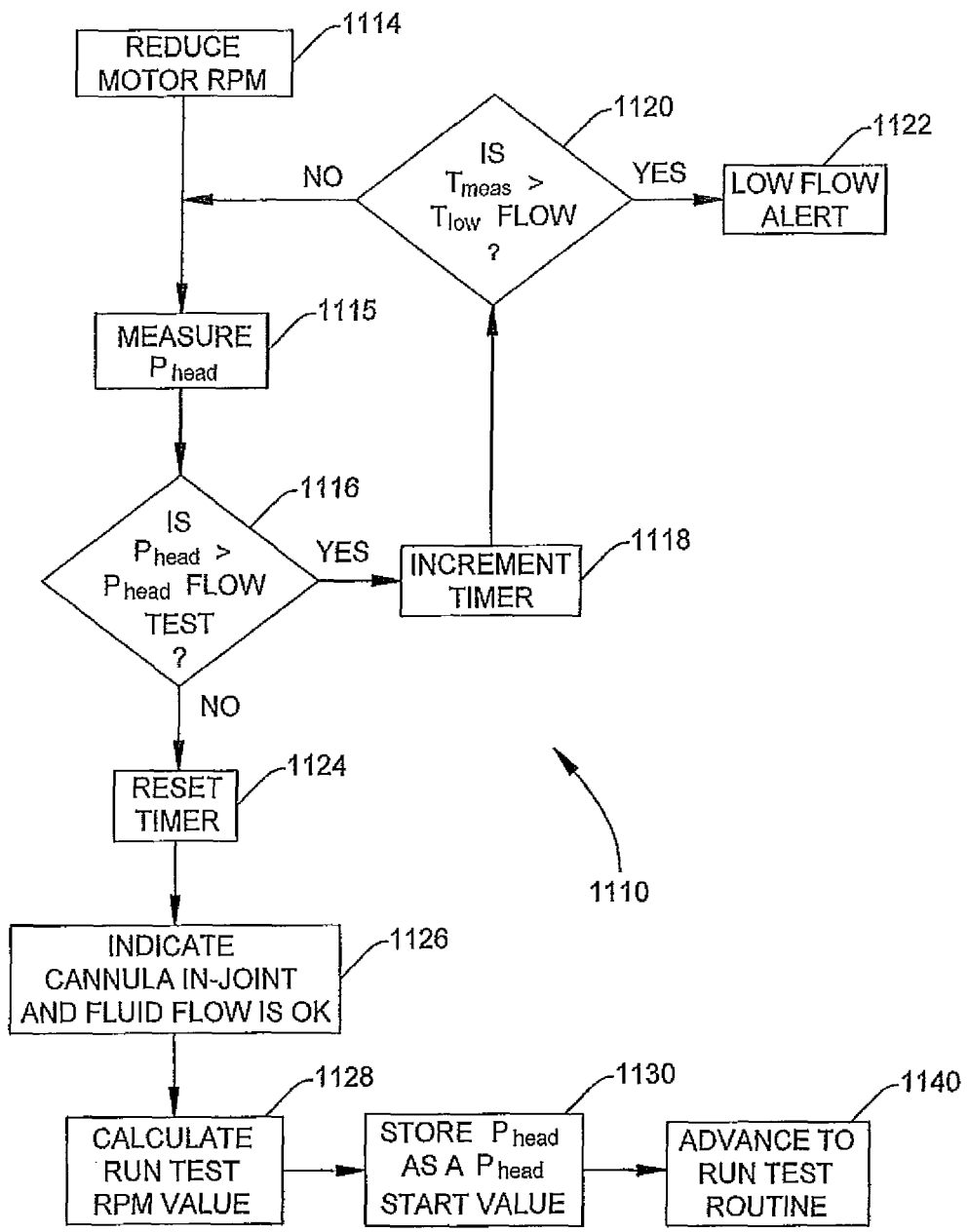
FIG. 28 is a flowchart of a pump system operating routine that determines whether a minimum fluid flow is provided to a surgical site in a joint.

Returning to step 1104, when measured $P_{head}$ is greater than the $P_{head}$ cannula in-joint value, the inflow cannula is disposed in the joint of a patient. The routine 1100 then advances to step 1109 whereat the timer of the pump control processor 1042 is reset. The joint test routine 1100 advances to flow test routine 1110 shown in FIG. 28.

Flow Test Routine:

At step 1114 of the flow test routine 1110, the inflow motor is reduced to a flow test RPM value for determining if there is adequate flow through the cannula and into the surgical site at the joint. The flow test RPM value, the $P_{head}$ flow test value and the low flow time value are previously determined by the pump control processor 1042 based on the identified hardware and any other relevant information. From step 1114, the flow test routine 1110 advances to step 1115 whereat $P_{head}$ is measured. The flow test routine 1110 then advances to step 1116, whereat the pump control processor 1042 determines if measured $P_{head}$ is greater than $P_{head}$ flow test. If $P_{head}$ is greater than $P_{head}$ flow test, the routine 1110 advances to step 1118 whereat the timer is incremented. Then the routine 1110 advances to step 1120 whereat the measured and incremented time is compared with a low flow time ($T_{low\ flow}$). If the measured time is greater than the low flow time, the routine advances to step 1122, whereat the pump control processor 1042 provides a low flow alert to a user. Typically at step 1022 the inflow pump is also stopped to avoid the possibility of a high fluid pressure in the joint.

At decision step 1120, when the measured time is not greater than the low flow time the flow test routine 1100 returns to step 1115 whereat $P_{head}$ is measured. Then at step 1116, the pump control processor 1042 again determines if measured $P_{head}$ is greater than the $P_{head}$ flow test value. If measured $P_{head}$ is no longer greater than the $P_{head}$ flow test value, the routine 1100 advances to step 1124.

At step 1124, the timer of the pump control processor 1042 is reset or cleared and the flow test routine 1110 advances to step 1126. At step 1126, the pump control processor 1042 outputs an indication that the inflow cannula is disposed in the joint and that the fluid inflow through the cannula to a surgical site in the joint is greater than a predetermined minimum flow.

The flow test routine 1110 then advances to step 1128 and begins preparations for a pump system test to ensure the inflow cannula and endoscope are correctly identified. At step 1128, the routine calculates a run test RPM value based on a desired $P_{loss}$ curve in combination with the hardware, such as the inflow cannula, the endoscope, the tubing, and in some instances the type of joint and doctor preferences. Further, a $P_{head}$ end test value is determined by the pump control processor 1042.

At step 1130, the flow test routine 1110 stores a measured $P_{head}$ as a $P_{head}$ start value and resets the timer to provide a start time. The flow test routine 1110 then advances to the run test routine 1140 shown in FIG. 29.

Figure 29:
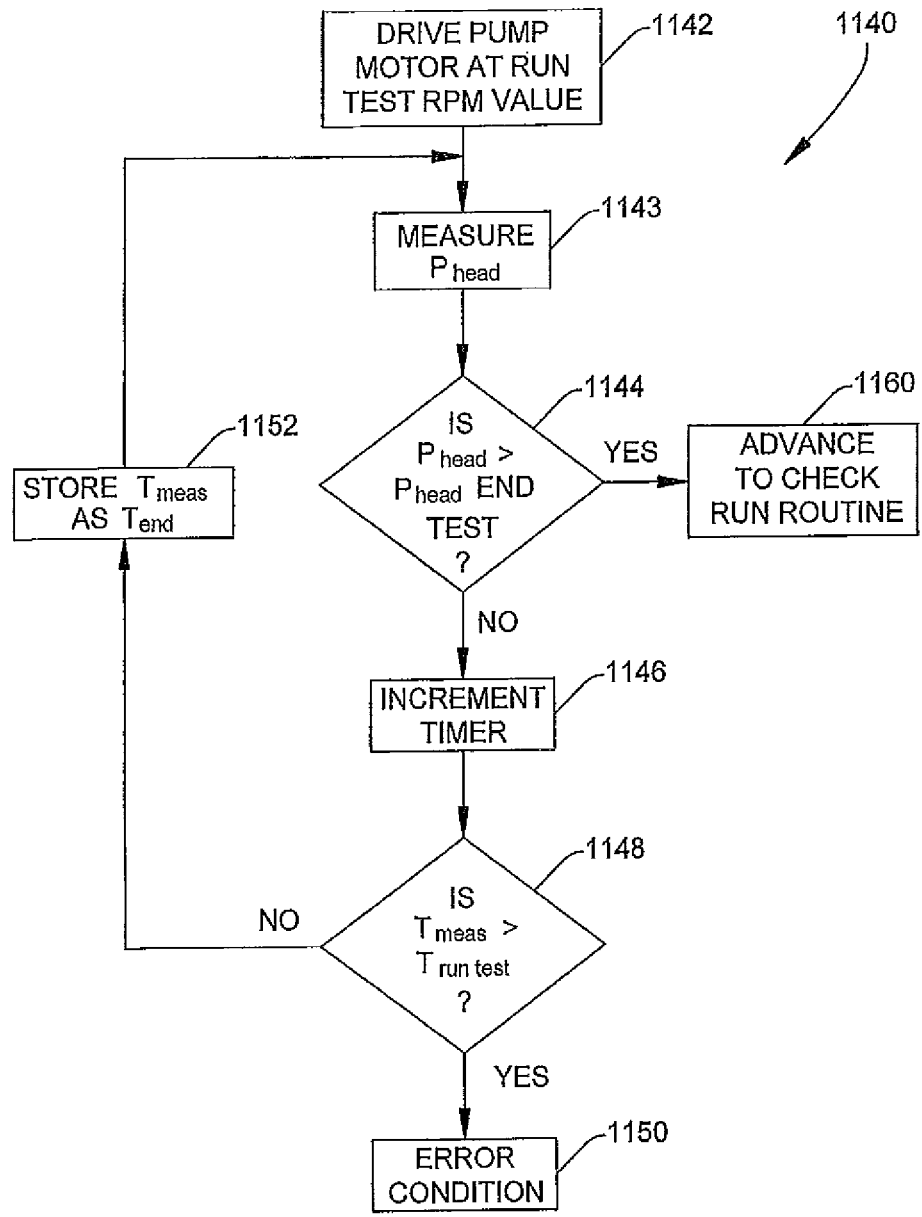
FIG. 29 is a flowchart of a pump system routine that measures head pressure values and time values over a time period.

Run Test Routine:

At a first step 1142 of the run test routine 1140 shown in FIG. 29, the pump motor 406 is driven at the run test RPM value. The routine 1140 advances to step 1143 whereat $P_{head}$ is measured by the inflow pressure sensor. The run test routine 1140 advances to step 1144, whereat measured $P_{head}$ is compared with the $P_{head}$ end test value. When the measured $P_{head}$ is not greater than the $P_{head}$ end test value, the routine 1140 advances to step 1146.

At step 1146, the timer is incremented to provide a measured time value. The routine 1140 advances to decision step 1148 whereat the incremented and measured time is compared with a time run test value. If the measured time ($T_{meas}$) is greater than the time run test value, the routine 1140 advances from step 1148 to step 1150 whereat an error condition is output by the pump control processor 1042.

If the measured time at step 1148 is not greater than the run test time, the routine 1140 advances from step 1148 to step 1152 whereat the incremented time is stored as an end time value (T end). Thereafter, the routine 1140 again measures $P_{head}$ at step 1143 and then returns to decision step 1144. At step 1144, once again the routine 1140 determines whether measured $P_{head}$ is greater than the $P_{head}$ end test value. If $P_{head}$ is not greater than $P_{head}$ end test, the routine 1140 again advances to steps 1146, 1148 and operates as set forth above. When measured $P_{head}$ is greater than the $P_{head}$ end test value at decision step 1144, however, the routine 1140 advances to check run routine 1160 illustrated in FIG. 30.

Figure 30:
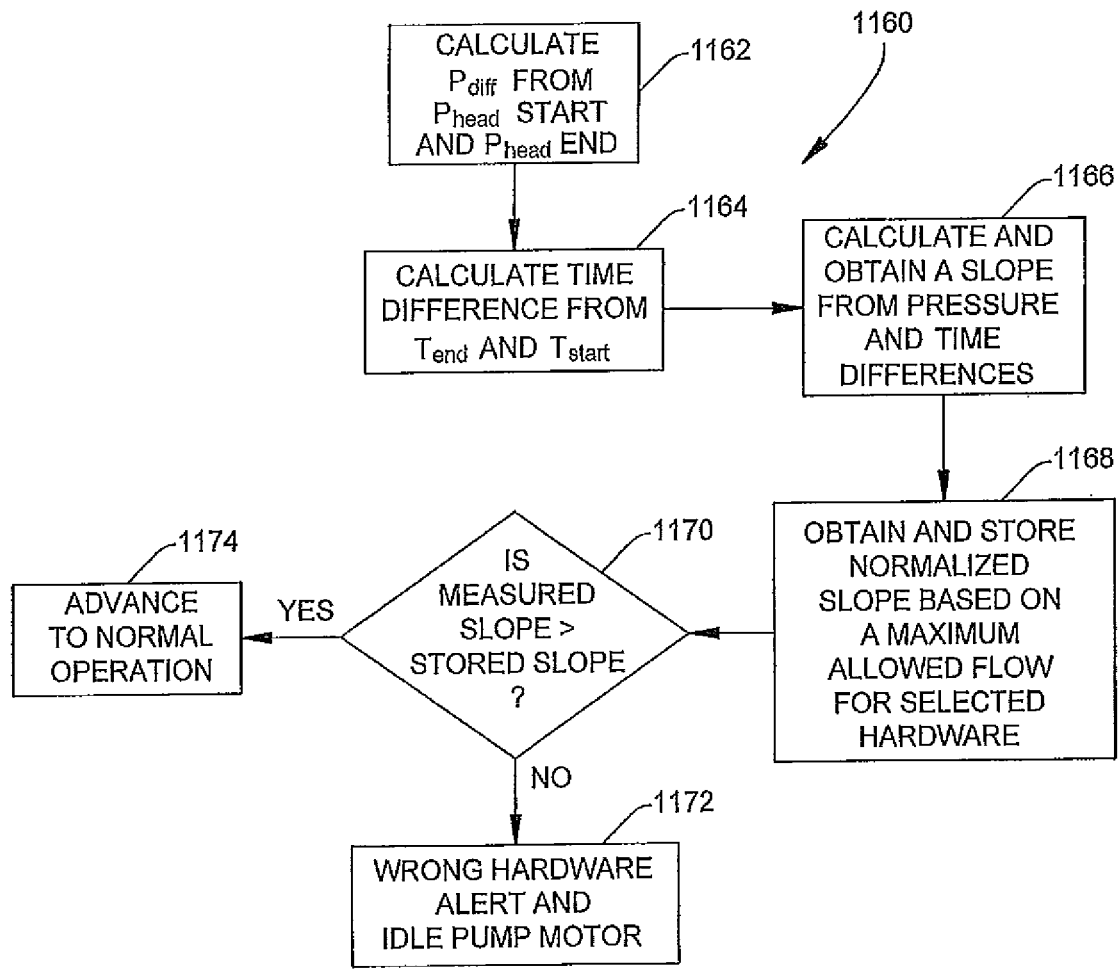
FIG. 30 is a flow chart of a pump system operating routine that calculates slope from the head pressure values and the time values measured by the FIG. 29 routine and determines if the pump system is provided with incorrect hardware.

Check Run Routine:

The check run routine 1160 shown in FIG. 30 performs a number of calculations to the pressure and time data obtained by the run test routine 1140. At step 1162 of the check run routine 1160, the pump control processor 1042 calculates a pressure difference from the $P_{head}$ start value and the $P_{head}$ end value. The check run routine 1160 then advances to step 1164 whereat the pump control processor 1042 calculates a time difference from the stored start time and the stored end time.

The check run routine 1160 then advances to step 1166 whereat the pump control processor 1042 calculates and obtains a calculated or measured slope from the measured pressure and time differences. The routine 1160 then advances to step 1168. At step 1168, the pump control processor 1042 calculates and stores a normalized slope based on a maximum allowed flow for the identified hardware connected to the pump. This step of calculating and storing a slope can occur at any time, including before beginning operation of the check run routine 1160. The routine 1160 then advances to step 1170.

At step 1170, the measured slope obtained from the measured pressure and measured time values is compared with the stored normalized slope. When the measured slope is not greater than the stored slope, the check run routine 1160 advances to step 1172. At step 1172, an incorrect identification hardware alert is provided by the pump control processor 1042 and typically the inflow pump motor is idled. Idling the pump motor prevents the possibility of an overpressure condition at a surgical site in a joint of a patient.

When the measured slope is greater than the stored slope, the routine 1160 advances to step 1174. From step 1174, the routine 1160 advances to normal operation of the pump system based on the identified inflow cannula, the identified endoscope and in some instances, the tubing connecting the pump cassette to the cannula. Other information such as joint type and user preferences may also be a factor as discussed above. Thus, the routines 1140, 1160 are executed to provide a check test to confirm that the hardware connected to the pump is correctly identified, and in some instances, to avoid overpressure in the joint.

In conclusion, the joint test routine 1100, the flow test routine 1110, the run test routine 1140 and the check run routine 1160 provide a redundancy to confirm that the pump system is properly connected to the surgical site, that adequate fluid flow is being provided to the surgical site, and that the hardware secured to the pump is properly identified.

Recognized Surgical Device:

As shown in FIG. 25B, a shaver 1036 and/or RF electrosurgical probe device 1038 is connected to the pump 1014, preferably via a two-way communication bus. Surgical devices 1032 manufactured by the manufacturer of the pump system 1010 recognize each other's signals and thus are capable of two-way communication. Thus, performance parameters of surgical devices 1032 and cutting accessories can be communicated to the pump control processor 1042. In some embodiments for a shaver 1036, parameters including shaver identification information and identification information including the type and size of bur or other surgical device accessory disposed on the shaver is provided automatically to the pump control processor 1042. Further, the ON/OFF condition, the specific cutter or bur used, the type of operating mode selected for the shaver (examples are Forward, Reverse, Oscillation, etc.), the real-time RPM value of a shaver motor during operation, and other properties can be provided to the pump control processor 1042 via the communication bus to optimize the performance of the pump 1014. Further, a window size and window position of a surgical device and/or cutting accessory can be provided to the pump control processor 1042.

With regard to an RF electrosurgical device or RF probe, parameters such as identification information for an RF electrosurgical device handpiece, the ON/OFF condition thereof, the type of RF probe, identification information including suction and non-suction parameters, and the RF power level output setting can be provided automatically to the pump control processor 1042 for optimizing operation of the pump 1014.

In some embodiments, the dimensions of a flow path through a surgical device handpiece and the position of a lever controlling flow through the path can be provided over the communication bus to the pump control processor 1042. In some embodiments surgical device identifiers and cutting accessory identifiers are sent over the communication bus to the pump control processor 1042 and values for the bur size, window size, and flow path dimensions that are previously stored in the pump memory 1051 can be retrieved.

Figure 31:
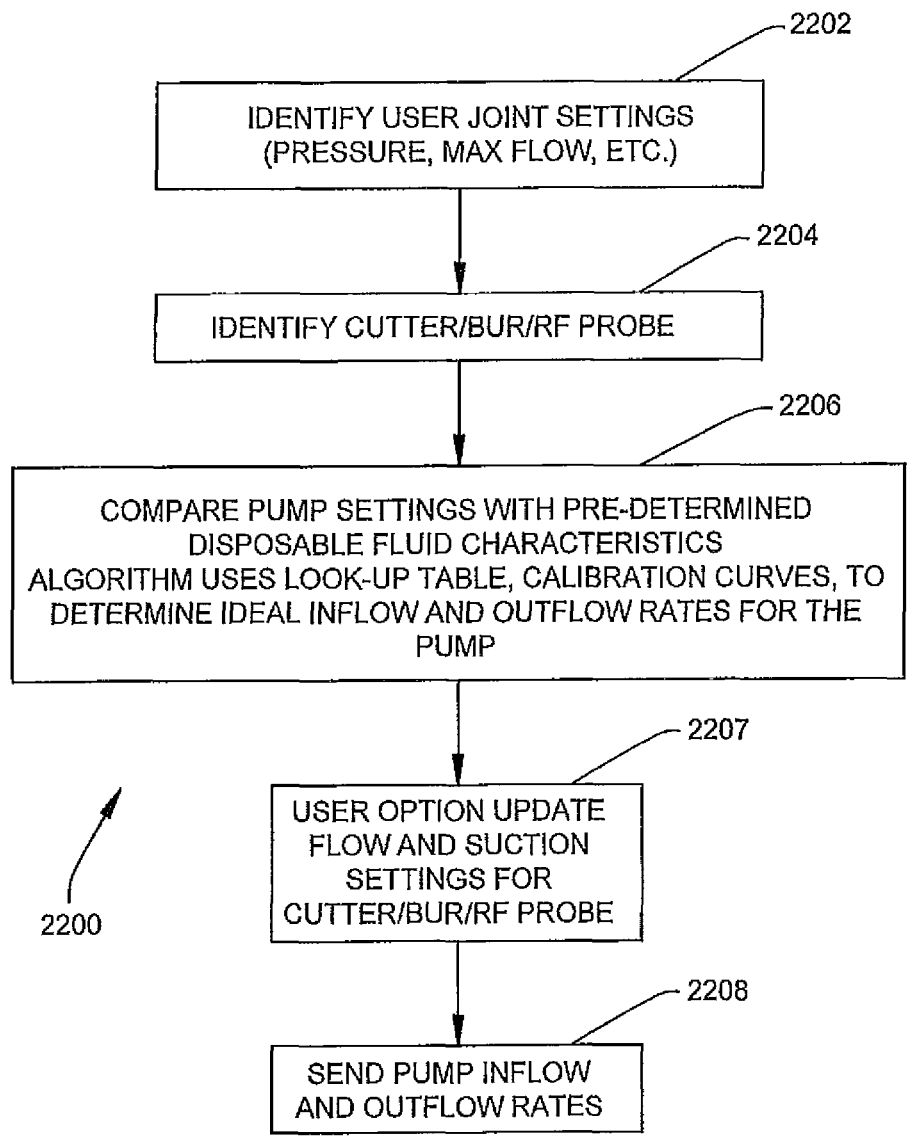
FIG. 31 is a flowchart of a portion of a pump system operating routine that includes obtaining information regarding a cutting accessory.

FIG. 31 is a flowchart of the steps of a portion of a pump flow control routine 2200 executed by the pump control processor 1042 that emphasizes the identification of a cutting accessory. At step 2202, the type of joint, maximum and minimum flow rates, a desired or best flow rate that minimizes fluid consumption and maintains good visibility, a maximum pressure value, a desired pressure value and other types of information, including but not limited to the information or parameters listed and shown in FIG. 26, can be provided to the pump control processor 1042. The information can be manually entered into the pump control processor 1042 via input device 1052, read or downloaded automatically from a memory card or the like, or provided by other means. Then the routine advances to step 2204.

At step 2204 surgical device information, including identification information for a cutting accessory attached thereto, is provided to the pump control processor 1042. As discussed above, the information can be provided over a communication bus. The surgical device 1032 can include an RF reader to identify an RF tag secured to the cutting accessory. In another embodiment, the pump includes an RF reader to identify RF tags secured to both the surgical device and the cutting accessory. The routine then advances to step 2206.

At step 2206, the routine or program executed by the pump control processor 1042 compares pump settings with predetermined disposable fluid flow characteristics. An algorithm or program uses a look-up table, calibration curves, and in some embodiments additional information to determine ideal fluid inflow and fluid outflow rates for operation of the pump 1014.

At step 2207, a user has the option to update or change the flow and suction settings for any cutter or bur provided with a handpiece or an RF electrosurgical probe device. Thus, in an instance wherein a user does not like default settings, new settings can be provided and stored.

At step 2208, the pump inflow control signals, and in some instances outflow information, is provided to the inflow pump motor and to additional devices to obtain ideal in-joint pressures and fluid flow at the surgical site.

A feedback path (not shown) from step 2208 returns to a program or routine whereat an algorithm recalculates pump flow rates based on one or more of real-time joint pressure, inflow head pressure, pump motor speeds, surgical device speed and ON/OFF condition. Typically, the routine does not need to re-identify the surgical device or the cutting accessory. Further, the user joint settings, such as desired joint pressure, maximum and minimum joint pressure, maximum and minimum fluid flow through the joint and desired fluid flow information typically do not change, and thus the routine typically does not return to step 2202 until one cutting operation ends and another cutting operation begins.

In one example, for a shaver operating at a motor speed of 12,000 RPM with a 5.0 mm round bur attached thereto, and a desired pressure value of 70 mmHg, the algorithm or routine executed by the pump control processor 1042 provides outputs to the inflow pump motor, the outflow pump motor, and in some instances to other devices including outflow pinch valves, to obtain the desired joint pressure of 70 mmHg, while maintaining desirable inflow and outflow rates for the pump output.

When the shaver 1036 is operated, the pump control processor 1042 receives the ON/OFF condition and the RPM output value of the shaver and calculates and controls the inflow pump RPM value that is output by the inflow pump motor, controls the outflow pump motor, and controls pinch valves provided with or near the outflow cassette 1026 by opening a valve for the outflow tubing 1034 connected to the shaver while closing a separate outflow tubing 1028 from the outflow cannula 1030.

The additional surgical device information, along with the joint pressure values calculated or sensed as described above, enable the pump control processor 1042 of the pump 1014 to more accurately control the $P_{joint}$ value and fluid flow rates that result in surgical site conditions that closely correspond to the selections or inputs of an authorized medical user operating the pump system 1010.

As the shaver is identified, a non-linear outflow rate to RPM curve is provided with a look-up table containing coefficients to predict the outflow rate based on the outflow RPM for controlling the pump to provide a desired or best outflow rate.

User preferences and other information from the pump control processor 1042 can be provided to the surgical device 1032, such as the shaver 1036 and RF electrosurgical device 1038. The preferences can include surgical device settings preferred by the medical user that will be operating the surgical device 1032 and the pump system 1010.

Unrecognized Cutting and RF Electrosurgical Devices:

The pump 1014 can be utilized with unrecognized third-party surgical devices 1032 that are not identifiable by the pump control processor 1042. Such RF electrosurgical devices and shaver devices are typically connected to power outlets located on the backside of the pump housing. Located within the pump housing are current and/or voltage sensing devices that sense a current waveform of the power drawn by the unrecognized surgical devices when operated. Instantaneous and past changes in the current waveform can be normalized to changes in the applied mains voltage and the pump control processor 1042 can execute a linear-discrimination algorithm to optimally differentiate between times when the unidentified surgical devices are off and when the surgical devices are activated to treat or cut tissue. The pump control processor 1042 utilizes the information to control the pump inflow motor, the pump outflow motor and in some instances pinch valves of the outflow tubing located at the outflow cassette 1026 and/or other devices to influence pump fluid inflow and fluid suction performance.

As discussed above, the critical flow rate values and maximum pressure value for the surgical site 1012 at the joint are typically different during operation of a surgical device 1032 as compared to during non-operation of the surgical device. Therefore, sensing surgical device activation enables adjustments to the desired joint pressure value and fluid flow by control of the inflow pump motor, outflow pump motor and other devices while the surgical device is activated.

In-Joint Sensor:

In some embodiments, an in-joint sensing device 1058 shown in FIG. 25B includes an in-joint pressure sensor and/or an in-joint temperature sensor that are disposed at or adjacent the surgical site. The in-joint sensing device 1058 can obtain and send a real-time pressure value from the surgical site 1012 to the pump control processor 1042, thereby avoiding reliance on the calculated $P_{loss}$ curves discussed above. The in-joint sensing device 1058 also reduces time delay in determining pressure changes in the joint. For instance, when pressure changes are measured upstream, there is a delay in the pressure change at the joint propagating through the inflow tubing to the sensor in the pump 1014. The in-joint pressure sensor also removes the upstream pressure measuring influence of hydrostatic head which occurs due to height differences between the pump and the cutting accessory located at the surgical site. Therefore, the pump need not be maintained at the same level or height as the surgical site. Details of in-joint sensing devices 1058 are disclosed in U.S. provisional patent Application Ser. No. 61/620,814 filed Apr. 5, 2012, the disclosure of which is hereby incorporated by reference.

In some embodiments, the temperature sensor of the in-joint sensing device measures real-time fluid temperature at the surgical site in the joint mainly during application of RF energy to ablate tissue therein. In this instance, when the measured joint temperature increases beyond a predetermined temperature value, the pump control processor 1042 operates to increase the fluid flow rate through the joint. For instance, the flow through a RF waste removal tube provided within the RF electrosurgical device can be increased by opening a pinch-valve for a dedicated outflow tube. This feature allows the pump control processor 1042 to maintain the joint temperature within acceptable limits and thus reduces the risk of unwanted cell damage due to an increased fluid temperature. The pump control processor 1042 can also quickly obtain the maximum fluid flow rate for the RF electrosurgical device and set the outflow to the maximum fluid flow rate to increase the flow rate through the electrosurgical device and the joint thus decreasing the joint temperature and reducing the risk of cell damage. In some embodiments, the pump control processor 1042 communicates the temperature value to the RF electrosurgical device 1036 for display to a medical user operating the RF electrosurgical device. In some embodiments, in-joint temperature and in-joint pressure values are both displayed.

Overpressure:

Regardless of the type of $P_{joint}$ calculation or direct pressure measurement, a $P_{joint}$ value must not exceed a predetermined pressure value. Thus, when an overpressure condition is calculated or measured, the pump control processor 1042 performs at least one of operating outflow pinch valves, reducing the RPM value of the inflow pump motor, and other steps to reduce the joint pressure.

Handpiece Suction Lever/Control Embodiments:

In some embodiments, a powered surgical hand piece having suction control is provided with a position sensor that determines the position of a suction control lever. One example of a powered handpiece that can be modified to include a lever position sensor is described in U.S. Pat. No. 7,682,333, the entire contents of which are hereby incorporated herein by reference. In some embodiments, a position of the suction control lever is measured by a position resister, and other position measuring arrangements are contemplated.

Figure 32:
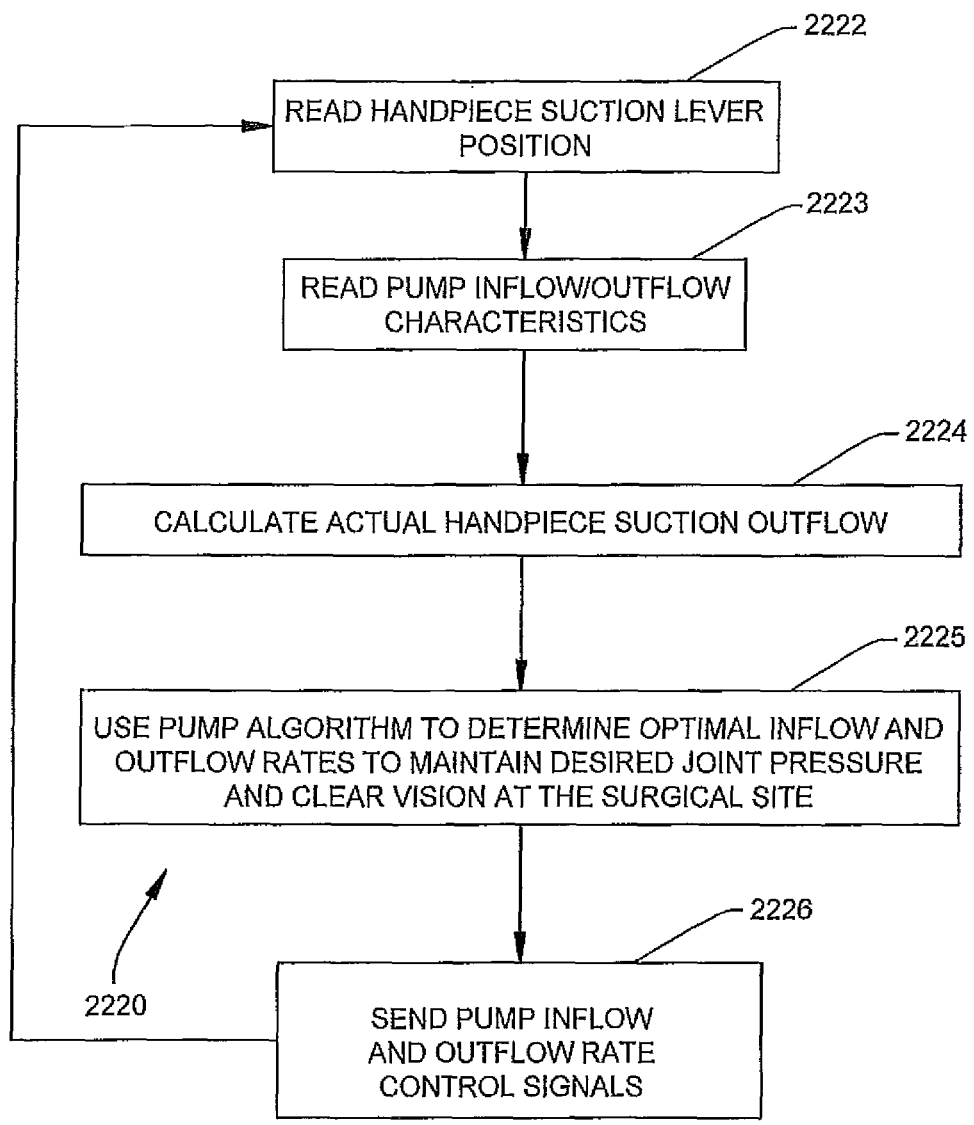
FIG. 32 is a flowchart of a pump system operating routine that includes sensing a suction lever position of a surgical device.

FIG. 32 shows a flowchart or routine 2220 wherein a position of a suction lever for controlling suction through a shaver handpiece or other handpiece is measured at step 2222. The lever position is provided to the pump control processor 1042. At step 2223, pump inflow/outflow characteristics are also provided to the pump control processor 1042. At step 2224, the processor 1042 calculates actual handpiece suction flow through the opening in a path or suction channel within the handpiece that is controlled by a valve corresponding to the suction lever position. At step 2225, the pump control processor 1042 executes a pump lever algorithm to determine an optimal inflow rate and to minimize the outflow while maintaining a desired pressure level for the surgical site 1012 of the joint in view of the suction lever position. Further, the pump algorithm controls flow conditions to provide clear vision for an endoscopic camera disposed at the surgical site. Pump inflow and outflow rates are output at step 2226 to control one or more of the inflow pump motor, the outflow pump motor, and other devices including pinch-valves as necessary to maintain a desired joint pressure. From step 2226, the pump control processor program or routine 2220 returns to step 2222 to measure the suction lever position and then advances to step 2223 to read the pump inflow/outflow characteristics. Then at step 2224, the pump control processor 1042 again determines new pump inflow and outflow rates in view of the suction lever position and the inflow/outflow characteristics. The routine 2220 repeats the steps at least while the handpiece is activated.

By measuring the suction lever position and executing the pump lever algorithm, the pump reacts quickly to the effect on joint pressure of rapid changes in the suction lever position.

Figure 33:
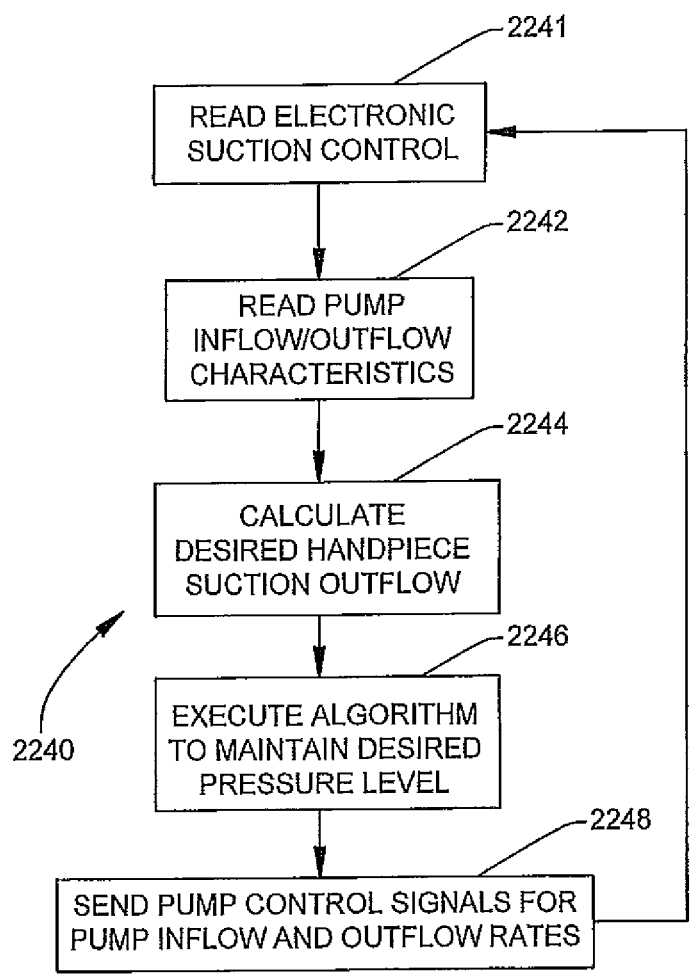
FIG. 33 is a flowchart of a pump system operating routine that calculates a desired handpiece suction outflow.

FIG. 33 shows a flowchart or routine 2240 for a second embodiment similar in purpose to the embodiment of FIG. 32, wherein the handpiece suction outflow is calculated based on an electronic suction control value obtained at step 2241 and pump inflow/outflow characteristics obtained at step 2242.

In this embodiment, a purely electronic (virtual lever) suction control provides no physical constraint, such as a valve disposed in a path within a handpiece, for metering of the fluid flow through a pathway in a surgical device 1032, such as a shaver or RF electrosurgical device including a suction channel. Thus, the suction channel through the handpiece is free from a valve or other adjustable fluid flow blocking device. The electronic suction control provides information to the pump control processor 1042 choosing the desired amount of fluid outflow.

At step 2244, the pump control processor 1042 calculates a desired handpiece suction outflow value. At step 2246, the pump control processor executes an algorithm to determine pump control signals that maintain a desired joint pressure level for the surgical site at the joint while providing the desired fluid flow rate through the surgical device 1032. The routine advances to step 2248.

At step 2248, the pump control processor 1042 provides control signals to one or more of pinch-valves, an inflow pump motor and an outflow pump motor to obtain the proper inflow and outflow rates, and to thus maintain a desired joint pressure level. The routine 2240 then returns to steps 2241, 2242, 2244 and 2246 in sequence and repeats the calculations, at least while the surgical device 1032 is in use.

In some embodiments, the electronic suction control is a physical lever mounted on the handpiece that is not connected to a valve therein, but instead changes a resistance value depending upon the lever position. In other embodiments, the electronic suction control can be a touch type sensor on the handpiece with an increase touch pad and a decrease touch pad for increasing or decreasing the suction flow through the handpiece. In some embodiments, the electronic suction control can be provided on multiple devices besides the handpiece. For example, the electronic suction control can be provided on a footswitch connected to the surgical device and as indicia on the input device 52, such as a touchscreen of the pump 14, 1014.

One problem addressed by the suction control embodiments of FIGS. 32 and 33 is related to a situation that can occur wherein a surgical device 1032, such as a shaver, is powered on, and the pump head pressure is then increased as the cutting bur of a shaver is spinning, even though there is no suction occurring. Such an event could result in extravasation due to overpressure at the surgical site. In the embodiments of FIGS. 32 and 33, the algorithm does not increase head pressure even when the cutting bur is activated, unless a pressure drop is sensed.

Figure 34:
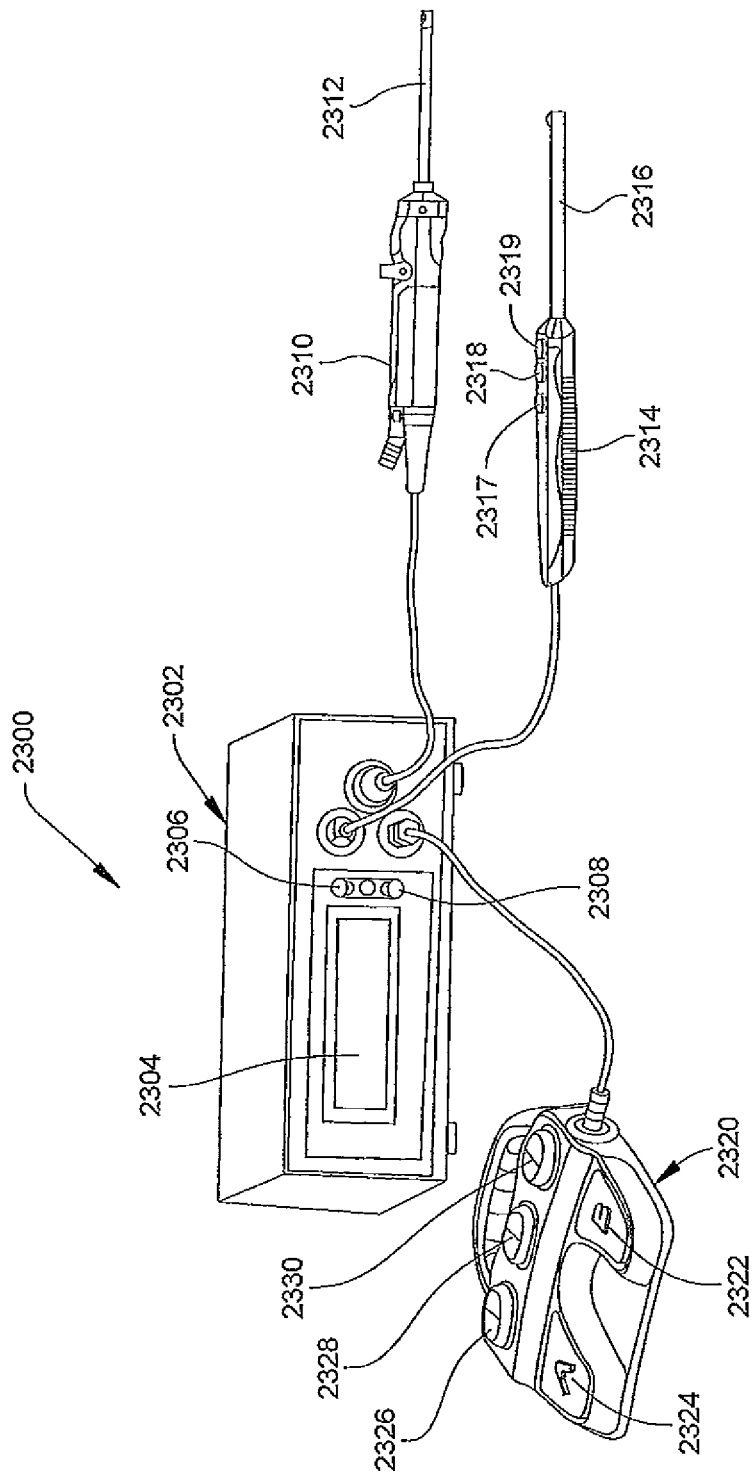
FIG. 34 is a perspective view of a surgical device including components thereof.
Figure 35:
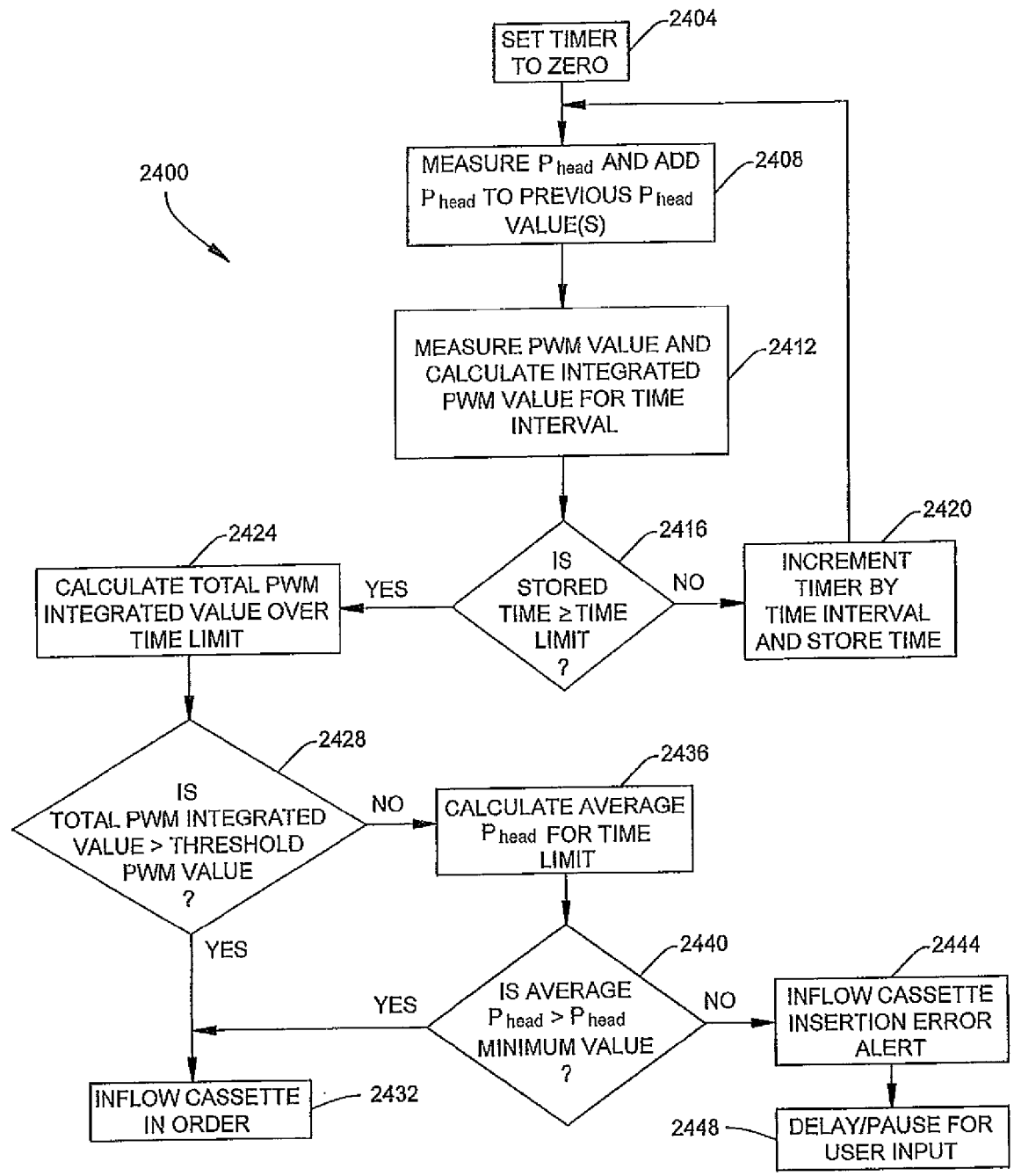
FIG. 35 is a flowchart of a pump system operating routine that determines whether an inflow cassette is properly inserted in an inflow drive mechanism of a pump housing.

Surgical Device Actuator Mapping:

FIG. 34 shows a surgical device 2300 with surgical handpieces and a footswitch. More specifically, FIG. 34 shows a surgical device console 2302 that includes a touchscreen 2304, a surgical device processor and control buttons 2306, 2308. Further, the surgical device 2300 includes a pair of handpieces, more specifically, a shaver handpiece 2310 having a cutting accessory 2312 attached thereto and an RF electrosurgical probe handpiece 2314 for cutting and coagulation of tissue. Further, the surgical device 2300 includes a footswitch 2320 having a plurality of pedals 2322, 2324 and push buttons 2326, 2328, 2330. In some embodiments, the cutting handpiece 2310 and cutting accessory 2312 are a motor powered mechanical shaver having a bur or other cutting device secured thereto. Actuators, such as push buttons or other switches, are disposed on the handpiece 2310 to provide input signals to the surgical device processor.

The RF electrosurgical probe handpiece 2314 includes a wand 2316 at the distal end thereof for heating tissue for cutting or coagulation purposes. The electrosurgical probe handpiece 2314 can include a plurality of actuators 2317, 2318, 2319 for providing inputs to the surgical device processor that, for example, control power to the handpiece.

In operation, the footswitch 2320 can provide control signals to the surgical device processor which controls power to the various handpieces 2310, 2314 depending on the state of the surgical device processor, by selection of the pedals 2322, 2324 or buttons 2326, 2328, 2330.

The surgical device processor is connected by the FIREWIRE™ Backbone bus to the pump control processor 1042 of the pump system 1014. The bus enables bi-directional communication between the pump control processor 1042 and the surgical device processor. In some embodiments, user preference files stored in the pump memory are provided to the surgical device processor with information as to the various modes of operation for the pump system. In some embodiments, regardless of whether or not the surgical handpiece is performing an operation on tissue, a WASH mode, a CLEAR mode and a HOTSWAP mode are available for the pump system 10, 1010 as discussed below.

More specifically, in some embodiments a WASH mode or function of the pump system 1010 is provided. In the WASH mode, in response to a manual wash input signal, a temporary joint pressure increase occurs, along with a temporary flow increase for a predetermined time period. The WASH mode flushes out debris and blood and the temporary joint pressure increase from flushing assists in stopping bleeders, if bleeders are present. Thereafter, the pump 1014 returns to outputting of the predetermined desired joint pressure.

In some embodiments, the pump system 1010 includes a CLEAR mode or function. In response to a manual clear input signal, fluid flow increase for a predetermined time in the inflow mode. Suction (outflow) increases for a predetermined time when the pump system is in inflow/outflow mode. Finally, in some embodiments, the pump system 1010 includes a HOT SWAP mode or function, wherein in response to a hot swap input signal, cannulas can be switched out or replaced during live use of the pump system, while minimizing fluid pressure and fluid flow issues.

In some embodiments, information regarding each of the above listed modes is provided to the surgical device processor from the pump control processor. A user at the touchscreen 2304 of the surgical device 2300 maps various switch type actuators on the surgical handpieces 2310, 2314 and/or foot pedals 2322, 2324 along with buttons 2326, 2328, 2330 on the footswitch 2320 to selectively actuate one of the WASH, CLEAR and HOT SWAP modes. Further, selection of joint pressure or an inflow rate can be controlled by mapped actuators of the surgical device. The surgical device processor can map one actuator to any one of the modes.

In some embodiments, plural control actuators are individually mapped to various ones of the pump system modes. An actuator on a handpiece 2310, 2314 and on the footswitch 2320 can be mapped to select the same operating mode and to enable fluid flow through the outflow path of the surgical handpiece 2320, 2314 when the handpiece is not treating tissue.

In some embodiments, actuator mapping is performed by selections made at either or both of the surgical device touchscreen 2304 and the input device of the pump 1014. In some embodiments, the desired mapping of actuators is loaded through preference files.

In a VACUUM mode, when the surgical device handpiece 2310, 2314 not treating tissue, a mapped actuator controls fluid outflow through a handpiece suction outflow path of the surgical device handpiece. Thus, during an inflow/outflow pump operation, when the surgical device handpiece is not performing a tissue treatment, the corresponding mapped actuator provides suction through the handpiece suction outflow path by opening a suction pinch valve to enable flow between the handpiece and the outflow pump, while closing a dedicated pinch valve that enables flow from an outflow cannula to the outflow pump. Further, in response to the mapped actuator, the outflow motor operates to provide the desired suction value through the handpiece suction outflow path. Thus, the pump system is controlled to provide suction through the handpiece suction outflow path of the surgical handpiece when the surgical device is not actuated to treat tissue. Finally, providing the actuator on the surgical device handpiece or the surgical device footswitch 2320 provides ease of use for an operator.

In some embodiments, the desired outflow rate is provided from a user preference file that is loaded into the surgical device processor or the desired outflow rate is a default suction outflow rate.

While the embodiments in FIGS. 1A and 25A show the shaver and RF electrosurgical device as entirely separate devices, as illustrated in FIG. 34 the devices may share a common console 2302.

Operation:

At pump system start-up, pressure at the surgical site 1012 in the joint is measured in any of the ways described herein and the pump control processor 1042 initially operates to maintain the pressure $P_{joint}$ at a preselected desired constant pressure. The pressure is typically maintained until a critical flow rate is reached, at which point the pump control processor 1042 changes or shifts to a constant flow mode and allows the pressure in the joint to decrease in order to maintain a flow rate. The flow rate can be set to a predetermined low flow rate that is sufficient to, for example, maintain good visualization for a camera of an endoscope while reducing fluid consumption.

The inflow only mode is similar to the inflow/outflow mode with the exception that there is no control of the outflow. Again, the pump control processor 1042 operates the inflow pump motor to maintain a set pressure value at the joint until a predetermined critical inflow rate is reached, at which point the inflow pump motor maintains a constant minimum flow rate, instead of a constant pressure.

As discussed above, in some embodiments the activation of a surgical device 1032 increases the critical flow rate value and/or predetermined desired joint pressure value so that the pump control processor 1042 maintains a desired joint pressure over a larger range of flow rate values. Further, once the new selected stored inflow value is read by the pump control processor 1042, the inflow pump motor maintains a different constant inflow of fluid to the surgical site at the joint while the surgical device is activated.

As discussed above, in an inflow/outflow mode that includes sensing of cutting device operation, fluid outflow from the cutting device, such as a shaver, is also measured to assist in a timely response to a decrease in joint pressure when the cutting device is actuated.

The multi-device operating room controller 1043 illustrated in FIG. 25B is capable of controlling the pump 1014 in a similar manner as the foot pedal 1044 and the remote control 1046, as well as the input device 1052. The multi-device controller 1043 receives pump operating status and information from the pump 1014 for display thereon and can provide pump control signals to the pump 1014 over the Stryker® FIREWIRE™ Backbone bus arrangement. Thus, a separate controller in a medical room is capable of controlling operation of the pump system 1010 and a plurality of other devices that may include the shaver 1036 and the RF electrosurgical device 1038.

While a single pump control processor 1042 is illustrated in drawing FIG. 25B, the use of at least a plurality of, and in one embodiment eight, processors for different functions and purposes is contemplated for the pump control system.

The pump system operations discussed herein are utilized for various embodiments including an inflow only pressure and inflow rate control, embodiments additionally including outflow pressure and outflow control, embodiments provided with direct in-joint pressure and temperature sensing, embodiments utilizing specific recognized or unrecognized surgical devices, embodiments including specific pump cassettes, and other arrangements.

In most embodiments, the height of the inflow cannula 1024 located at the joint is typically intended to be at the same height as the inflow pump motor 406 of the pump 1014.

Inflow Pump Cassette Insertion Detection:

Another embodiment of an inflow pump control arrangement is utilized to confirm that the inflow pump cassette is entirely inserted or properly locked into place with the inflow drive mechanism and the pump housing. Detection occurs during a pump priming sequence for the surgical pump system and an insertion error alert is provided by the pump control processor 1042 in the event proper insertion is not detected. For a typical inflow pump cassette and inflow drive mechanism, the inflow pump motor generally is a brushless DC motor that receives pulse width modulation (PWM) drive signals. In another embodiment, the inflow pump motor is a stepper that receives PWM signals that drive the motor essentially predetermined distances in order to control the output of fluid through tubing and an inflow cannula to a surgical site.

In another embodiment, PWM current is not applied to drive the pump motor. Instead, different currents, such as a constant current or a sinusoidal current, are provided to the pump motor. Thus, the pump motor current device measures a different type of current to obtain a pump operating value for processing as discussed below. In other embodiments, the pump motor measuring device is a voltage measuring device or a power measuring device, and the inflow cassette insertion check routine 2400 discussed below, processes the measured pump operating voltage value or power value. Therefore, while the check routine as discussed below is directed specifically to measured PWM values, the same routine operates with various types of current values, along with voltage and power values, provided as the measured pump operating value.

In some embodiments, after the inflow pump cassette is inserted into the pump housing an RFID tag or structure mounted on the inflow pump cassette is detected to determine the presence of the pump cassette. Such presence, however, does not ensure that the inflow pump cassette is entirely and properly mounted to the inflow drive mechanism and pump housing. In some embodiments, upon detection of the RFID structure, the pump control processor 1042, automatically begins the inflow cassette insertion check routine 2400 when pump priming begins.

The inflow cassette insertion check routine 2400 begins at step 2404 and sets the timer of the pump control processor to a zero value. Upon the routine 2400 advancing to step 2408, an inflow pump pressure sensor measures inflow pump pressure $P_{head}$ and adds the measured $P_{head}$ value to any previously measured and stored $P_{head}$ values, whereat the routine advances to step 2412.

At step 2412, an inflow pump motor PWM measuring device measures a pulse width modulation (PWM) value for the inflow pump motor. The pump control processor 1042 receives the PWM value and calculates an integrated PWM value for a time interval. Thus, in some embodiments, the pump motor PWM measuring device is a pump motor PWM current measuring device that measures the current provided to drive the inflow pump motor.

The cassette insertion check routine 2400 then advances to decision step 2416. So long as a stored time, which was initially set to zero at step 2404, is not greater than a predetermined priming time limit, the pump control processor advances the routine 2400 to step 2420 whereat the time is incremented by the amount of a time interval, and the incremented time is stored by the pump control processor.

The predetermined priming time limit, the time interval, a threshold PWM value, and a $P_{head}$ minimum value are determined by the pump control processor 1042 in view of the hardware of the surgical pump system, and typically by the identified inflow cannula and the identified endoscope utilized therewith. Other factors may include the tubing size and tube length, along with user preferences.

Returning to the inflow cassette insertion check routine 2400, from step 2420 the routine returns to step 2408 whereat $P_{head}$ is measured and added to previous $P_{head}$ values. The cassette insertion check routine 2400 advances again to step 2412 whereat a measured PWM value is obtained by the inflow pump motor PWM measuring device, and the pump control processor calculates and stores an integrated PWM value for a time interval.

The routine 2400 again advances to step 2416, whereat if the pump control processor determines that the stored time is not greater than or equal to the predetermined priming time limit, then steps 2420, 2408, 2412 are repeated. Each time these steps are taken, the same time interval occurs between measurements. After a number of time intervals wherein $P_{head}$ and a PWM value are measured, the priming time limit is obtained and decision step 2416 advances the routine 2400 to step 2424.

At step 2424, the pump control processor calculates a total PWM integrated value over the priming time limit for the inflow pump motor from the integrated PWM values for each of the time intervals. Thereafter, the check routine 2400 advances to step 2428 whereat the total PWM integrated value is compared with the threshold PWM value determined by the pump control processor in view of the hardware attached to the pump arrangement. In the instance that the total PWM integrated value is greater than the threshold PWM value, the routine 2400 advances to step 2432, whereat the inflow cassette is in order and the pump system is available for use.

In the event that the total PWM integrated value over the time limit at decision step 2428 is less than the threshold PWM value, the routine 2400 advances to step 2436. At step 2436, the pump control processor 1042 calculates an average $P_{head}$ value over the predetermined priming time limit and the routine 2400 advances to step 2440.

At step 2440, the average $P_{head}$ value is compared to a $P_{head}$ minimum value that was calculated previously by the pump control processor based on the hardware. When the average $P_{head}$ value is greater than the $P_{head}$ minimum value, the routine 2400 advances to step 2432 indicating that the inflow pump cassette is properly inserted and the pump control processor advances to another routine or operating stage as the pump system is ready for operation.

In the event that the average $P_{head}$ value at step 2440 is not greater than the $P_{head}$ minimum value, the routine 2400 advances to step 2444.

At step 2444, the pump control processor 1042 outputs an inflow cassette insertion error alert, such as a sound output by a speaker and/or a visual indicator on a pump touch-screen, to alert a user to the improper positioning of the inflow pump cassette. After step 2444, the cassette insertion check routine 2400 advances to step 2448 whereat there is a system delay or pause to wait for a user input to address the situation. Further, the inflow pump motor typically is idled.

In the embodiment wherein the pump motor PWM measuring device is a pump motor PWM current measuring device, the PWM current measuring device measures a PWM current value. The pump control processor calculates an integrated PWM current value for the PWM current value at each interval. After the time intervals are complete, the pump control processor calculates a total PWM integrated current value from the integrated PWM current values that is compared with a threshold PWM current value to determine whether the cassette is locked in completely. In an instance wherein the inflow pump cassette is not locked in, there typically is a current drop in the PWM current value measured for the time intervals. Thus, the calculated total PWM integrated current value is less than a threshold PWM current value due to the current drop and a second test is done utilizing the measured $P_{head}$ values.

For the second test, the average $P_{head}$ value calculated over the entire priming time limit is determined and compared against the $P_{head}$ minimum value. When the inflow pump cassette is not locked in place properly, the pressure sensing membrane 212 of the pump cassette typically is off axis with respect to the pressure sensor 492 mounted on the pump. If not in alignment, the measured pressure $P_{head}$ is less than an expected pressure. Thus, the location of the pressure sensing membrane 212 of the inflow pump cassette is critical to proper inflow pressure measurement and a reduced average $P_{head}$ value indicates improper placement of the inflow pump cassette. Therefore, this second test ensures that an alert is not provided by the pump control processor unless there clearly is an issue with insertion of the inflow pump cassette into the pump housing.

Moreover, performing the cassette insertion check routine 2400 at inflow pump priming, ensures proper inflow cassette position before usage of the pump system occurs.

Unidentified Hardware Properties:

Another embodiment of an inflow pump control arrangement is utilized wherein the flow resistance properties of the tubeset hardware, comprising the inflow cannula 1024 and the endoscope 1025 are unknown. Thus, while the manufacturer and type of endoscope, along with the manufacturer and type of cannula are known, the $P_{loss}$ curve, load coefficients and flow characteristics thereof are not known. In this embodiment, the pump control processor 1042 utilizes a hardware calibration or hardware $P_{loss}$ curve determination routine 2500 that includes an algorithm as shown in FIG. 36 to obtain pump RPM values and $P_{head}$ values that are used to calculate the pressure loss coefficients $COEF_1$ and $COEF_2$ that define the $P_{loss}$ curve.

Figure 36:
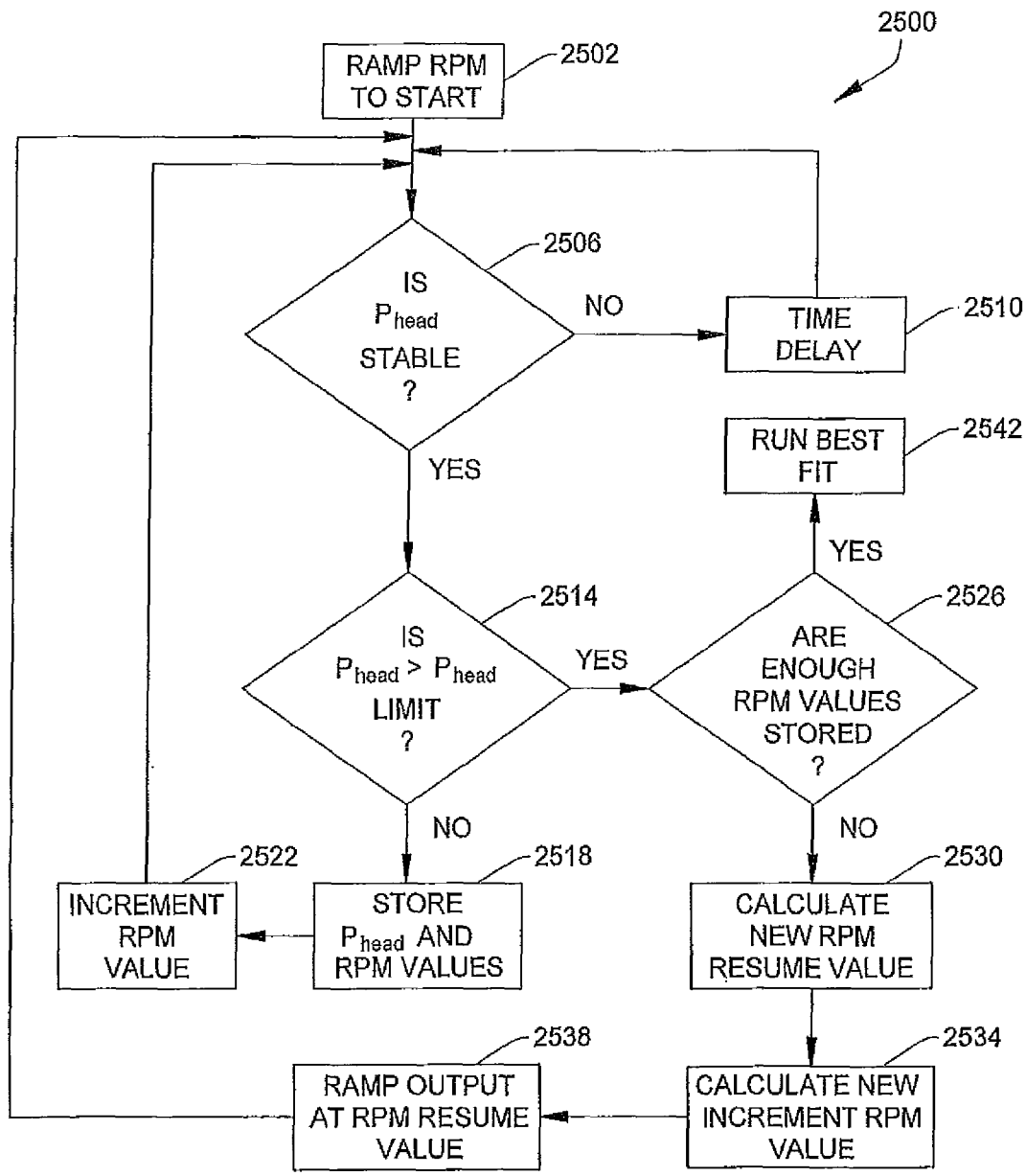
FIG. 36 is a flowchart of a hardware calibration routine to determine unknown hardware flow properties.

The hardware calibration routine 2500 shown in FIG. 36 begins at step 2502. At step 2502, the inflow pump motor provided with the inflow cassette 1020 operates and ramps up to a particular start point RPM value. The hardware calibration routine 2500 advances to decision step 2506 and determines if $P_{head}$ is stabilized. If $P_{head}$ is not stable, the routine 2500 advances to step 2510, wherein a predetermined time delay is provided. After the predetermined time delay, the routine 2500 returns to step 2506 and again determines if $P_{head}$ is stabilized. If not, the routine 2500 again advances to step 2510 and repeats steps 2506, 2510 as necessary. When $P_{head}$ is stabilized at step 2506, the hardware calibration routine 2500 advances to decision step 2514 whereat measured $P_{head}$ is compared to a predetermined $P_{head}$ limit value. If measured $P_{head}$ is less than or equal to the $P_{head}$ limit value, the routine 2500 advances to decision step 2518. At step 2518, the measured $P_{head}$ value and the measured RPM value are stored and the routine 2500 advances to step 2519. At step 2519, the pump control processor determines if enough RPM values are stored. In some embodiments, more than six stored RPM values are required. If not enough RPM values were previously stored, the routine 2500 advances to step 2522.

If enough RPM values were stored, the routine 2500 advances to step 2524. At step 2524, load coefficients $COEF_1$, $COEF_2$ for a best fit algorithm having a second order polynomial are calculated from the plurality of stored $P_{head}$ values and the plurality of stored pump motor RPM values obtained by the routine 2500. At step 2524, the coefficients $COEF_1$, $COEF_2$ are stored in pump memory 1051 for the pump control processor 1042 and define the pressure loss $P_{loss}$ curve that provides a varying $P_{loss}$ value in response to varying RPM values of the inflow pump motor. The $P_{loss}$ curve is a measured curve based on the large number of $P_{head}$ and RPM values. The routine 2500 is complete.

If the hardware calibration routine 2500 advances to step 2522, the RPM value of the inflow pump motor is incremented to a new RPM value and output by the pump motor. The routine 2500 returns to decision step 2506 and if $P_{head}$ is stable, advances to step 2514. If $P_{head}$ is less than or equal to the $P_{head}$ limit value, measured $P_{head}$ and measured RPM values are again stored at step 2518 and the RPM value output by the pump motor subsequently is increased at step 2522. Steps 2506, 2514, 2518, 2519 (so long as number of RPM values is not exceeded) and 2522 continue in sequence, and thus the $P_{head}$ and the RPM values are repeatedly measured and stored until measured $P_{head}$ is greater than the $P_{head}$ limit value at step 2514. Then the hardware calibration routine advances from step 2514 to decision step 2526.

At step 2526, the hardware calibration routine 2500 determines whether enough RPM values have been stored by the pump control processor. If not enough RPM values were previously stored, the routine 2500 advances to step 2530. At step 2530, a new RPM resume value is calculated that typically is less than the RPM value when measured $P_{head}$ was greater than the $P_{head}$ limit value. In some embodiments, the RPM resume value is more than 50% less than the measured RPM value when the $P_{head}$ limit value was exceeded.

The hardware calibration routine 2500 advances to step 2534 whereat a new increment RPM value is determined. The amount of the new increment value typically is less than the increment value provided at startup of the routine 2500. The routine advances to step 2538 whereat the pump motor is driven at the RPM resume value. Thereafter, the routine 2500 advances to decision step 2506 to determine if $P_{head}$ is stable and repeats steps 2514, 2518, 2519, 2522, 2506, 2510 as discussed above, until $P_{head}$ is greater than the $P_{head}$ limit value at step 2514. If $P_{head}$ is greater, the hardware calibration routine advances to decision step 2526. If enough RPM values and corresponding $P_{head}$ values are stored, the routine advances to step 2542.

At step 2542, the hardware calibration routine 2500 operates in the same manner as set forth above with respect to step 2524.

As in earlier embodiments, RPM value of the inflow pump motor and the load coefficients are applied in the second order polynomial equation:

$$P_{loss} = COEF_1 \times (RPM\ value)^2 COEF_2 \times (RPM\ value).$$

The pressure loss equation thus results in a calculated pressure loss $P_{loss}$ for a pump system having the endoscope and the inflow cannula with previously unknown hardware properties disposed between the pump and the surgical site of a joint.

Additionally, $COEF_1$, $COEF_2$ and the $P_{loss}$ curve determine the previously unknown flow resistance of the hardware (endoscope, inflow cannula) being utilized. Further, the pump control processor 1042 calculates a maximum flow for the hardware.

The endoscope and the cannula typically are named, for example by manufacturer name and model number. The $P_{loss}$ curve, coefficients and other information are stored in the pump memory of the pump control processor for future use with an identifier name. Therefore, instead of performing the hardware calibration routine for a future use of the hardware, the identifying name for the hardware is input to the pump control processor and the previously measured $P_{103}$, curve and coefficients are obtained from a look-up table in the pump memory.

The hardware properties stored in the pump memory can also be sent to a customizer that is typically remote from the pump system. The customizer adds the identifying name and hardware properties to a data storage. The customizer selectively transfers the identifier name and hardware properties to different pump systems so that hardware calibration need not be repeated for the hardware at a different pump system. A customizer can be a remote PDA type device or other device that stores user preferences and other information.

Further, the hardware identifying name and properties are stored by the pump control processor that performed the hardware calibration routine as a preference file.

Unlike other embodiments, wherein the inflow coefficient $COEF_{INFL}$ is determined from the identified hardware, in one embodiment $COEF_{INFL}$ is determined from a look-up table in view of the values of coefficients $COEF_1$, $COEF_2$.

Unidentified Components:

Another embodiment of an inflow pump control arrangement is utilized wherein the dimensions and other properties of the inflow tubing 1022, inflow cannula 1024 and the endoscope 1025 are unknown. In this embodiment, the pump control processor 1042 utilizes a calibration routine or an algorithm as a start-up pump priming routine 3070 as shown by the flowchart in FIG. 37 to obtain data values that are used to calculate the pressure loss coefficients COEF1 and COEF2 that define a $P_{loss}$ curve.

Figure 37:
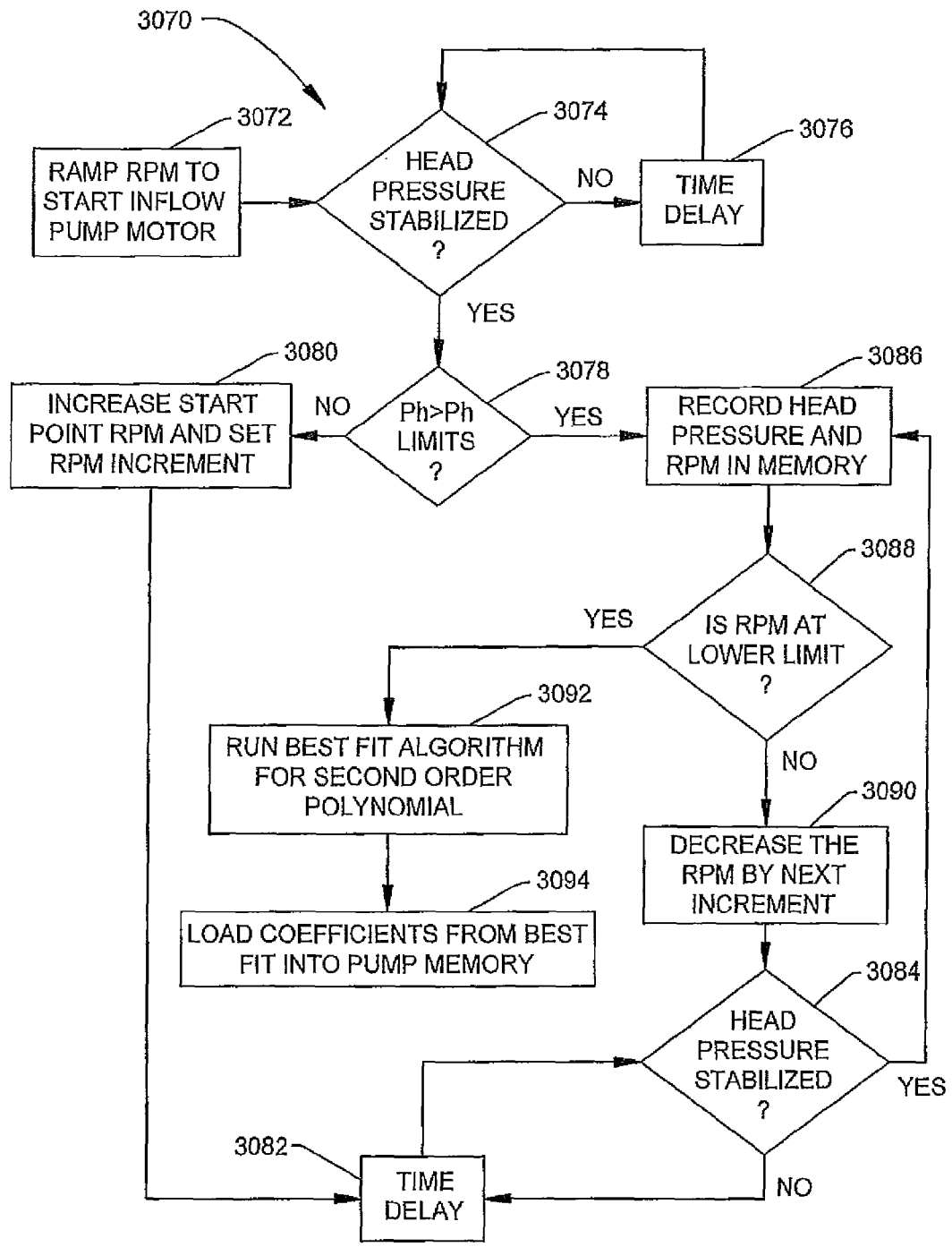
FIG. 37 is a flowchart for a pump system operating routine that determines unidentified hardware properties at pump priming.

At start-up, the pump priming routine 3070 shown in FIG. 37 begins. At step 3072, the inflow pump motor provided with the inflow cassette 1020 operates and ramps up to a particular start point RPM value. The pump control processor 1042 executes the pump priming routine 3070 at decision step 3074, to determine if $P_{head}$ is stabilized. If not stable, the priming routine 3070 advances to step 3076, wherein a predetermined time delay is provided. After the predetermined time delay, the routine 3070 returns to step 3074 and again determines if $P_{head}$ is stabilized. If not, the routine again advances to step 3076 and repeats steps 3074, 3076 as necessary. When $P_{head}$ is stabilized, the priming routine advances to decision step 3078 wherein measured $P_{head}$ is compared to a predetermined pressure head limit value. If measured $P_{head}$ is less than or equal to the pressure head limit value, the routine advances to decision step 3080. At step 3080, the RPM value of the inflow pump motor is increased to a starting point and an RPM increment value is set. The pump priming routine 3070 advances to step 3082 whereat a predetermined time delay is executed. Thereafter, the routine advances to decision step 3084. At step 3084, the routine determines if $P_{head}$ is stabilized. If not stable, the routine returns to time delay step 3082, which is repeated via decision step 3084 until a stabilized $P_{head}$ is achieved. When $P_{head}$ is stabilized, the routine advances from step 3084 to step 3086.

At step 3086, the pump control processor 1042 records the measured $P_{head}$ value and the corresponding measured RPM value of the inflow pump motor. After storing the values, the routine advances to decision step 3088 wherein the real-time RPM value of the inflow pump motor is compared with a predetermined lower limit RPM value. So long as the lower RPM limit value is not reached, the routine 3070 advances to step 3090. At step 3090, the RPM value of the pump motor is decreased by a predetermined increment. Thereafter, the routine advances to decision block 3084. As discussed above, decision step 3084 provides time delay via step 3082 until $P_{head}$ stabilizes. Once $P_{head}$ is stable, the routine again advances to step 3086 whereat the $P_{head}$ value and the inflow pump motor RPM value are stored in memory by the pump control processor 3042. Steps 3088, 3090, 3084, 3082 and 3086 are repeated until the measured RPM value of the inflow pump motor is at or below the lower limit RPM value as determined at decision step 3088. When the lower limit RPM value is reached, the pump priming routine 3070 advances to step 3092.

At step 3092, load coefficients COEF1, COEF2 for a best fit algorithm having a second order polynomial are calculated from the plurality of stored $P_{head}$ values and stored motor RPM values obtained by the routine 3070. At step 3094, the coefficients COEF1, COEF2 are stored in pump memory 1051 for the pump control processor 1042 and define the pressure loss $P_{loss}$ curve that provides a varying $P_{loss}$ value in response to varying RPM values of the inflow pump motor.

As in the previous embodiment, RPM value of the inflow pump motor and the load coefficients are applied in the equation:

$$P_{loss} = COEF1 \times (RPM\ value)2 + COEF2 \times (RPM\ value).$$

The pressure loss equation thus results in a calculated pressure loss $P_{loss}$ for a pump system having an unidentified tubing size and length, an unidentified endoscope and an unidentified cannula disposed between the pump and the surgical site of a joint.

Unlike other embodiments, in this embodiment pump priming execution is necessary to determine the coefficients COEF1, COEF2 for the second order polynomial equation defining a $P_{loss}$ curve.

Figure 38:
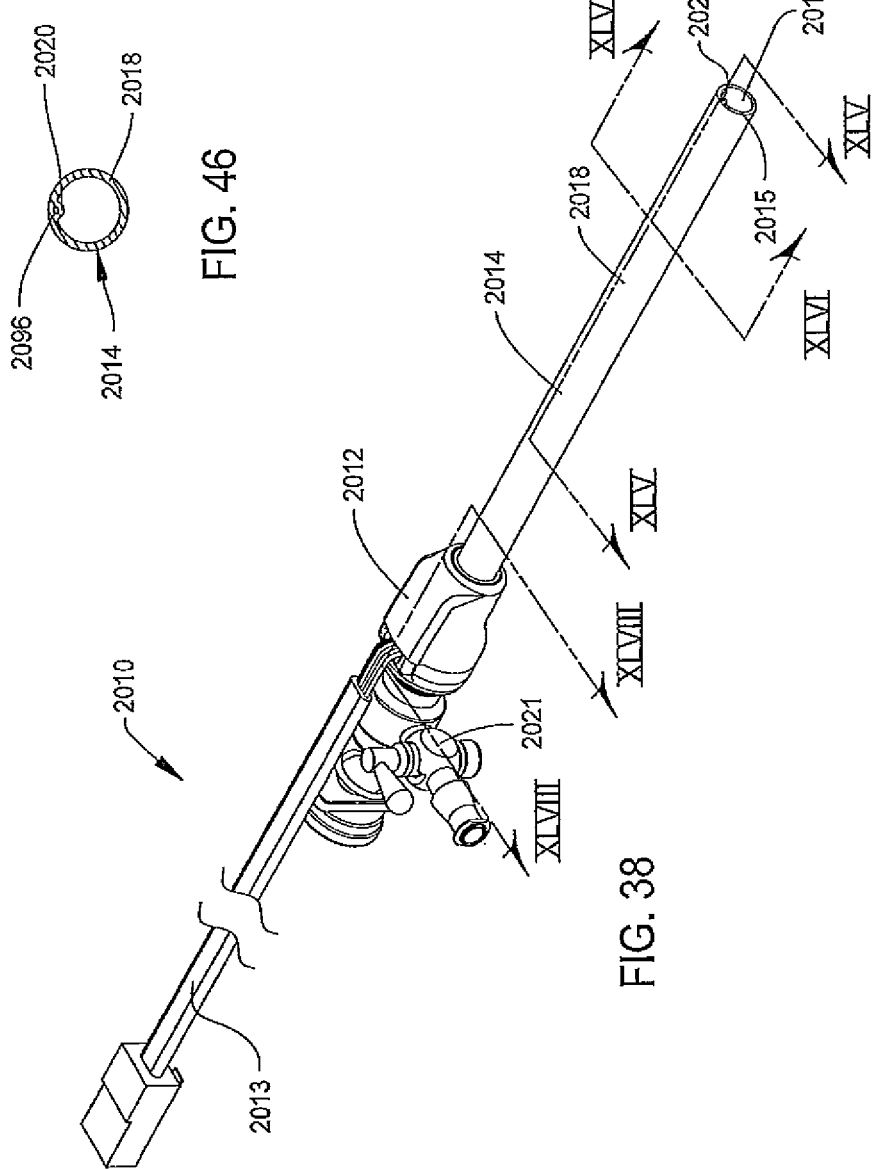
FIG. 38 is a perspective view of an in-joint sensor which may be part of or connected to the pump system.

As discussed above, and with reference to FIG. 38, the pump system 10 or 1010 may also include a miniaturized in-joint sensor 2010 which may include a pressure sensing device and/or a temperature sensing device. The in-joint sensor 2010 is preferably disposable and generally includes an integration component 2012, a cable 2013, a sheath 2014 (which can form the inflow cannula 24 or 1024 described above, a part thereof, or can be connected to or integral with the inflow cannula 24 or 1024), and in-flow tubing 2021 (which can be connected to or integral with the inflow tube 22 or 1022 described above). The sheath 2014 is preferably tubular in configuration and has a tubular wall 2015 with an inner wall surface 2016 that defines an inner lumen, and an outer wall surface 2018. The inner lumen extends substantially in the direction of the longitudinal axis of the sheath 2014. Attached to the inner wall surface 2016 is a shaft 2020, which is discussed in more detail below.

Figure 39:
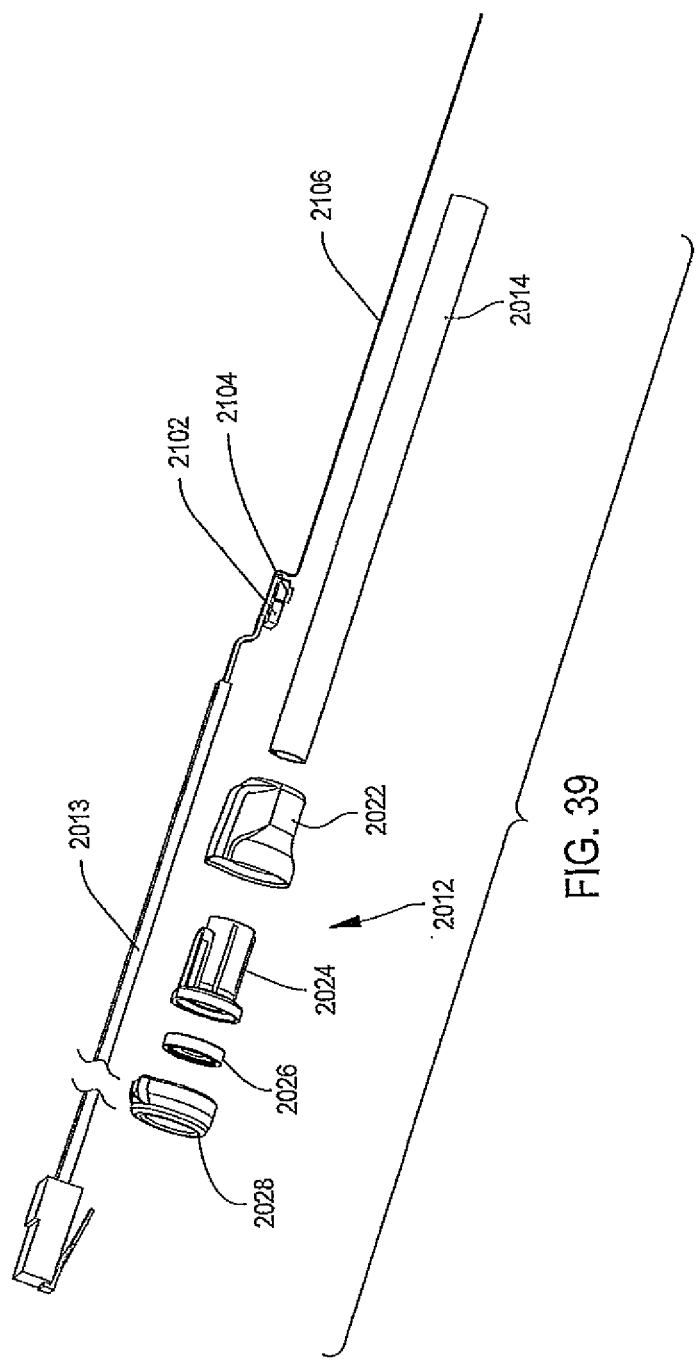
FIG. 39 is a perspective exploded view of a sheath, housing, and sensor/cable unit of the in-joint sensor of FIG. 31.

As shown in FIG. 39, the integration component 2012 includes a housing outer shell 2022 which defines a majority of the outer structure of the integration component 2012. The integration component 2012 also includes an inner member 2024 which resides within the outer shell 2022, an inner ring 2026, preferably of rubber, which fits within a portion of inner member 2024, and a proximal member 2028 which fixedly attaches to outer shell 2022.

The housing outer shell 2022 is shown in more detail in FIG. 40. The outer shell 2022 is preferably made of ABS, but may be made of any practical substantially rigid substance. The depicted outer shell 2022 includes a generally rounded portion 2030 which terminates at a top 2032 that has a slight radial curve. The top 2032 extends nearly the entire length of the outer shell 2022. The outer shell terminates distally in a circular aperture 2034 which is sized and shaped to receive and retain the sheath 2014, and is liquid tight to maintain a fluid seal. The rounded portion 2030 and top 2032 terminate proximally in an opening 2036. The outer shell 2022 defines an interior space 2038 which is sized and shaped to receive inner member 2024.

The inner member 2024 is shown in FIG. 41. The inner member 2024 includes a generally cylindrical portion 2040, which extends lengthwise over at least a majority of the inner member 2024. The cylindrical portion 2040 terminates proximally in a rounded end portion 2042 which has a flat top 2044 and has a larger diameter than cylindrical portion 2040. Together, the cylindrical portion 2040 and the rounded end portion 2042 define an interior space 2046 which is sized and shaped to receive a portion of the in-flow tubing 2021 and inner ring 2026, as discussed in more detail below. The inner member 2024 also includes a top tray 2048, which includes a tray inner space 2049 defined by an outer lip 2050. The top tray 2048 is sized and shaped to receive a portion of a sensor housing and/or cable 2013. Extending downwardly from the top tray 2048 is a pressure sensor aperture 2052. The aperture 2052 is defined by a circular edge 2054, which is preferably countersunk to allow secure attachment of the pressure sensor. Also in the interior surface of the top tray 2048 is a groove 2056 which extends distally from the countersunk portion. The groove 2056 assists in retaining the sensor housing and cable components.

An additional component of the integration component 2012 is the inner ring 2026, shown in detail in FIG. 42. The inner ring 2026 includes a circumferential outer portion 2058. The outer portion 2058 is sized and shaped to fit into and be received by the end portion 2042 of the inner member 2024. The inner ring 2026 also includes a hub 2060 which defines a central round aperture 2062. The aperture 2062 receives a portion of in-flow tubing 2021 from the pump.

Figure 48:
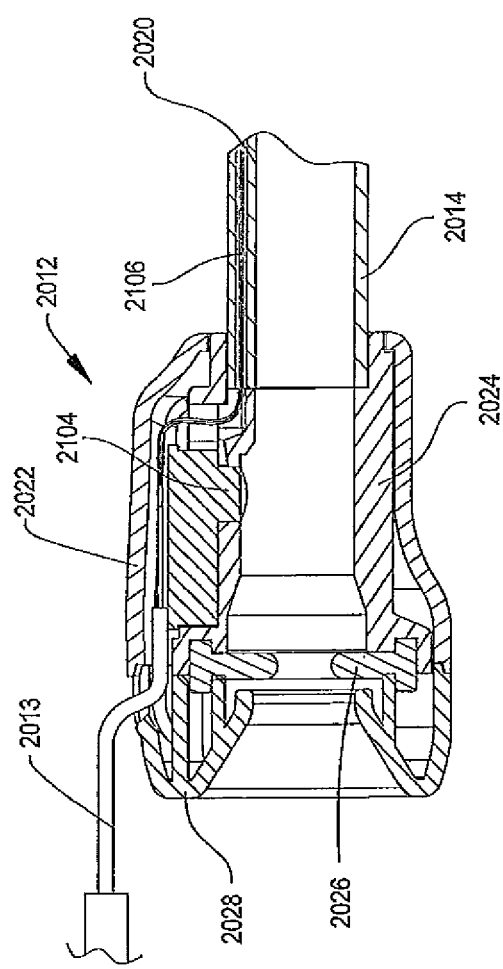
FIG. 48 is an elevational side cross-sectional view of the housing, a portion of the cabling and sensors, and a portion of the shaft and sheath of the in-joint sensor, taken along line XLVIII-XLVIII in FIG. 38.

As shown in FIG. 43, the proximal member 2028 is generally cylindrical in shape and acts as an end cap of the housing 2012. The proximal member 2028 includes a generally cylindrical outer shell 2064 which defines an inner space 2066 of the proximal member. In the inner space 2066, a first concentric ring 2068 extends axially from the proximal end of the proximal member 2028. A second ring 2070, which has a smaller diameter than and is concentric with the first ring 2068, also extends axially from the proximal end of the proximal member 2028. The second ring 2070 defines a central aperture 2072, which is sized and shaped to receive a portion of the in-flow tubing 2021. The central aperture 2072 aligns with central aperture 2062 of the inner ring 2026, and the interior space 2046 of the inner member 2024. The outer shell 2064 terminates distally in an inner lip 2074, which is sized and shaped to be received within the structure of the circular portion 2030 and top 2032 of the outer shell 2022. An upper ridge 2076 of the proximal member 2028 defines a channel 2078 at the top of the proximal member 2028. Channel 2078 receives a portion of cable 2013 and/or sensors housing, at least a majority of which resides in the interior of integration component 2012 (see FIG. 48).

The in-flow tubing 2021 is shown in FIG. 44. The in-flow tubing 2021 generally includes a housing 2080, a valve 2082, a seal 2084, and a flow tube 2086. The housing 2080 has a continuous opening (not shown) therethrough to allow liquid to flow from the valve 2082, through the housing 2080, and into and through the flow tube 2086. The housing 2080 is fixedly connected to the valve 2082 at one of the sides of the housing 2080. The valve 2082 is depicted as a standard ball valve, which includes an input port 2088 and a lever 2090 that is movable to open and close the valve. The valve 2082 may be one of a variety of other types of valves, if desired. At its distal end, the housing 2080 is fixedly attached to the flow tube 2086 which extends longitudinally in a distal direction. The longitudinal length of the flow tube 2086 is such a length that its distal tip 2092 resides entirely within the sheath 2014 (see FIG. 45). The seal 2084 attaches to the proximal end of housing 2080 and provides a liquid-tight seal such that liquid may flow freely through the housing 2080 without leaking.

Figure 45:
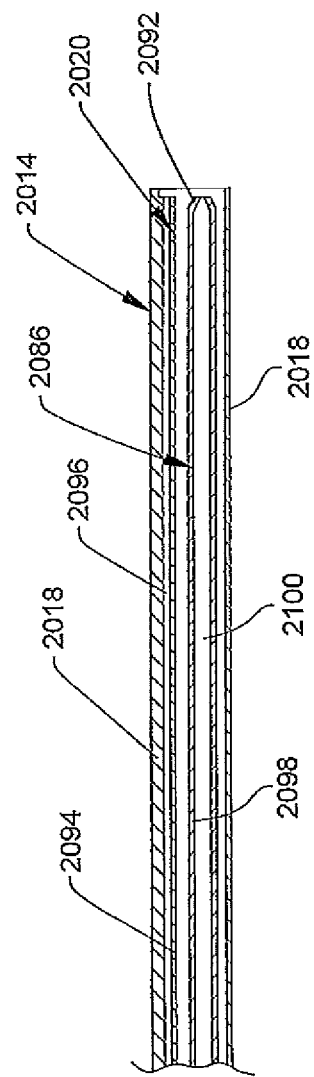
FIG. 45 is an elevated side cross-sectional view of a portion of the shaft and portion of the in-flow tubing of the in-joint sensor, taken along the line XLV-XLV in FIG. 38.

FIG. 45 shows the interior of the sheath 2014, with the flow tube 2086 of the in-flow tubing 2021 inserted therein. Shaft 2020 is preferably integrally formed with the wall 2015 of the sheath 2014. The shaft 2020 includes a wall 2094 which defines an interiorly-disposed elongated opening 2096. The shaft wall 2094 has a minimal thickness such that the temperature in the joint or other surgical area can be accurately sensed through the sheath 2014. The shaft 2020 also allows the temperature sensor to be isolated from the surgical fluid. The elongated opening 2096 is substantially parallel to the longitudinal axis of the sheath 2014. The elongated opening 2096 is sized to receive a portion of a temperature sensor, discussed in more detail below. The flow tube 2086 includes a generally rigid outer wall 2098 which terminates distally in the distal tip 2092. The distal tip 2092 tapers inwardly, that is, toward the central longitudinal axis of the flow tube 2086, as it extends distally. The outer wall 2098 defines an internal fluid flow passageway 2100. The passageway 2100 is for the conveyance and dissemination of fluids from the pump to the surgical site, such as a joint.

FIG. 47 shows the sensors and attached cable 2013, from the bottom with respect to the preferred arrangement of the sensors in use. Cable 2013 is preferably an Ethernet cable, but can be any cable that is capable of transferring data and enough electricity to ensure that the sensors are activated during surgery. The cable 2013 preferably is soldered directly to the sensor wires and/or solder pads on one end of the cable, and has a connector 2101, such as an RJ45 connector, at the other end. Attached to cable 2013 is a housing 2102 which contains a pressure sensor 2104. The pressure sensor 2104 is preferably a peizoresistive transducer and is disposable, along with the remainder of the in-joint sensor 2010. The pressure sensor 2104 depends from the bottom of the housing 2102 and into the pressure sensor aperture 2052 of the tray 2048. The pressure sensor is thus adjacent, or extends into, the interior space 2046 of the inner member 2024 (see FIG. 48). The pressure of the fluid is measured by fluid entering the space between the outer wall 2018 of the sheath 2014 and the outer wall 2098 of the flow tube 2086. Due to the proximity of the pressure sensor 2104 to the surgical site and the static column of fluid between the joint and the pressure sensor, the pressure in the joint can be accurately controlled. It is also contemplated that one of an air-water separator sensor and a membrane-based sensor could be employed to measure and regulate pressure in the joint.

A temperature sensor 2106 extends distally from the housing 2102. The temperature sensor 2106 is generally a wire thermistor that is sensitive to differences in temperature and is connected to the cable 2013 such that temperature information can be relayed from the joint area back to the pump or other device, via the cable 2013. The temperature sensor 2106 is received in the elongated opening 2096 of the shaft 2020 (see FIG. 48), and preferably extends distally to a location that is adjacent the distal end of the shaft 2020, such that when in use, the distal end of the temperature sensor 2106 is very near the joint or other bodily part being operated on. Thus, an accurate temperature reading at the surgery site is ensured.

The temperature information that is relayed to the pump 14 via cable 2013 can result in the pump 14 taking a number of different actions to maintain the desired temperature in the joint. For example, the inflow of fluid through the sheath 2014 or other structure can be increased, the outflow of fluid from the joint site can be increased, a dedicated outflow pinch valve can be opened to remove heated fluid from the joint quickly, or power to an ablation device can be reduced or eliminated to cool the joint surgical site.

Figure 50:
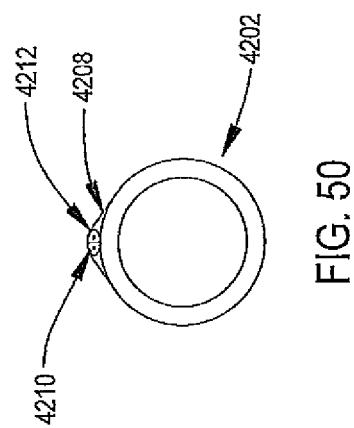
FIG. 50 is an end elevational view of a cannula, sheath, and sensors of the in-joint sensor of FIG. 49.
Figure 49:
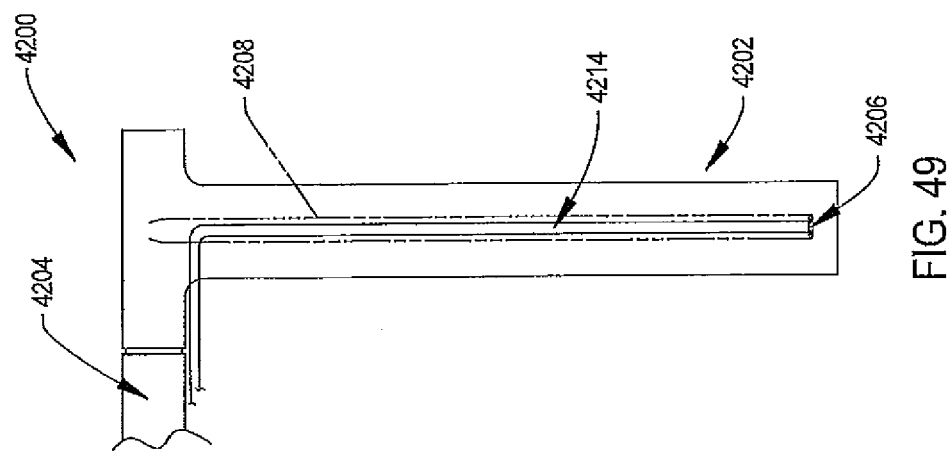
FIG. 49 is a top plan view of a second embodiment of an in-joint sensor which employs fiber optic cables.

FIG. 49 shows a second embodiment of an in-joint sensor. This in-joint sensor 4200 generally includes a cannula 4202 that is attached to in-flow tubing 4204. The cannula 4202 is generally circular in cross section, and thus tubular in nature (see FIG. 50), and includes a sensing element 4206 adjacent its distal end. Attached to the cannula 4202 (at the top of the cannula as depicted in FIG. 50), is a sheath 4208. The sheath 4208 is fixedly attached to the cannula 4202 and receives a pressure sensor 4210 and a temperature sensor 4212 near its distal end and one or more fiber optic cables 4214 therethrough. Each of the pressure sensor 4210 and temperature sensor 4212 can have a diameter of about 120 microns to about 140 microns. The fiber optic cable 4214 is attached to each of the pressure sensor 4210 and temperature sensor 4212 at one end of the cable 4214, and are attached to either the pump control unit or to a converter, which is in turn connected to the pump control unit, at the other end of cable 4214.

The above-described in-joint sensors 2010, 4200 may also transmit information wirelessly to a pump control unit or other device. Such a wireless system eliminates the need for wires or a cable such as cable 2013. In this embodiment, both the pressure sensing device and the temperature sensing device are connected to a miniature printed circuit board (PCB) 4220, which could be of the type that is flexible to conform to the shape of the device, which would minimize space requirement and which comprises or is connected to a wireless transmitter 4222. See FIG. 51. The PCB 4220 contains a disposable wireless chipset and necessary circuitry to read the information conveyed by the pressure and temperature sensing devices.

The wireless device uses components such that the current draw is minimal to operate the devices. Accordingly, a miniature battery 4224 can be used to run the sensors and the wireless transmitter 4222 throughout the duration of a procedure.

In use, the pressure and temperature sensors 2020, 2104 receive data which is gathered by the PCB 4220 and processed by a micro-control on the PCB 4220. The transmitter 4222 sends the data wirelessly to a receiver on the control unit or other diagnostic device. The receiver may include a standard USB connector for easy connection to a control device.

A third embodiment of an in-joint sensor 5200 is shown in FIGS. 52, 53A, and 53B. The in-joint sensor 5200 is a needle-scopic sensor that includes an outer housing 5202, which is generally frustoconical in shape and which has a cannula 5204 therein. On its exterior, the housing 5202 has a spiral grip 5206. The grip 5206 provides friction with tissue to assist in retaining the needle-scopic sensor system 5200 in place. Adjacent its proximal end, the needle-scopic sensor system 5200 includes a sensor assembly housing 5208 which may include a pressure sensor such as that shown as 2104 in FIG. 47, and other needed electronics, including if desired, a miniature PCB for wireless transmission. Alternatively, the sensing device 5200 has a cable 5210 attached to it, for connection to the pump console.

FIG. 53A is an end view of a first embodiment of the sensor system 5200. A thermistor 5212, or other temperature sensing element, extends lengthwise within the cannula

5204. In addition to the thermistor 5212, the cannula 5204 defines a channel 5214 therein for receiving fluid for the purpose of sensing pressure in a similar fashion to the first sensor embodiment depicted in FIGS. 38-48.

Figure 51:
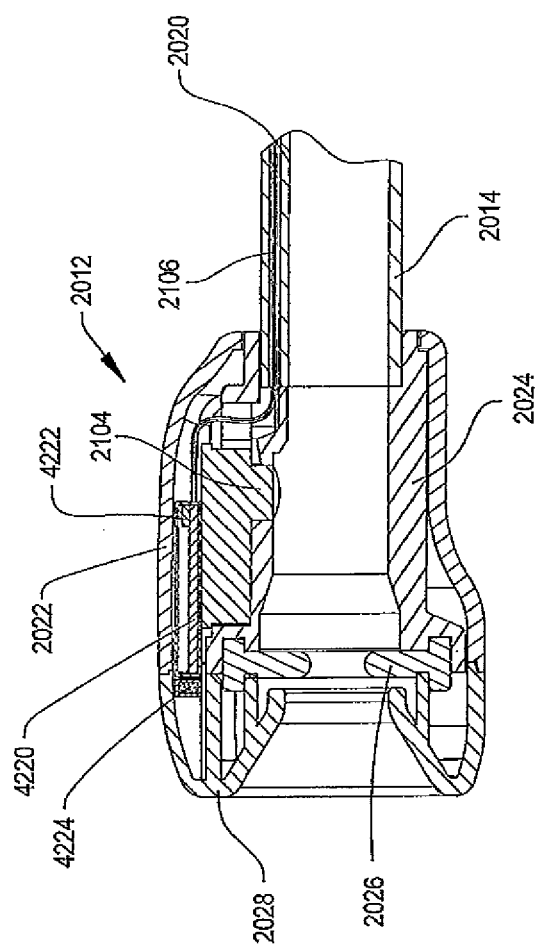
FIG. 51 is an elevational side cross-sectional view of the housing, similar to that of FIG. 48, including a wireless transmitter and battery.

Alternatively, a microfiber optic pressure and temperature sensor array, shown in FIG. 53B and similar to that of the second embodiment depicted in FIGS. 49-51, may be used. In this embodiment, a solid inner housing 5216 extends throughout the length of the outer housing 5202. The inner housing 5216 has therein a fiber optic temperature sensor 5218 and a fiber optic pressure sensor 5220. The fiber optic sensors 5218, 5220 are embedded in the inner housing 5216, leaving no open channel therein.

The above-described in-joint sensor unit has many advantages over presently commercial joint sensors. First, the novel in-joint sensor is disposable, thus reducing labor costs by eliminating cleaning and sterilization of a cannula and other components. Second, this in-joint sensor allows for direct measurement of in-joint pressure and temperature, which improves the control of the pump. Third, the inventive disposable in-joint sensor eliminates the need for pressure and/or temperature calibration since the inter-articular pressure and temperature are measured directly.

It is to be understood that variations and modifications can be made on the aforementioned embodiments without departing from the concepts of the present invention. For example, it is contemplated that many of the steps of the routines can be revised and provide the same functions. Further, the order of the steps can be changed in many instances. Furthermore, it is to be understood that such concepts are intended to be covered by the following claims unless these claims by their language expressly state otherwise.

I claim:

1. A cassette for a pump comprising:
    a housing having an internal flow path including an ingress path section and an egress path section;
    peristaltic tubing connected to the housing and being fluidly located between the ingress path section and the egress path section;
    an input tube fluidly connected to the ingress path section and being configured to provide a fluid to the housing, with the ingress path section being fluidly located between the input tube and the peristaltic tubing; and
    an inflow tube fluidly connected to the egress path section and being configured to provide the fluid to a patient, with the egress path section being fluidly located between the ingress path section and the inflow tube;
    the internal flow path including a pressure sensing region in the egress path section; and
    the housing including a pressure sensing flexible membrane being fluidly connected to the internal flow path through a slot in a wall of the housing.

2. The cassette for the pump of claim 1, wherein:
the cassette is an inflow cassette.

3. The cassette for the pump of claim 1, wherein:
the housing includes a top surface with the pressure sensing flexible membrane being located at the top surface.

4. The cassette for the pump of claim 3, wherein:
the top surface has a contoured area surrounding the pressure sensing flexible membrane for allowing a pressure sensor to easily be aligned with the pressure sensing flexible membrane; and
the contoured area includes a ramp surrounding the pressure sensing flexible membrane.

5. The cassette for the pump of claim 4, wherein:
the pressure sensing flexible membrane is circular.

6. The cassette for the pump of claim 3, wherein:
the housing includes a bottom surface having a lock block thereon; and
the lock block has a lock edge configured to mate with a lock device of the pump to lock the cassette within the pump.

7. The cassette for the pump of claim 1, wherein:
the inflow tube includes a pinch clamp for preventing fluid flow through the inflow tube.

8. The cassette for the pump of claim 1, wherein:
the input tube includes a plurality of entrance paths for allowing the input tube to be connected to a plurality of fluid sources;
the input tube further includes an exit path fluidly connected to the ingress path section; and
the plurality of entrance paths and the exit path meet at a junction.

9. The cassette for the pump of claim 8, wherein:
each of the entrance paths includes a pinch clamp for preventing fluid flow through the plurality of entrance paths.

10. The cassette for the pump of claim 9, wherein:
the housing comprises a body having a pair of legs;
the pair of legs define a U-shaped recessed area; and
the peristaltic tubing is located within the U-shaped recessed area.

11. The cassette for the pump of claim 9, wherein:
the housing includes a radio frequency chip therein for communicating with the pump when the cassette is positioned within the pump.

12. A pump assembly comprising:
    a pump housing having a cassette receptacle therein, the cassette receptacle having a rotary motor rotating a wheel; and
    a cassette configured to be inserted into the cassette receptacle of the pump housing, the cassette comprising:
        a cassette housing having an internal flow path including an ingress path section and an egress path section;
        peristaltic tubing connected to the cassette housing and being fluidly located between the ingress path section and the egress path section;
        an input tube fluidly connected to the ingress path section and being configured to provide a fluid to the cassette housing, with the ingress path section being fluidly located between the input tube and the peristaltic tubing; and
        an inflow tube fluidly connected to the egress path section and being configured to provide the fluid to a patient, with the egress path section being fluidly located between the ingress path section and the inflow tube;
    the wheel engaging the peristaltic tubing when the cassette is inserted into the cassette receptacle of the pump housing, rotation of the wheel by the rotary motor causing the fluid to be pushed through the cassette from the input tube to the inflow tube;
    the internal flow path including a pressure sensing region in the egress path section; and
    the housing including a pressure sensing flexible membrane being fluidly connected to the internal flow path through a slot in a wall of the cassette housing.

13. The cassette for the pump assembly of claim 12, wherein:

the cassette is an inflow cassette.

14. The pump assembly of claim 12, wherein:

the pump housing includes a sensor abutting the pressure sensing flexible membrane when the cassette is inserted into the cassette receptacle of the pump housing; and the sensor measures pressure of the fluid within the pressure sensing region in the egress path section of the internal flow path of the cassette.

15. The pump assembly of claim 14, wherein:

the cassette housing includes a top surface with the pressure sensing flexible membrane being located at the top surface.

16. The pump assembly of claim 15, wherein:

the top surface of the cassette housing has a contoured area surrounding the pressure sensing flexible membrane;

the contoured area includes a ramp surrounding the pressure sensing flexible membrane;

the sensor is located in a projecting surface including an upper surface and a pair of angled surfaces on sides of the upper surface; and the upper surface and the pair of angled surfaces of the projecting surface are received within the ramp of the contoured area of the cassette housing to properly align the sensor with the pressure sensing flexible membrane.

17. The pump assembly of claim 16, wherein:

the projecting surface is biased by a spring outward to allow the projecting surface to move against bias of the spring during insertion of the cassette into the cassette receptacle and then move with the bias of the spring once the cassette is properly located within the cassette receptacle.

18. The pump assembly of claim 16, wherein:

the pressure sensing flexible membrane is circular.

19. The pump assembly of claim 12, wherein:

the cassette housing includes a bottom surface having a lock block thereon;

the lock block has a lock edge; and the pump housing has a movable lock lever with a lock wedge configured to selectively abut against the lock edge to lock the cassette within the pump housing.

20. The pump assembly of claim 12, wherein:

the inflow tube includes a pinch clamp for preventing fluid flow through the inflow tube.

21. The pump assembly of claim 12, wherein:

the input tube includes a plurality of entrance paths for allowing the input tube to be connected to a plurality of fluid sources;

the input tube further includes an exit path fluidly connected to the ingress path section; and the plurality of entrance paths and the exit path meet at a junction.

22. The pump assembly of claim 21, wherein:

each of the entrance paths includes a pinch clamp for preventing fluid flow through the plurality of entrance paths.

23. The pump assembly of claim 12, wherein:

the cassette housing comprises a body having a pair of legs;

the pair of legs define a U-shaped recessed area; and the peristaltic tubing is located within the U-shaped recessed area.

24. The pump assembly of claim 12, wherein:

the cassette housing includes a radio frequency chip therein for communicating with the pump housing.

* * * * *